United States Patent
Gruber et al.

(10) Patent No.: US 10,259,842 B2
(45) Date of Patent: Apr. 16, 2019

(54) PURIFICATION OF RECOMBINANTLY PRODUCED POLYPEPTIDES

(71) Applicants: MedImmune Limited, Cambridge (GB); MedImmune, LLC, Gaithersburg, MD (US)

(72) Inventors: David Edwin Gruber, Cambridge (GB); Richard Edward Turner, Cambridge (GB); Jared Samuel Bee, Gaithersburg, MD (US); Christopher Douglas Afdahl, Gaithersburg, MD (US); Liu Tie, Gaithersburg, MD (US)

(73) Assignees: MedImmune, LLC, Gaithersburg, MD (US); Medimmune Limited, Cambridge (GB)

( * ) Notice: Subject to any disclaimer, the term of this patent is extended or adjusted under 35 U.S.C. 154(b) by 348 days.

(21) Appl. No.: 14/890,823

(22) PCT Filed: May 13, 2014

(86) PCT No.: PCT/US2014/037821
§ 371 (c)(1),
(2) Date: Nov. 12, 2015

(87) PCT Pub. No.: WO2014/186350
PCT Pub. Date: Nov. 20, 2014

(65) Prior Publication Data
US 2016/0108084 A1    Apr. 21, 2016

Related U.S. Application Data

(60) Provisional application No. 61/823,520, filed on May 15, 2013.

(51) Int. Cl.
*C07K 1/22* (2006.01)
*C11D 7/26* (2006.01)
*C07K 16/24* (2006.01)
*C11D 7/10* (2006.01)

(52) U.S. Cl.
CPC .............. *C07K 1/22* (2013.01); *C07K 16/244* (2013.01); *C11D 7/10* (2013.01); *C11D 7/265* (2013.01)

(58) Field of Classification Search
None
See application file for complete search history.

(56) References Cited

U.S. PATENT DOCUMENTS

| | | | |
|---|---|---|---|
| 7,807,799 B2 | 5/2010 | Fahrner et al. | |
| 2012/0039807 A1* | 2/2012 | Freimoser-Grundschober | C07K 16/30 424/9.1 |
| 2012/0101262 A1 | 4/2012 | Arunakumari et al. | |
| 2012/0283416 A1* | 11/2012 | Frauenschuh | C07K 1/22 530/387.3 |

FOREIGN PATENT DOCUMENTS

| | | | | |
|---|---|---|---|---|
| EP | 2578286 A1 | 10/2013 | | |
| WO | WO-2005113604 A2 * | 12/2005 | ......... | B01D 15/3804 |
| WO | WO 2010/141039 A1 | 9/2010 | | |
| WO | WO 2014/066468 A1 | 1/2014 | | |
| WO | WO 2014/133460 A1 | 4/2014 | | |
| WO | WO 2015/166072 A1 | 5/2015 | | |

OTHER PUBLICATIONS

Elin Monie "Evaluation of the 96-we;; format for screening of chromatographic buffer conditions" Master's degree project; pp. 1-55 (Year: 2006).*
Newcombe et al. "Optimised affinity purification of polyclonal antibodies from hyperimmunised ovine serum using a synthetic Protein A adsorbent, MAbsorbent A2P". Journal of Chromatography B, Jan. 25, 2005 (Jan. 25, 2005), vol. 814, pp. 209-215.
Goetzinger W K et al. "Buffer system for the separation of neutral and charged small molecules using micellar electrokinetic chromatography with mass spectrometric detection", Journal of Chromatography, Elsevier Science Publishers B.V, NL, vol. 1079, No. 1-2, Jun. 24, 2005 (Jun. 24, 2005), pp. 372-381.
International Search Report for PCT/US2014/037821 dated Oct. 24, 2014.
International Preliminary Report on Patentability for PCT/US2014/037821 dated Nov. 17, 2015.
Written Opinion of the International Searching Authority for PCT/US2014/037821 dated Oct. 24, 2014.
Supplemental European Search Report for Application No. EP 14797310 dated Oct. 21, 2016.

* cited by examiner

*Primary Examiner* — Daniel E Kolker
*Assistant Examiner* — James L Rogers

(57) ABSTRACT

Described herein is a method for separating a recombinantly produced polypeptide from host cell protein. The method includes a step of loading a clarified cell culture supernatant that includes the recombinantly produced polypeptide and the HCP onto a Protein A chromatography column and washing the Protein A chromatography column with a wash buffer comprising a fatty acid having a chain length of at least about 6 carbon atoms, or a fatty acid salt thereof to remove HCP and then recovering the recombinantly produced polypeptide.

11 Claims, 21 Drawing Sheets

Specification includes a Sequence Listing.

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      AB1 VH CDR1 peptide

<400> SEQUENCE: 1

Ser Asn Tyr Met Ile
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      AB1 VH CDR2 peptide

<400> SEQUENCE: 2

Asp Leu Tyr Tyr Tyr Ala Gly Asp Thr Tyr Tyr Ala Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      AB1 VH CDR3 peptide

<400> SEQUENCE: 3

Trp Ala Asp Asp His Pro Pro Trp Ile Asp Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      AB1 VL CDR1 peptide

<400> SEQUENCE: 4
```

Arg Ala Ser Gln Gly Ile Ser Ser Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      AB1 VL CDR2 peptide

<400> SEQUENCE: 5

Lys Ala Ser Thr Leu Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      AB1 VL CDR3 peptide

<400> SEQUENCE: 6

Gln Gln Ser Trp Leu Gly Gly Ser
1               5

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      AB1 VH polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Trp Ala Asp Asp His Pro Pro Trp Ile Asp Leu Trp Gly Arg
            100                 105                 110

Gly Thr Leu Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      AB1 VL polypeptide

<400> SEQUENCE: 8

Asp Ile Gln Met Thr Gln Ser Pro Ser Thr Leu Ser Ala Ser Val Gly

```
              1               5                  10                  15
            Asp Arg Val Thr Ile Thr Cys Arg Ala Ser Gln Gly Ile Ser Ser Trp
                            20                  25                  30

Leu Ala Trp Tyr Gln Gln Lys Pro Gly Lys Ala Pro Lys Val Leu Ile
                    35                  40                  45

Tyr Lys Ala Ser Thr Leu Glu Ser Gly Val Pro Ser Arg Phe Ser Gly
                50                  55                  60

Ser Gly Ser Gly Thr Glu Phe Thr Leu Thr Ile Ser Ser Leu Gln Pro
            65                  70                  75                  80

Asp Asp Phe Ala Thr Tyr Tyr Cys Gln Gln Ser Trp Leu Gly Ser
                            85                  90                  95

Phe Gly Gln Gly Thr Lys Leu Glu Ile Lys
                        100                 105

<210> SEQ ID NO 9
<211> LENGTH: 7
<212> TYPE: PRT
<213> ORGANISM: Homo sapiens
<220> FEATURE:
<223> OTHER INFORMATION: AB2 VH CDR1

<400> SEQUENCE: 9

Ala Asp Gly Tyr Tyr Trp Ser
1               5

<210> SEQ ID NO 10
<211> LENGTH: 16
<212> TYPE: PRT
<213> ORGANISM: Homo sapiens
<220> FEATURE:
<223> OTHER INFORMATION: AB2 VH CDR2

<400> SEQUENCE: 10

Ser Leu Tyr Tyr Ser Gly Ser Thr Tyr Tyr Asn Pro Ser Leu Lys Gly
1               5                   10                  15

<210> SEQ ID NO 11
<211> LENGTH: 15
<212> TYPE: PRT
<213> ORGANISM: Homo sapiens
<220> FEATURE:
<223> OTHER INFORMATION: AB2 VH CDR3

<400> SEQUENCE: 11

Thr Pro Ala Tyr Phe Gly Gln Asp Arg Thr Asp Phe Phe Asp Val
1               5                   10                  15

<210> SEQ ID NO 12
<211> LENGTH: 11
<212> TYPE: PRT
<213> ORGANISM: Homo sapiens
<220> FEATURE:
<223> OTHER INFORMATION: AB2 VL CDR1

<400> SEQUENCE: 12

Arg Ala Ser Gln Gly Ile Ser Ser Trp Leu Ala
1               5                   10

<210> SEQ ID NO 13
<211> LENGTH: 7
<212> TYPE: PRT
<213> ORGANISM: Homo sapiens
<220> FEATURE:
<223> OTHER INFORMATION: AB2 VL CDR2
```

<400> SEQUENCE: 13

Lys Ala Ser Thr Leu Glu Ser
1               5

<210> SEQ ID NO 14
<211> LENGTH: 9
<212> TYPE: PRT
<213> ORGANISM: Homo sapiens
<220> FEATURE:
<223> OTHER INFORMATION: AB2 VL CDR3

<400> SEQUENCE: 14

Gln Gln Ser His His Pro Pro Trp Thr
1               5

<210> SEQ ID NO 15
<211> LENGTH: 375
<212> TYPE: DNA
<213> ORGANISM: Homo sapiens
<220> FEATURE:
<223> OTHER INFORMATION: AB2 VH

<400> SEQUENCE: 15
caggtacagc tgcaggagtc aggcccagga ctggtgaagc cttcagagac cctgtccctc        60
acctgcactg tctctggtgg ctccatcagc gctgatggtt actactggag ctggatccgg       120 cagcccccg ggaagggct ggagtggatt gggagtctct attatagtgg gagcacctac         180
tacaacccgt ccctcaaggg tcgagtcacc atatcaggag acacgtccaa gaaccagttc       240
tccctgaagc tgagctctgt gaccgctgcg gacacggccg tatattactg tgcaagaacc       300
cccgcgtatt tcggccagga caggacggat ttctttgacg tctggggcag gggaaccctg       360
gtcaccgtct cctca                                                        375

<210> SEQ ID NO 16
<211> LENGTH: 125
<212> TYPE: PRT
<213> ORGANISM: Homo sapiens
<220> FEATURE:
<223> OTHER INFORMATION: AB2 VH

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ala Asp
            20                  25                  30

Gly Tyr Tyr Trp Ser Trp Ile Arg Gln Pro Pro Gly Lys Gly Leu Glu
        35                  40                  45

Trp Ile Gly Ser Leu Tyr Tyr Ser Gly Ser Thr Tyr Tyr Asn Pro Ser
    50                  55                  60

Leu Lys Gly Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Pro Ala Tyr Phe Gly Gln Asp Arg Thr Asp Phe Phe
            100                 105                 110

Asp Val Trp Gly Arg Gly Thr Leu Val Thr Val Ser Ser
        115                 120                 125

<210> SEQ ID NO 17

```
<211> LENGTH: 321
<212> TYPE: DNA
<213> ORGANISM: Homo sapiens
<220> FEATURE:
<223> OTHER INFORMATION: AB2 VL

<400> SEQUENCE: 17
gacatccaga tgacccagtc tccttccacc ctgtctgcat ctgtaggaga cagagtcacc      60
atcacttgcc gggccagtca gggtattagt agctggttgg cctggtatca gcagaaacca     120
gggaaagccc ctaaggtctt gatctataag gcatctactt tagaaagtgg ggtcccatca     180
aggttcagcg gcagtggatc tgggacagaa ttcactctca ccatcagcag tctgcaacct     240
gatgattttg caacttacta ctgtcaacag agtcaccacc cgccgtggac gttcggccaa     300
gggaccaagc tggagatcaa a                                               321

<210> SEQ ID NO 18
<211> LENGTH: 107
<212> TYPE: PRT
<213> ORGANISM: Homo sapiens
<220> FEATURE:
<223> OTHER INFORMATION: AB2 VL

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser His His Pro Pro Trp
                85                  90                  95

Thr Phe Gly Gln Gly Thr Lys Leu Glu Ile Lys
            100                 105
```

PURIFICATION OF RECOMBINANTLY PRODUCED POLYPEPTIDES

1. INTRODUCTION

Cross-Reference to Related Applications

This application is a U.S. National Stage application of International Application No. PCT/US2014/037821, filed on May 13, 2014. International Application No. PCT/US2014/037821 claims the benefit under 35 U.S.C. § 119(e) of U.S. Provisional Application No. 61/823,520, filed on May 15, 2013. Each of the above listed applications is incorporated by reference herein in its entirety for all purposes.

1.1. Reference to a Sequence Listing

This application incorporates by reference a Sequence Listing submitted with this application as text file PURIF300WO1_SL created on May 13, 2014 and having a size of 8,521 bytes.

1.2. Field of the Invention

The present invention relates to the purification of recombinantly produced polypeptides. In a more particular embodiment, the invention relates to methods of separating recombinantly produced polypeptides from host cell proteins (HCPs).

1.3. Background of the Invention

Recombinantly produced polypeptides, such as antibodies and other proteins, are used in a wide array of diagnostic and therapeutic applications. The process of manufacturing recombinant polypeptides generally involves expression of the polypeptide in a host cell, and purification of the polypeptide.

Expression generally involves culturing a prokaryotic or eukaryotic host cell under appropriate conditions for the host cells to produce the recombinant polypeptide. The recombinant polypeptide can be expressed in different locations within the host cell, which can impact the methods used for isolation and purification of the product.

Once a recombinant polypeptide is expressed, intact host cells and cell debris are separated from the cell culture media in a process referred to as "cell harvesting." For example, host cells can be separated from the cell culture media by centrifugation or filtration to provide a clarified fluid (which can be referred to as the "cell culture supernatant") that includes the recombinant polypeptide and other impurities. Examples of impurities that may be found in the clarified cell culture supernatant include, but are not limited to, host cell proteins (HCP), nucleic acids, endotoxins, viruses, protein variants and protein aggregates.

Purification refers to the removal of impurities from the clarified cell culture supernatant and typically involves one or more chromatography steps. Typical processes include capture, intermediate purification or polishing, and final polishing steps. Affinity chromatography, for example, Protein A chromatography or ion exchange chromatography, is often used as a capture step. Often, capture is followed by at least two intermediate purification or polishing steps to increase purity and remove of viral contaminants. Intermediate purification or polishing steps are often accomplished by affinity chromatography, ion exchange chromatography, or hydrophobic interaction chromatography (HIC). In many processes, the final polishing step is accomplished using ion exchange chromatography, hydrophobic interaction chromatography, or gel filtration.

Preferably, biopharmaceutical products have a very high purity, with the concentration of impurities, such as host cell proteins, reduced to the range of parts per million relative to the desired product, or lower. Consequently, there remains a need for purification processes that optimize removal of impurities, in particular, host cell proteins.

2. SUMMARY OF THE INVENTION

Described herein is a method for separating a recombinantly produced polypeptide from host cell protein (HCP). In one embodiment, the method includes steps of: providing a clarified cell culture supernatant that includes the recombinantly produced polypeptide and the HCP; loading the clarified cell culture supernatant onto a Protein A chromatography column; washing the Protein A chromatography column with a wash buffer including a fatty acid having a chain length of at least about 6 carbon atoms, or a fatty acid salt thereof to remove HCP; and recovering the recombinantly produced polypeptide. In another embodiment, the method includes steps of equilibrating a Protein A chromatography column with an equilibration buffer; loading the clarified cell culture supernatant onto the Protein A chromatography column; re-equilibrating the loaded Protein A chromatography column with the equilibration buffer; washing the loaded Protein A chromatography column with a first wash buffer including a fatty acid having a chain length of at least about 6 carbon atoms, or a fatty acid salt thereof to remove HCP; washing the loaded Protein A chromatography column with a second wash buffer; and eluting the recombinantly produced polypeptide with an elution buffer. In another embodiment, a method of reducing protease contamination in a formulation including a recombinantly produced polypeptide is described. In another embodiment, a method of increasing stability of a recombinantly produced polypeptide is described. In another embodiment, a method of reducing HCP levels, including protease levels in a formulation is provided. Examples of proteases that may be removed include, but are not limited to, serine proteases, aspartyl proteases, such as cathepsin-D, cysteine proteases, metalloproteases and aminopeptidases.

In one embodiment, the chain length of the fatty acid or fatty acid salt is between 6 and 12 carbon atoms. In another embodiment, the chain length of the fatty acid or fatty acid salt is between 8 and 12 carbon atoms. In another embodiment, the chain length of the fatty acid or fatty acid salt is between 8 and 10 carbon atoms. In one embodiment, the fatty acid or fatty acid salt is selected from enanthic acid, caprylic acid, pelargonic acid, capric acid, undecyclic acid, lauric acid, and combinations thereof. In a more particular embodiment, the wash buffer includes caprylic acid, or a caprylic acid salt. In one embodiment, the wash buffer includes between about 25 mM to about 200 mM fatty acid. In another embodiment, the wash buffer includes between about 50 mM to about 100 mM fatty acid. In one embodiment, the wash buffer includes about 100 mM fatty acid.

In one embodiment, the wash buffer includes sodium chloride. In a more particular embodiment, the wash buffer includes the sodium chloride at a concentration between about 1.0M to about 2.5M. In one embodiment, the wash buffer includes sodium chloride at a concentration between about 2M to about 2.5M. In one embodiment, the wash buffer includes sodium chloride at a concentration of about 2.5M.

In one embodiment, the wash buffer has a pH between about 7 to about 9. In another embodiment, the wash buffer has a pH between about 8 to about 9. In another embodiment, the wash buffer has a pH between about 8.5 to about 9. In one embodiment, the wash buffer has a pH of about 9.

In a more particular embodiment, the wash buffer includes between about 50 mM and about 100 mM sodium caprylate at a pH between about 8 to about 9. In another embodiment, the wash buffer includes between about 50 mM and about 100 mM sodium caprylate at a pH between about 8 to about 9 and between about 2.0M to about 2.5 M sodium chloride. In another embodiment, the wash buffer includes about 100 mM sodium caprylate in 100 mM Tris at a pH of about 9.0. In one embodiment, the wash buffer includes about 100 mM sodium caprylate in 100 mM Tris at a pH of about 9.0 and about 2.5M sodium chloride.

In one embodiment, the cell culture harvest is clarified to obtain a clarified cell culture harvest, which is loaded onto the Protein A chromatography column. In one embodiment, the loaded Protein A column is re-equilibrated with an equilibration buffer prior to washing the column with the wash buffer. In one embodiment, the equilibration buffer includes sodium phosphate. In one embodiment, the equilibration buffer includes between about 10 mM and about 100 mM sodium phosphate. In one embodiment, the equilibration buffer includes between about 20 mM and about 50 mM sodium phosphate at a pH between about 6 and about 8. In another embodiment, the equilibration buffer includes about 20 mM sodium phosphate at a pH of about 7.

In one embodiment, the method includes a second wash step after the column is washed with the fatty acid wash buffer. In one embodiment, the second wash buffer includes sodium phosphate. In one embodiment, the second wash buffer includes between about 10 mM and about 100 mM sodium phosphate. In one embodiment, the second wash buffer includes between about 20 mM and about 50 mM sodium phosphate at a pH between about 6 and about 8. In one embodiment, the second wash buffer includes about 20 mM sodium phosphate at a pH of about 7.

In one embodiment, the recombinant protein is recovered by eluting the recombinant protein from the Protein A column with an elution buffer. In one embodiment, the elution buffer includes sodium citrate. In one embodiment, the elution buffer includes between about 25 mM and about 200 mM sodium citrate. In one embodiment, the elution buffer includes between about 50 mM and about 100 mM sodium citrate. In one embodiment, the elution buffer has a pH between about 2.0 and about 5.0. In one embodiment, the elution buffer has a pH of between about 3.0 and about 4.0. In one embodiment, the elution buffer includes about 100 mM sodium citrate at a pH of about 3.5.

In one embodiment, the recombinantly produced polypeptide purified by the method above is an antibody, or a binding fragment thereof. In one embodiment, the recombinantly produced polypeptide includes a fully human monoclonal antibody selected from antibody 1 (a human anti-interleukin (IL)-6 antibody) or antibody 2 (a monoclonal antibody to human IL-18) (NCIMB accession number 41786).

In another embodiment, the recombinantly produced polypeptide includes an antibody having a light chain acid variable sequence of antibody 1 (SEQ ID NO:8). In another embodiment, the recombinantly produced polypeptide includes an antibody having a heavy chain variable sequence of antibody 1 (SEQ ID NO:7). In another embodiment, the recombinantly produced polypeptide includes an antibody having a light chain variable sequence of antibody 1 (SEQ ID NO: 8) and a heavy chain variable sequence of antibody 1 (SEQ ID NO:7).

In another embodiment, the recombinantly produced polypeptide includes an antibody having a light chain acid variable sequence of antibody 2 (SEQ ID NO:18). In another embodiment, the recombinantly produced polypeptide includes an antibody having a heavy chain variable sequence of antibody 2 (SEQ ID NO.16). In another embodiment, the recombinantly produced polypeptide includes an antibody having a light chain variable sequence of antibody 2 (SEQ ID NO: 18) and a heavy chain variable sequence of antibody 2 (SEQ ID No.:16).

In one embodiment, the antibody includes a heavy chain amino acid sequence having one or more complementarity determining regions (CDRs) of antibody 1 or antibody 2. The terms CDR region or CDR, refer to the hypervariable regions of the heavy and light chains of the immunoglobulin as defined by Kabat et al. (Kabat, E. A. et al. (1991) Sequences of Proteins of Immunological Interest, 5th Edition. US Department of Health and Human Services, Public Service, NIH, Washington or later editions) or Chothia and Lesk (J. Mol. Biol., 196:901-917 (1987)). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes. Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody. One of skill in the art is able to determine CDR regions of an antibody. In general, HCDR1 is about 5 amino acids long, consisting of Kabat residues 31-35; HCDR2 is about 17 amino acids long, consisting of Kabat residues 50-65; HCDR3 is about 11 or 12 amino acids long, consisting of Kabat residues 95-102, optionally including Kabat residue 100D; LCDR1 is about 11 amino acids long, consisting of Kabat residues 24-34; LCDR2 is about 7 amino acids long, consisting of Kabat residues 50-56; and LCDR3 is about 8 or 9 amino acids long, consisting of Kabat residues 89-97, optionally including Kabat residue 95.

In one embodiment, the recombinantly produced polypeptide is an antibody or binding fragment thereof that includes a light chain amino acid sequence that includes one or more light chain CDR sequences for antibody 1 selected from LCDR1 (SEQ ID NO:4); LCDR2 (SEQ ID NO: 5), LCDR3 (SEQ ID NO:6), and combinations thereof. In one embodiment, the recombinantly produced polypeptide is an antibody that includes a heavy chain amino acid sequence that includes one or more of the heavy chain CDR sequences for antibody 1 selected from HCDR1 (SEQ ID NO: 1); HCDR2 (SEQ ID NO: 2), HCDR3 (SEQ ID NO:3), and combinations thereof. In one embodiment, the recombinantly produced polypeptide is an antibody or binding fragment thereof that includes a light chain amino acid sequence that includes LCDR1 (SEQ ID NO:4); LCDR2 (SEQ ID NO: 5), and LCDR3 (SEQ ID NO:6) from antibody 1 and a heavy chain amino acid sequence that includes HCDR1 (SEQ ID NO: 1); HCDR2 (SEQ ID NO: 2) and HCDR3 (SEQ ID NO:3) of antibody 1.

In one embodiment, the recombinantly produced polypeptide is an antibody or binding fragment thereof that includes a light chain amino acid sequence that includes one or more light chain CDR sequences for antibody 2 selected from LCDR1 (SEQ ID NO:12); LCDR2 (SEQ ID NO: 13), LCDR3 (SEQ ID NO:14), and combinations thereof. In one embodiment, the recombinantly produced polypeptide is an antibody that includes a heavy chain amino acid sequence having one or more of the heavy chain CDR sequences for antibody 2 selected from HCDR1 (SEQ ID NO: 9); HCDR2 (SEQ ID NO: 10), HCDR3 (SEQ ID NO: 11), and combinations thereof. In one embodiment, the recombinantly produced polypeptide is an antibody or binding fragment thereof that includes a light chain amino acid sequence that includes LCDR1 (SEQ ID NO: 12); LCDR2 (SEQ ID NO: 13), and LCDR3 (SEQ ID NO: 14) from antibody 2 and a heavy chain amino acid sequence that includes HCDR1 (SEQ ID NO: 9); HCDR2 (SEQ ID NO: 10) and HCDR3 (SEQ ID NO: 11) of antibody 2.

In another embodiment, a wash buffer for separating a recombinantly produced polypeptide from host cell protein (HCP) in a Protein A chromatography column is provided. In one embodiment, the wash buffer includes a fatty acid or a fatty acid salt having a chain length of at least 6 carbon atoms. In one embodiment, the chain length of the fatty acid or fatty acid salt is between 6 and 12 carbon atoms. In one embodiment, the chain length of the fatty acid or fatty acid salt is between 8 and 12 carbon atoms. In one embodiment, the chain length of the fatty acid or fatty acid salt is between 8 and 10 carbon atoms. In one embodiment, the fatty acid or fatty acid salt is selected from enanthic acid, caprylic acid, pelargonic acid, capric acid, undecyclic acid, lauric acid, and combinations thereof. In one embodiment, the wash buffer includes caprylic acid, or a caprylic acid salt. In one embodiment, the wash buffer includes between about 25 mM to about 200 mM fatty acid. In one embodiment, the wash buffer includes between about 50 mM to about 100 mM fatty acid. In one embodiment, the wash buffer includes about 100 mM fatty acid. In one embodiment, the wash buffer includes sodium chloride. In one embodiment, the wash buffer includes the sodium chloride at a concentration of between about 1.0M to about 2.5M. In one embodiment, the wash buffer includes sodium chloride at a concentration of about 2M to about 2.5M. In one embodiment, the wash buffer includes sodium chloride at a concentration of about 2.5M. In one embodiment, the wash buffer has a pH between about 7 to about 9. In one embodiment, the wash buffer has a pH between about 8 to about 9. In one embodiment, the wash buffer has a pH between about 8.5 to about 9. In one embodiment, the wash buffer has a pH of about 9. In one embodiment, the wash buffer includes between about 50 mM and about 100 mM sodium caprylate at a pH between about 8 to about 9. In one embodiment, the wash buffer includes between about 50 mM and about 100 mM sodium caprylate at a pH between about 8 to about 9 and between about 2.0M to about 2.5 M sodium chloride. In one embodiment, the wash buffer includes about 100 mM sodium caprylate in 100 mM Tris at a pH of about 9.0. In one embodiment, the wash buffer includes about 100 mM sodium caprylate in 100 mM Tris at a pH of about 9.0 and about 2.5M sodium chloride.

3. BRIEF DESCRIPTION OF THE FIGURES

Figure 10A:
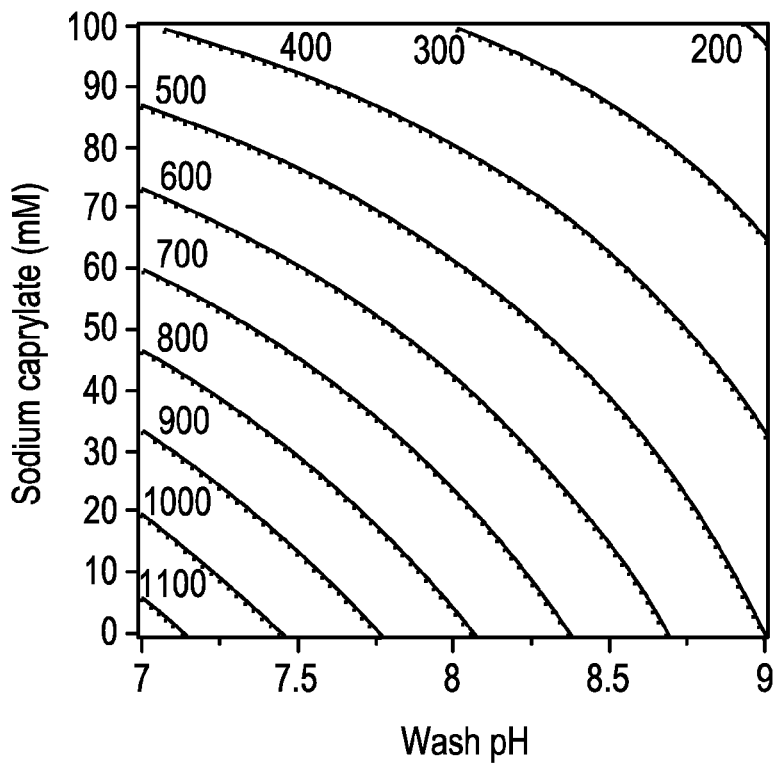
Figure 10B:
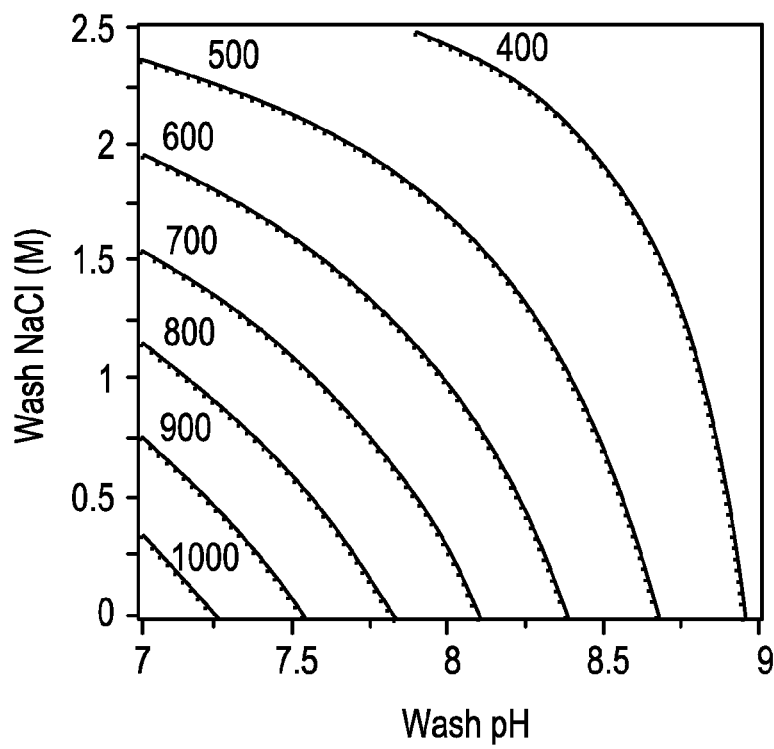
Figure 10C:
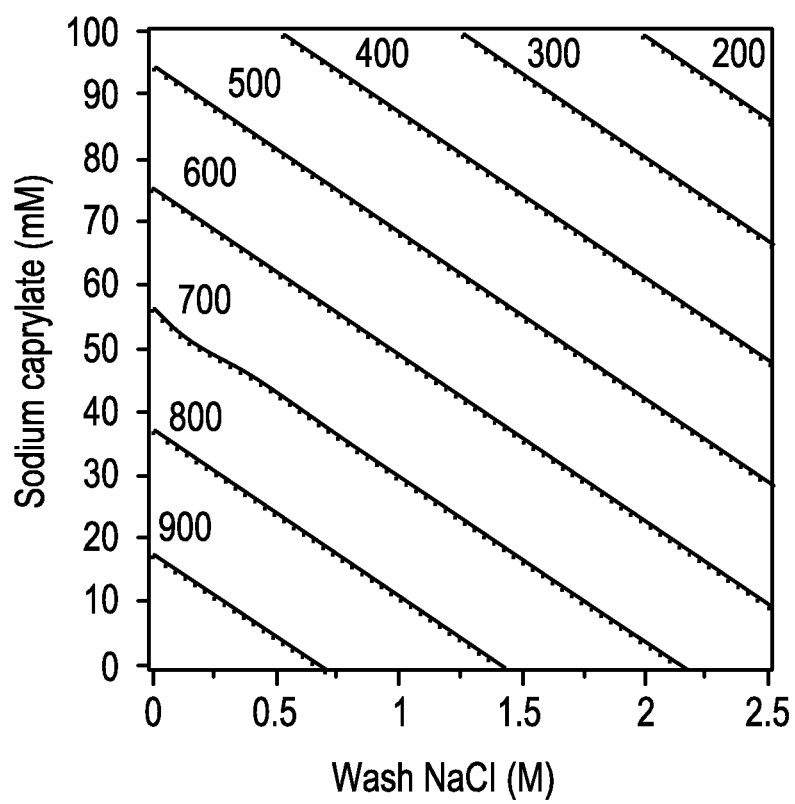

FIGS. 10A-C are graphs showing the effect of wash pH, sodium chloride and sodium caprylate, in combination, on HCP levels pre-filtration.

Figure 11:
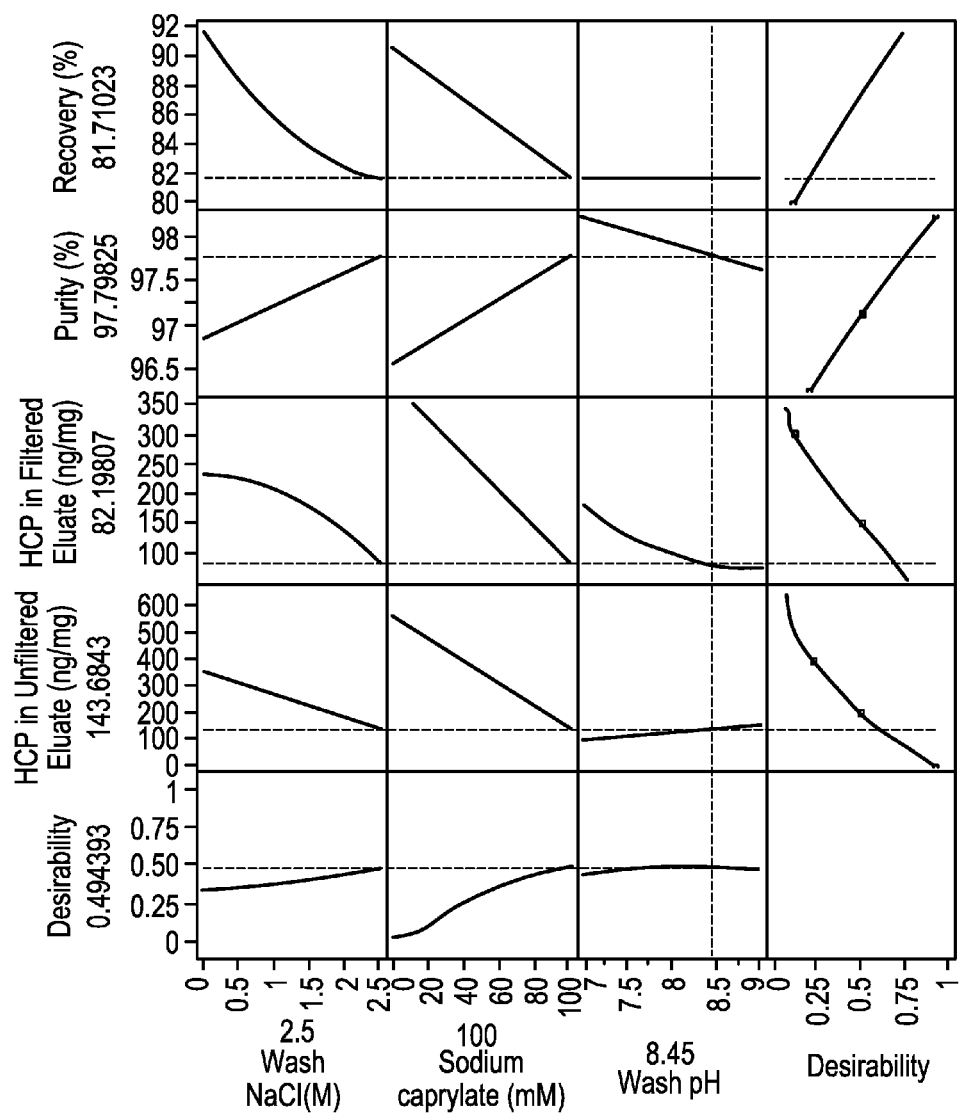

FIG. 11 shows the effect of wash pH, sodium chloride and sodium caprylate on HCP levels.

Figures 12, 13:
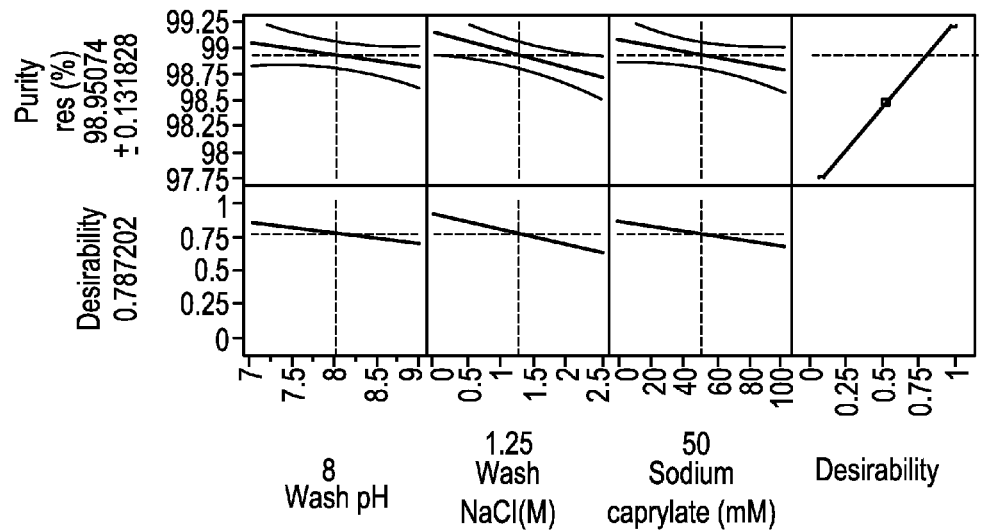

FIG. 12 shows the effect of wash pH, sodium chloride and sodium caprylate on eluate purity.

Figure 14:
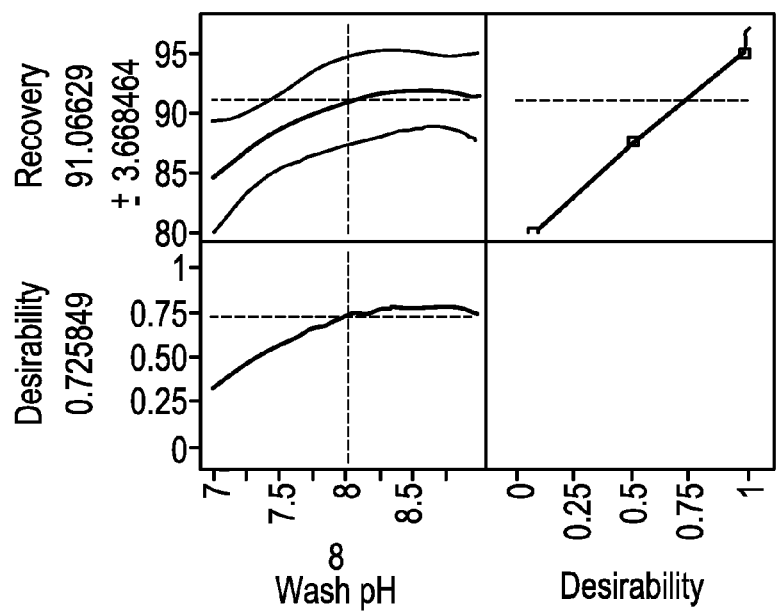

FIG. 13 shows the combined effects of wash pH, sodium chloride and sodium caprylate on purity:

FIG. 14 shows the effect of wash pH on recovery.

Figure 15:
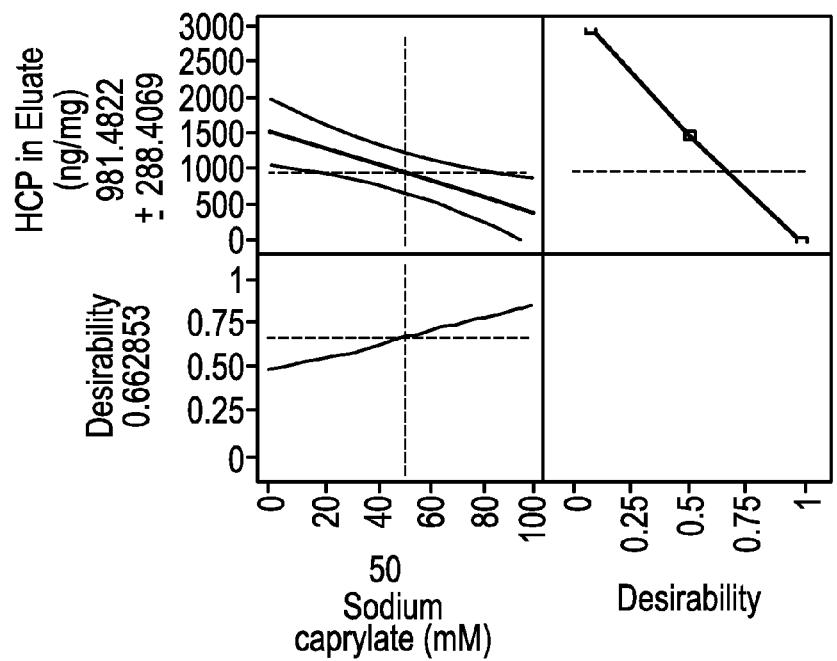

FIG. 15 shows the effect of sodium caprylate on HCP eluate levels.

Figure 16:
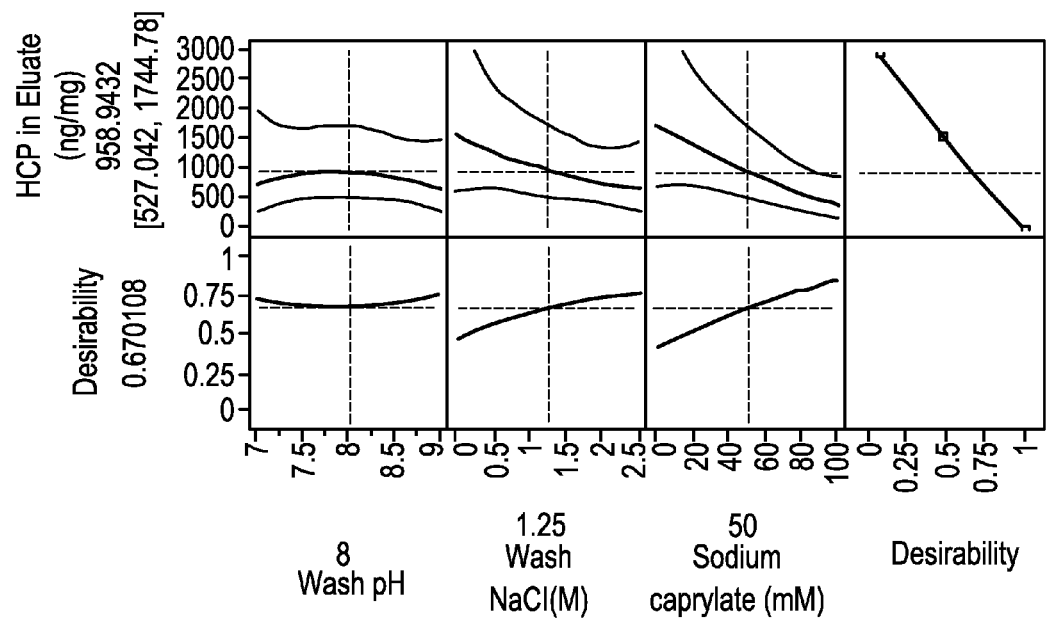

FIG. 16 shows the effects of wash pH, sodium chloride and sodium caprylate on HCP eluate levels.

Figure 17:
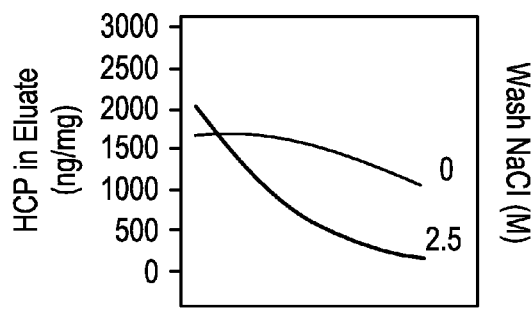

FIG. 17 shows the interaction between sodium chloride and sodium caprylate and the effect of the interaction on HCP eluate levels.

Figure 18:
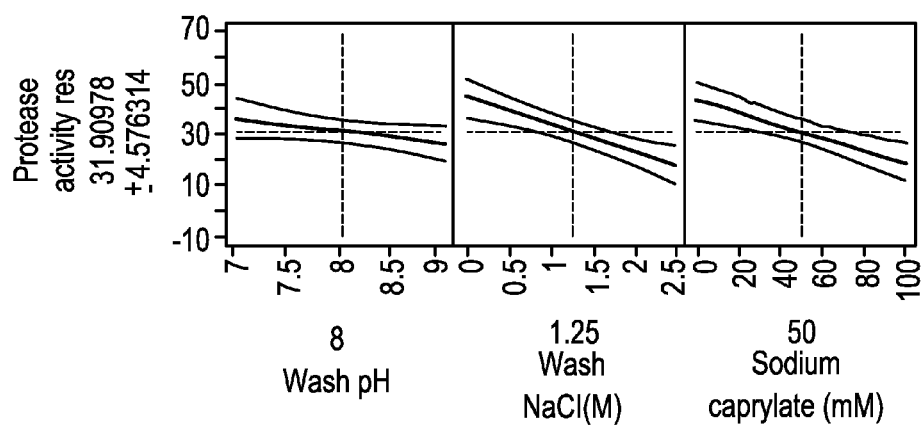

FIG. 18 shows the effect of wash pH, sodium chloride and sodium caprylate on protease activity.

Figure 19:
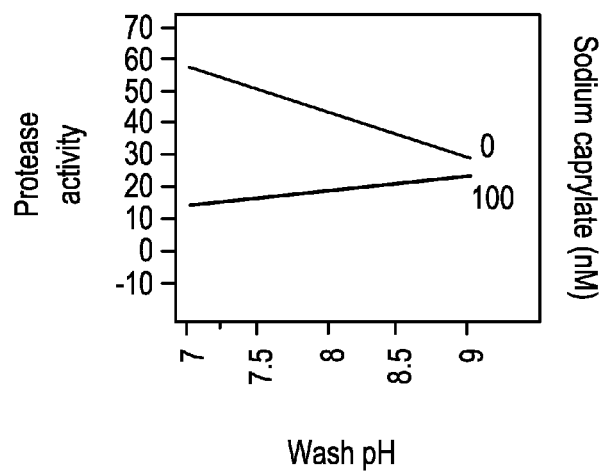

FIG. 19 shows the interaction of wash pH, sodium chloride and sodium caprylate and the effect of the interaction on protease activity.

Figure 20A:
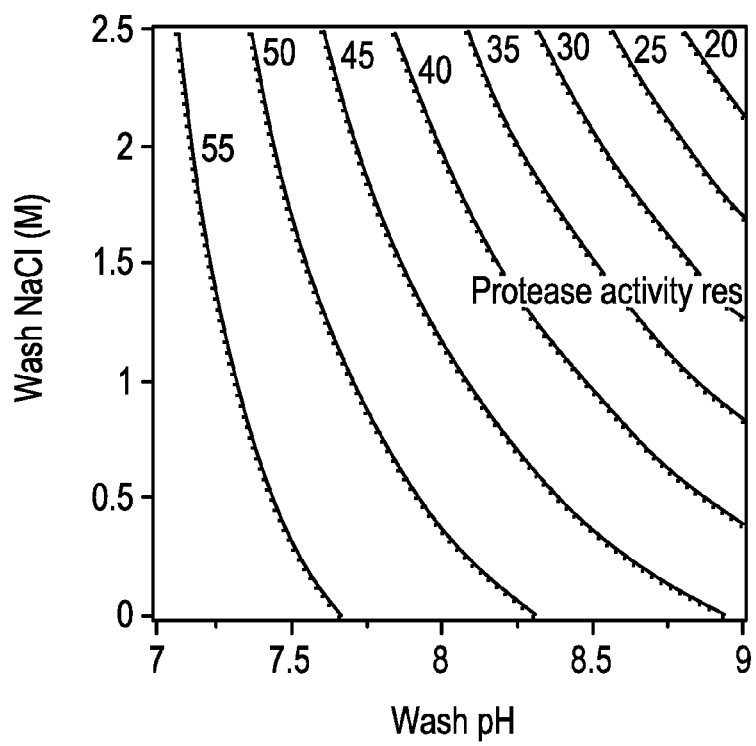

FIGS. 20A and B show the effect of wash pH and sodium chloride on protease activity without (A) and with (B) sodium caprylate.

Figure 21:
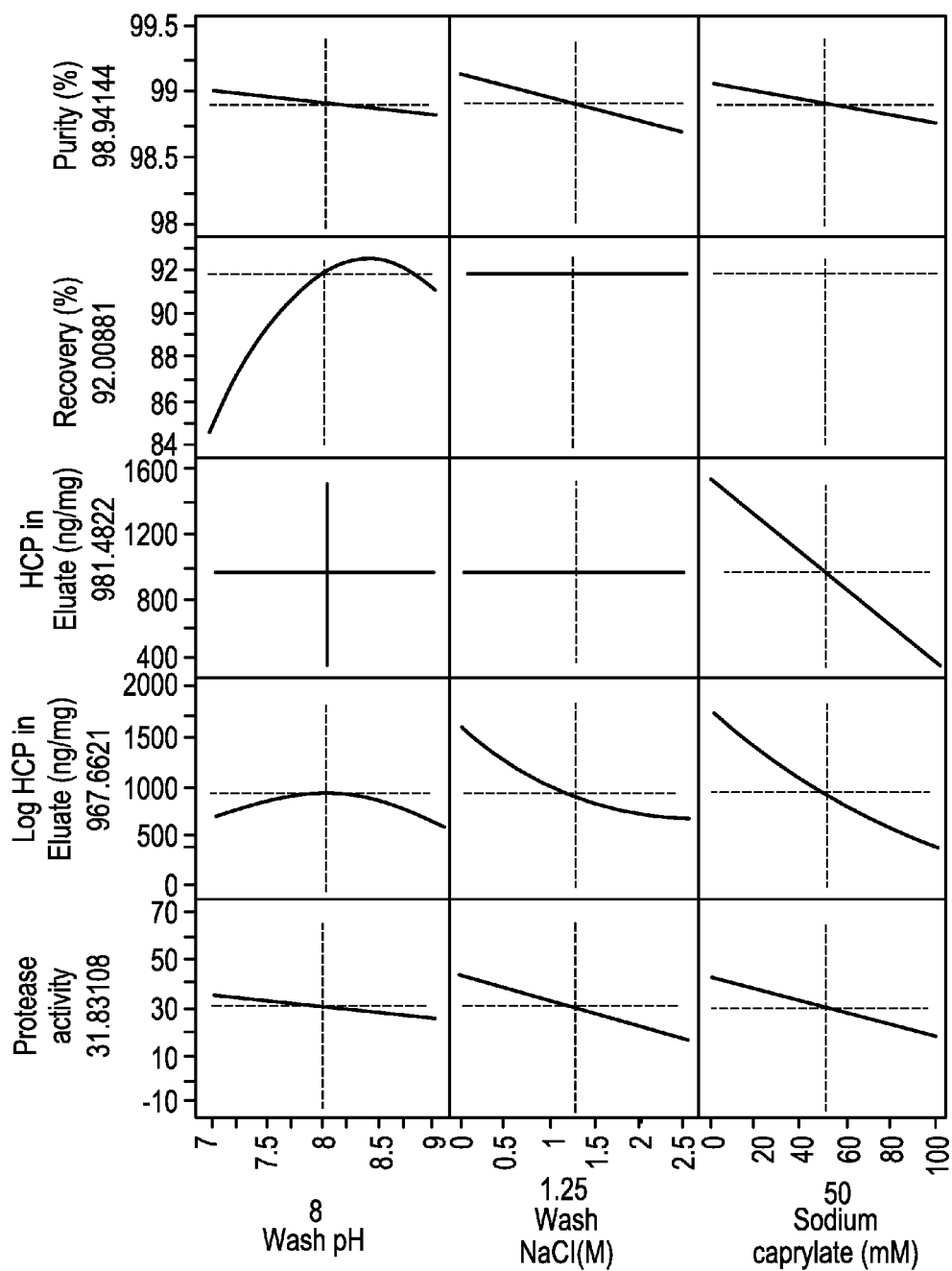

FIG. 21 shows the combined effects of pH, sodium chloride and sodium caprylate on protease activity.

Figure 22:
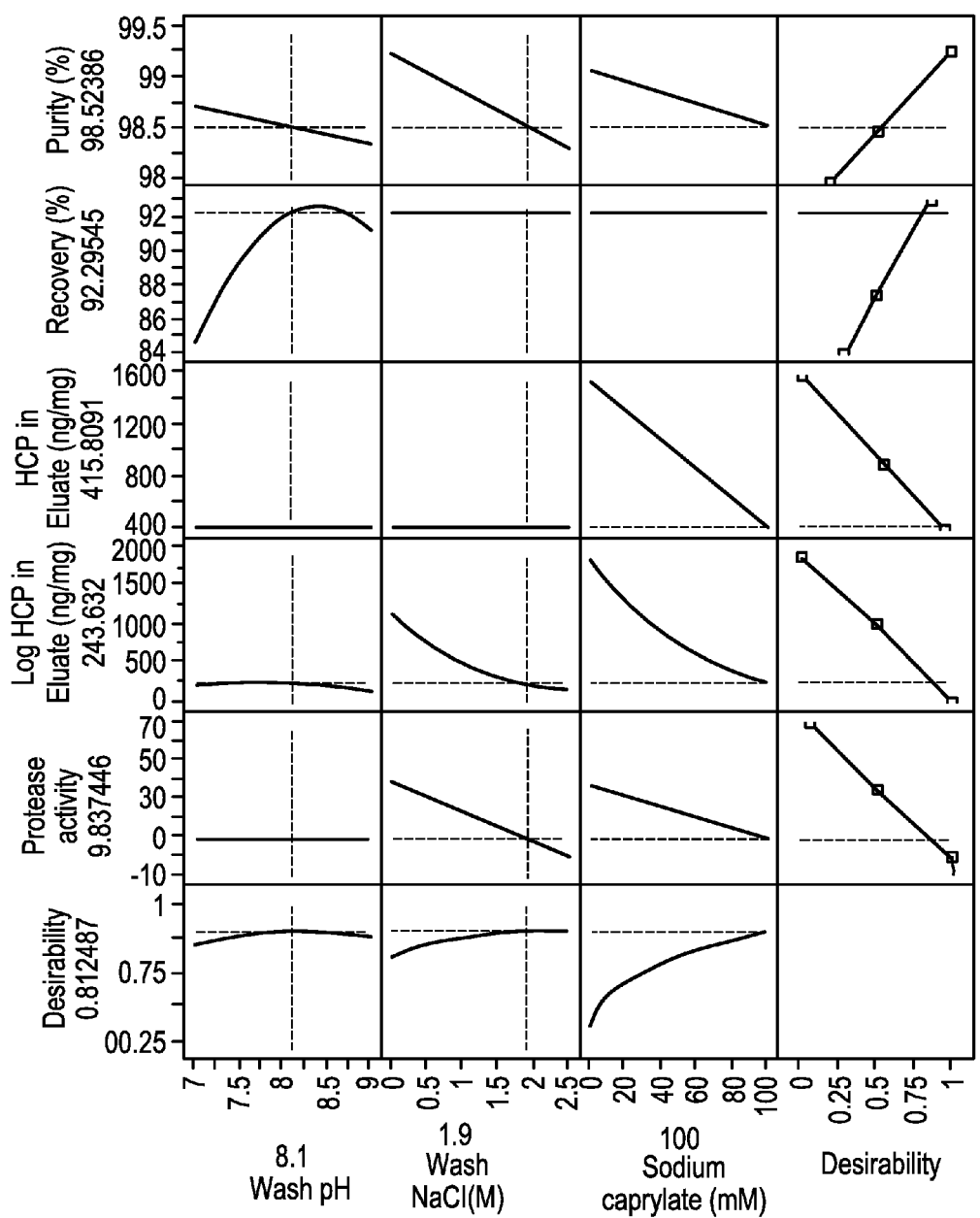

FIG. 22 shows the effect of pH, sodium chloride and sodium caprylate on protease activity.

Figure 23:
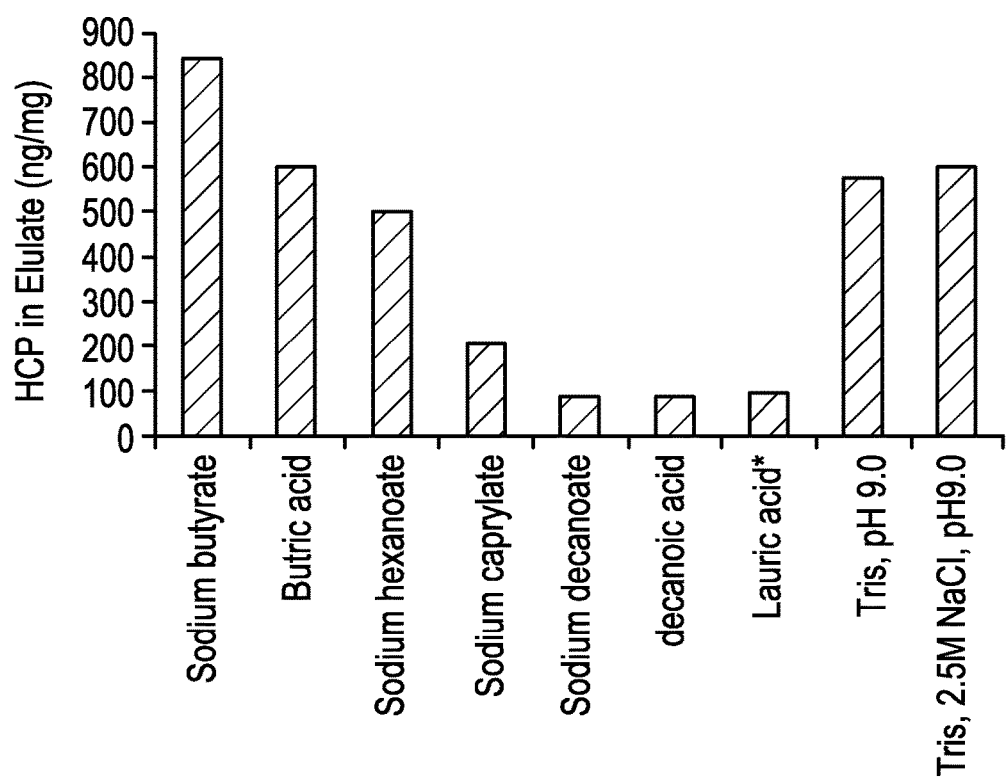

FIG. 23 is a graph showing the HCP levels in anti-IL-18 eluate for the eight fatty acid wash buffer runs in Example 3.

Figure 24:
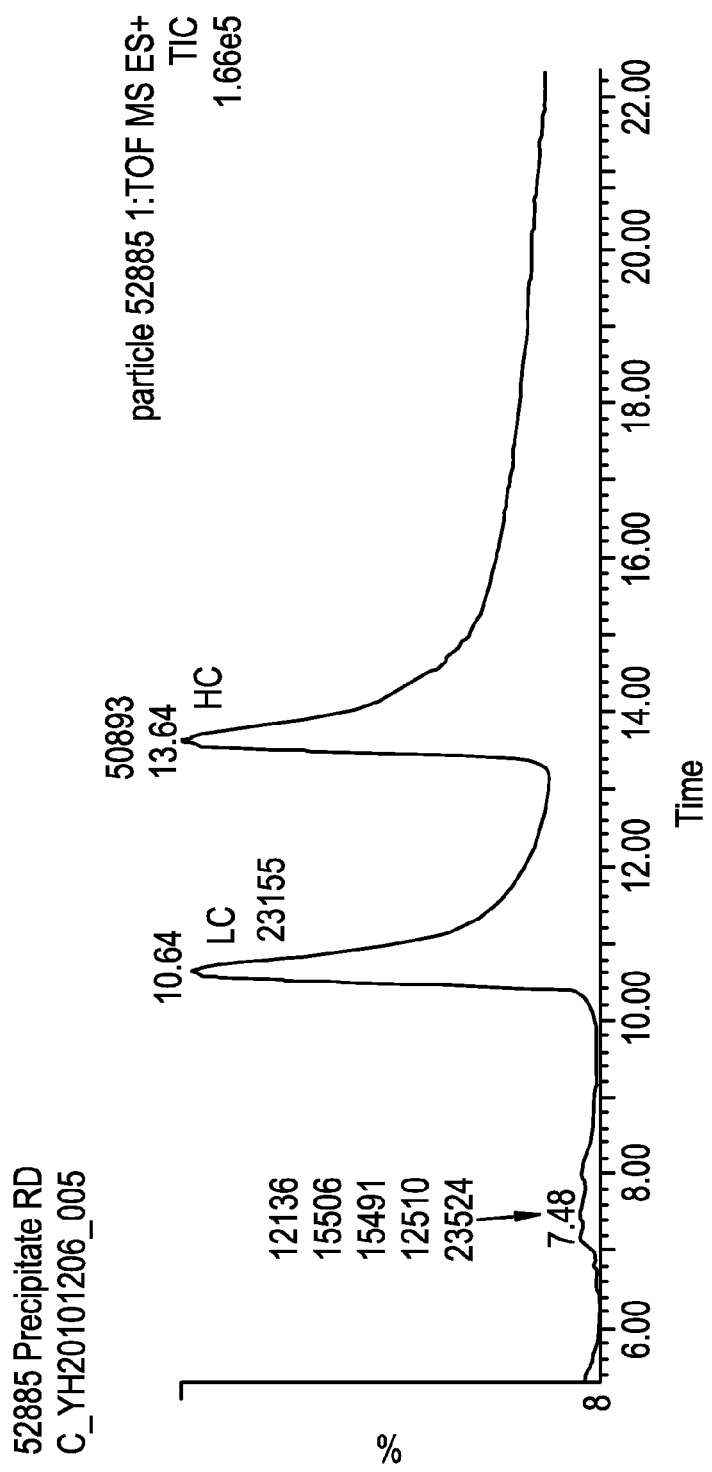

FIG. 24 is a mass spec showing undetectable levels of HCP in pelleted particles containing anti-IL6 antibodies.

Figure 25:
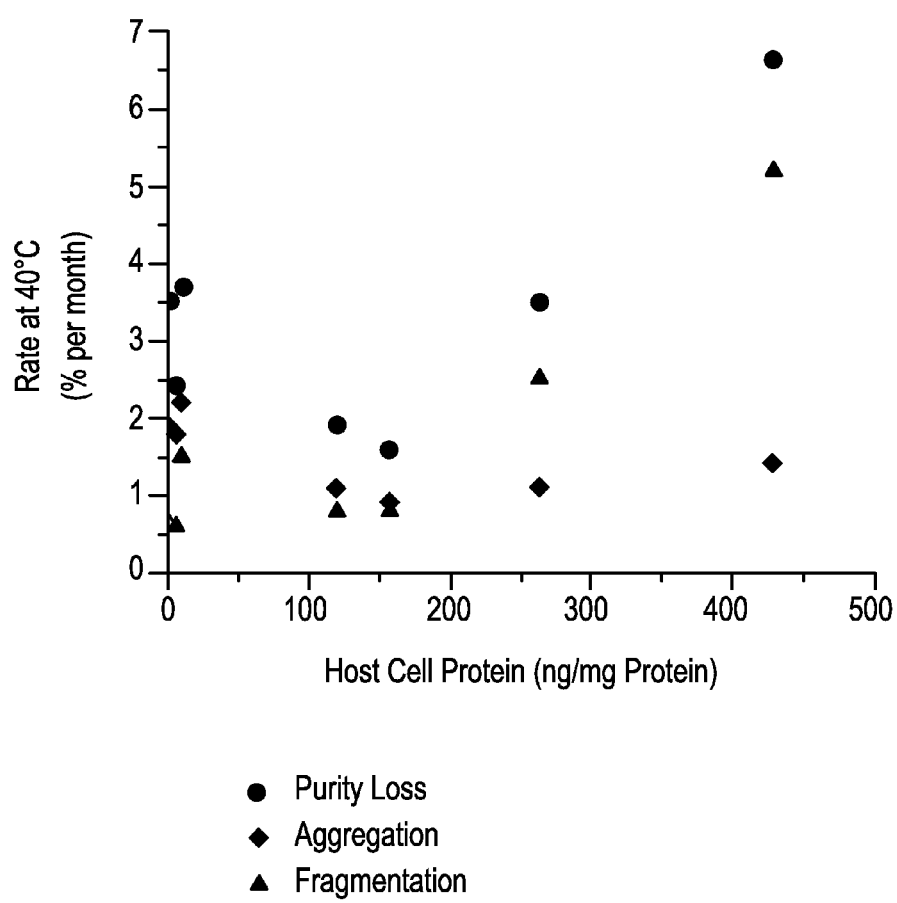

FIG. 25 is a graph showing Rates of Purity Loss, Aggregation, and Fragmentation (measured by SEC) of several lots of anti-IL6 antibodies after storage at 40° C. containing different Host Cell Protein (HCP) levels.

Figure 26:
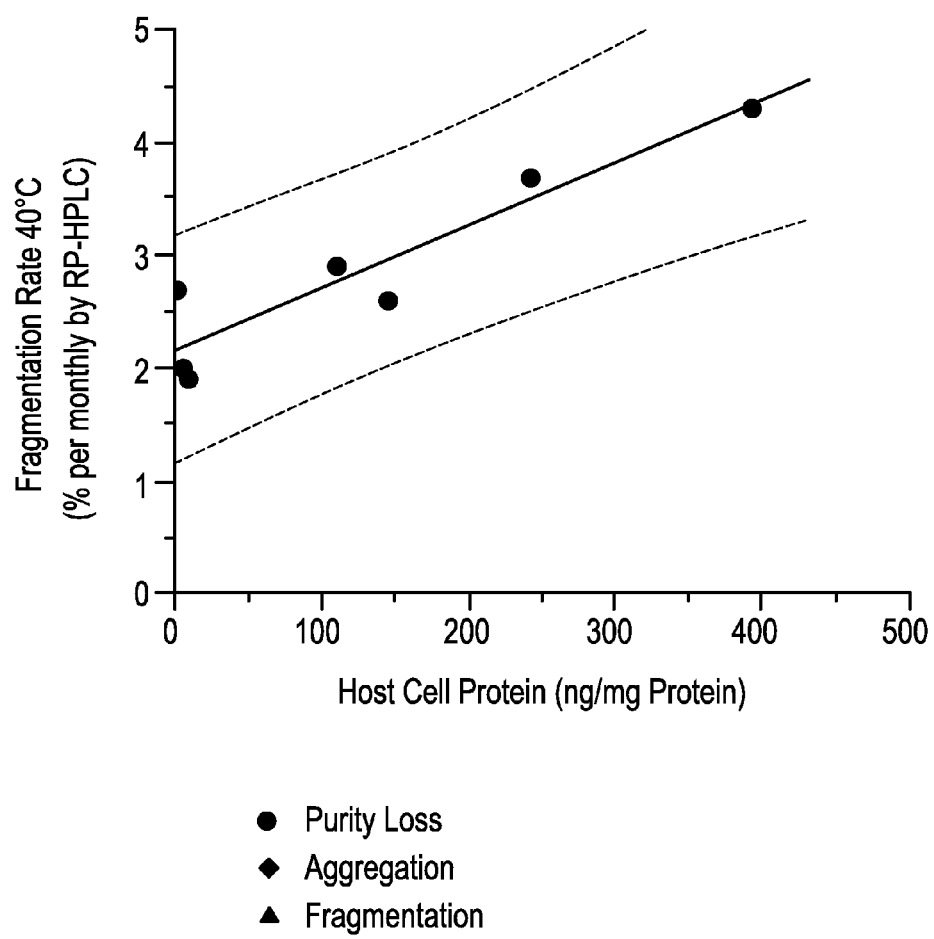

FIG. 26 is a graph showing the effect of HCP on fragmentation rate at 40° C. (by RP-HPLC).

Figure 27:
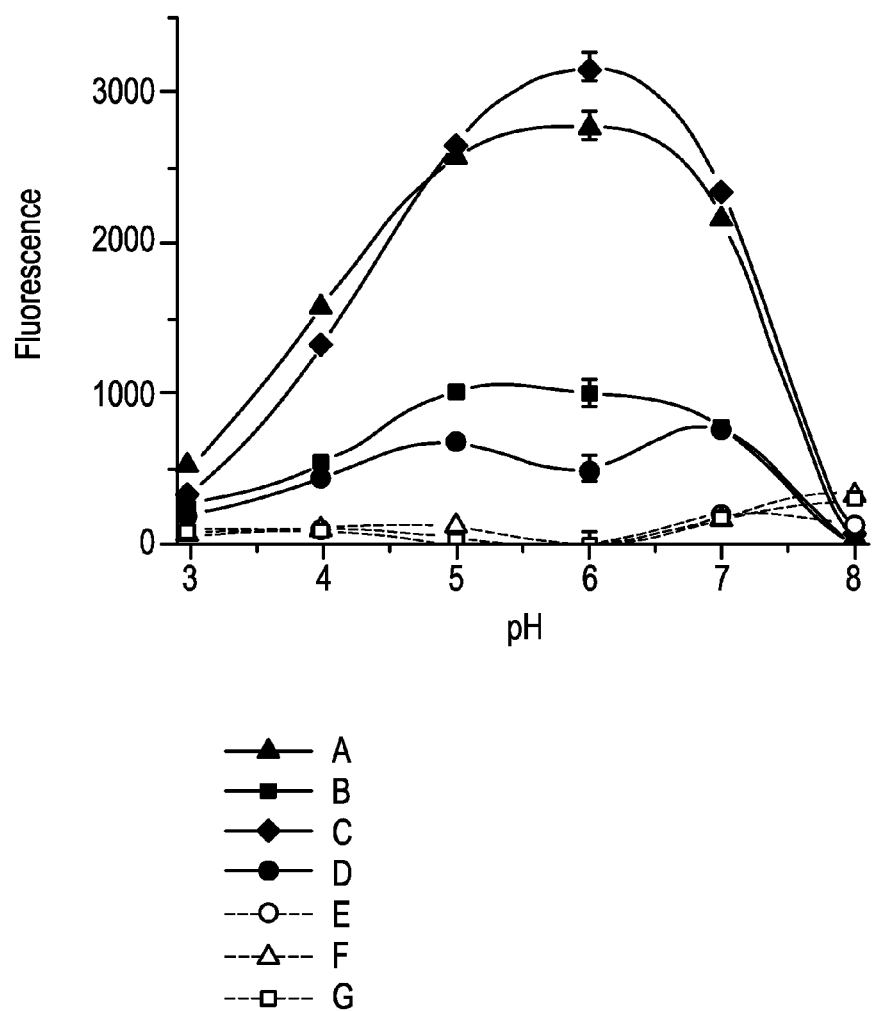

FIG. 27 is a graph showing the effect of caprylate wash on protease activity.

Figure 28:
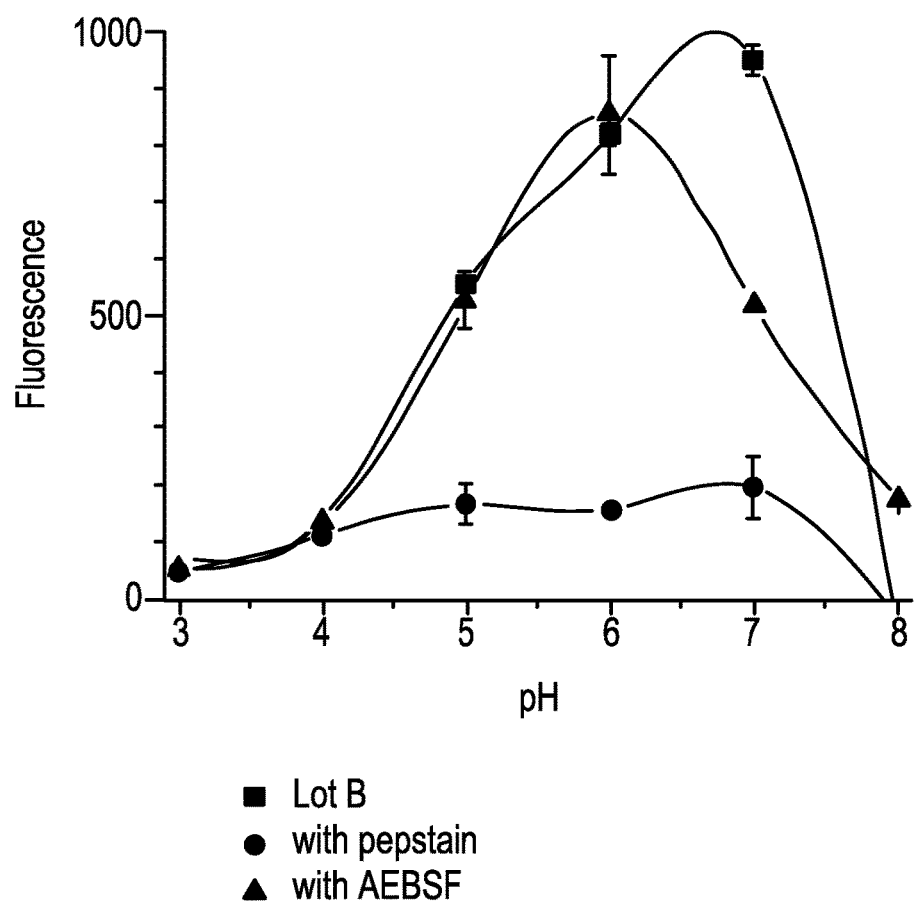

FIG. 28 is a graph showing aspartyl and serine protease activity in a particle forming lot.

4. DETAILED DESCRIPTION

4.1. Introduction

A common problem encountered during Protein A purification is non-specific binding of impurities such as host cell protein (HCP), DNA and other cell culture-derived impurities to the column resin and to the protein of interest. For example, eluate from a Protein A column having large amounts of host cell proteins, for example, up to about 500 ng/mg, 600 ng/mg, 700 ng/mg, 800 ng/mg, 900 ng/mg, 1000 ng/mg, 1500 ng/mg, 2000 ng/mg or more HCP has been observed. The presence of HCP can be problematic, not only because of health regulations relating to acceptable levels of contaminants in recombinant antibody products, but also because the presence of HCP can adversely impact product stability and/or efficacy, including, for example, protease activity and formation of visible particulates, fragments or aggregates over time.

Applicants have found that including a fatty acid in at least one Protein A wash buffer can substantially decrease the level of host cell proteins in the Protein A eluate. In one example, inclusion of a fatty acid in at least one Protein A wash buffer can substantially decrease protease activity in the eluate. Examples of proteases include serine proteases, aspartyl proteases, such as cathepsin-D, cysteine proteases, metalloproteases, aminopeptidases, and combinations thereof. Additionally, including a fatty acid in a Protein A wash buffer can reduce protease activity in a formulation containing a recombinantly produced polypeptide. Furthermore, including a fatty acid in a Protein A wash buffer can increase stability of a recombinantly produced polypeptide, for example, by reducing particle formulation and/or fragmentation.

Described herein is a purification process for recombinantly produced polypeptides. In a more particular embodiment, a purification process for recombinantly produced antibodies is described.

4.2. Terminology

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, and protein and oligo- or polynucleotide chemistry and hybridization described herein are those well-known and commonly used in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used in accordance with the present disclosure, the following terms, unless otherwise indicated, shall be understood to have the following meanings:

As used herein, the term "about" is used to modify, for example, the quantity of an ingredient in a composition, concentration, volume, process temperature, process time, yield, flow rate, pressure, and ranges thereof, employed in describing the invention. The term "about" refers to variation in the numerical quantity that can occur, for example, through typical measuring and handling procedures used for making compounds, compositions, concentrates or formulations; through inadvertent error in these procedures; through differences in the manufacture, source, or purity of starting materials or ingredients used to carry out the methods, and other similar considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include such equivalents.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, with two pairs of polypeptide chains, each pair having one "light" and one "heavy" chain. The variable regions of each light/heavy chain pair form an antibody binding site. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK.

The terms "antibody," "antibodies" and "immunoglobulins" as used herein encompass monoclonal antibodies (including full-length monoclonal antibodies), polyclonal antibodies, multispecific antibodies formed from at least two different epitope binding fragments (e.g., bispecific antibodies), CDR-grafted, human antibodies, humanized antibodies, camelised antibodies, chimeric antibodies, single-chain Fvs (scFv), single-chain antibodies, single domain antibodies, Fab fragments, Fab' fragments, F(ab')$_2$ fragments, antibody fragments that exhibit a desired biological activity (e.g. the antigen binding portion), disulfide-linked Fvs (dsFv), and anti-idiotypic (anti-Id) antibodies, intrabodies, and epitope-binding fragments or derivatives of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1 m (f, z, a or x), G2m (n), G3m (g, b, or c), Am, Em, and Km (1, 2 or 3)). Antibodies may be derived from any mammalian species, including, but not limited to, humans, monkeys, pigs, horses, rabbits, dogs, cats, mice, etc., or other animals such as birds (e.g. chickens). Antibodies may be fused to a heterologous polypeptide sequence, for example, a tag to facilitate purification.

The term "bind" or "binding" when discussing the interaction between a molecule and a column material means exposing the molecule to the column material under conditions such that the molecule is reversibly immobilized in or on the column material.

The term "cell culture supernatant" refers to a solution that is obtained by culturing host cells that produce a recombinant polypeptide of interest. In addition to the recombinant polypeptide, the cell culture supernatant may also include components of cell culture medium, metabolic byproducts secreted by the host cells as well as other components of the cultured cells. As used herein, the term "clarified cell culture supernatant" refers to a composition from which the host cells have been removed or harvested, such that the cell culture supernatant is generally free of cellular debris and/or intact cells.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (for example, but not limited to, serum albumin), amino acids (for example, but not limited to, aspartic acid, glutamic acid, lysine, arginine, glycine), surfactants (for example, but not limited to, SDS, Tween 20, Tween 80, polysorbate and nonionic surfactants), saccharides (for example, but not limited to, glucose, sucrose, maltose and trehalose), polyols (for example, but not limited to, mannitol and sorbitol), fatty acids and phospholipids (for example, but not limited to, alkyl sulfonates and caprylate).

The phrase "host cell" or "host cells" refers to cells which express a recombinant polypeptide. In particular, the term "host cell" refers to a cell that can or has taken up a nucleic acid, such as a vector, and supports replication of the nucleic acid and production of one or more encoded products. The term "host cell" can refer to a variety of cell types including prokaryotic cells, such as *Escherichia coli, Lactococcus lactis* and *Bacillus* species; yeast cells, such as *Pichia pastoris, Pichia methanolica*, and *Saccharomyces cerevisiae*; insect cell, such as bacculovirus and eukaryotic cells. Examples of eukaryotic host cells include mammalian cells, for example, Chinese hamster ovary (CHO) cells, human embryonic kidney (HEK 293) cells, Vero cells, baby hamster kidney (BHK) cells, HeLa cells, CV1 monkey kidney cells, Madin-Darby Canine Kidney (MDCK) cells, 3T3 cells, myeloma cell lines, COS cells (e.g., COS1 and COS7) PC12, W138 cells. The term host cell also encompasses combinations or mixtures of cells including, e.g., mixed cultures of different cell types or cell lines.

The term "impurity" refers to any foreign material, particularly a biological macromolecule such as DNA, RNA, or a protein, other than the recombinantly produced polypeptide that is present in a sample. Contaminants can include host cell proteins other than the recombinant polypeptide of interest.

The term "purify" or "purifying" a recombinant polypeptide from a composition or solution that includes the recombinant polypeptide and one or more contaminants means increasing the degree of purity of the desired protein in the composition or solution by removing (completely or partially) at least one contaminant from the composition or solution.

The term "mAb" refers to a monoclonal antibody.

The phrase "pharmaceutically acceptable" as used herein means approved by a regulatory agency of a Federal or state government, or listed in the U.S. Pharmacopeia, European Pharmacopia or other generally recognized pharmacopeia for use in animals, and more particularly in humans.

The terms "polypeptide" or "protein" can be used interchangeably to refer to a molecule having two or more amino acid residues joined to each other by peptide bonds. The term "polypeptide" can refer to antibodies and other non-antibody proteins. Non-antibody proteins include, but are not limited to, proteins such as enzymes, receptors, ligands of a cell surface protein, secreted proteins and fusion proteins or fragments thereof. The polypeptide may or may not be fused to another polypeptide. Polypeptides can also include modifications such as, but not limited to, glycosylation, lipid attachment, sulfation, gamma-carboxylation of glutamic acid residues, hydroxylation and ADP-ribosylation. Polypeptides can be of scientific or commercial interest, including protein-based therapeutics.

The term "recombinant" refers to a biological material, for example, a nucleic acid or protein, that has been artificially or synthetically (i.e., non-naturally) altered by human intervention.

The term "remove," when used in context of removal of host cell proteins, refers to reduction in the amount of host cell protein in the purified product. Removal may or may not result in the absence of host cell protein from the purified product. In general, removal refers to at least a 2 fold, 3 fold, 4 fold, 5 fold, 10 fold, 15 fold, 20 fold, 25 fold and up to 30 fold, 35 fold, 40 fold, 45 fold or 50 fold reduction in host cell protein in the purified product when compared to the level of host cell proteins in the original composition.

The terms "stability" and "stable" as used herein in the context of a formulation of a recombinantly produced polypeptide, for example, a pharmaceutical formulation that includes a recombinantly produced antibody or antibody fragment, refer to the resistance of the polypeptide in the formulation to particle formation, aggregation, degradation or fragmentation under manufacture, preparation, transportation and storage conditions. A "stable" formulation retains biological activity under manufacture, preparation, transportation and storage conditions. Stability can be assessed by degrees of particle formation, aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, as compared to a reference formulation.

As used herein, "substantially pure" refers to a biological material that is the predominant species present (e.g., on a molar basis it is more abundant than any other individual species in the composition). In one embodiment, a substantially purified fraction is a composition wherein the biological material includes at least about 50% (on a molar basis) of all macromolecular species present. Generally, a substantially pure composition will include more than about 80% of all macromolecular species present in the composition, or more than about 85%, more than about 90%, more than about 95%, or more than about 99%. In one embodiment, the biological material is purified to essential homogeneity (contaminant species cannot be detected in the composition by conventional detection methods) and the composition includes essentially a single macromolecular species.

4.3. Recombinant Polypeptide Production

In one embodiment, a recombinant polypeptide is produced using host cells that have been transfected, either stably or transiently, with a vector capable of expressing one or more polypeptides of interest. As used herein, the term "vector" refers to composition of matter which can be used to deliver a nucleic acid of interest to the interior of a cell. Numerous vectors are known including, but not limited to, linear polynucleotides, polynucleotides associated with ionic or amphiphilic compounds, plasmids, and viruses. The term "vector" can include an autonomously replicating plasmid or a virus or a vector or plasmid that is not autonomously replicating. The term "transfection" refers to the introduction of exogenous genetic material into cells to produce genetically modified cells. Vectors can be introduced into a host cell using methods known in the art. For example, a vector can be transferred into a host cell by physical, chemical or biological means. Physical methods for introducing a polynucleotide into a host cell include, but are not limited to, calcium phosphate precipitation, lipofection (including positively charged liposome mediated transfection), particle bombardment, microinjection, DEAE-dextran mediated transfection and electroporation. Biological methods for introducing a vector into a host cell include the use of DNA and RNA vectors, including, for example, viral vectors, Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. The host cells can be genetically engineered to express a recombinant polypeptide, for example, a polypeptide of commercial or scientific interest.

The term "cell culture" refers to the growth and propagation of cells outside of a multicellular organism or tissue. Cell culture conditions such as pH, temperature, humidity, atmosphere and agitation can be varied to improve growth and/or productivity characteristics of the cell culture. Host cells may be cultured in suspension or while attached to a solid substrate. Host cells can be cultured in small scale cultures, for example, in a laboratory setting at volumes as low as 25 ml and up to about 50 ml, up to about 100 ml, up to about 150 ml or up to about 200 ml. Alternatively, the cultures can be large scale, for example, at volumes from about 300 ml, 500 ml or 1000 ml and up to about 5000 ml, up to about 10,000 ml and up to about 15,000 ml. Commercial scale bioreactors can also be used, for example, at volumes of up to about 1,000 L, up to about 5,000 L or up to about 10,000 L of media. Large scale production of recombinant polypeptides by mammalian cells can include continuous, batch and fed-batch culture systems. Host cells may be cultured, for example, in fluidized bed bioreactors, hollow fiber bioreactors, roller bottles, shake flasks, or stirred tank bioreactors, with or without microcarriers, and operated in a batch, fed batch, continuous, semi-continuous, or perfusion mode. Large scale cell cultures are typically maintained for days, or even weeks, while the cells produce the desired protein product(s).

Suitable host cells for production of recombinant polypeptides include both prokaryotic and eukaryotic cells. Examples of eukaryotic cells include mammalian cells. Examples of mammalian cells suitable for production of recombinant polypeptides include, but are not limited to, Chinese hamster ovary (CHO) cells, mouse myeloma (NS0), human embryonic kidney (HEK 293), baby hamster kidney (BHK) cells, Vero cells, HeLa cells, Madin-Darby Canine Kidney (MDCK) cells, CV1 monkey kidney cells, 3T3 cells, myeloma cell lines such as NS0 and NS1, PC12, W138 cells, COS cells (including COS-1 and COS-7), and C127. In general, mammalian cell cultures are maintained at a pH between about 6.5 and about 7.5 and at a temperature between about 36° C. and about 38° C., typically at abut 37° C. and a relative humidity between about 80% and about 95%. Mammalian cell culture media typically contain buffering systems that require a carbon dioxide ($CO_2$) atmosphere between about 1% and about 10%, or between about 5% and about 6%.

The host cells can be maintained in a variety of cell culture media. The term "cell culture medium" refers to a nutrient solution in which the host cells are grown. Cell culture media formulations are well known in the art. Typically, cell culture media include buffers, salts, carbohydrates, amino acids, vitamins and trace essential elements. The cell culture medium may or may not contain serum, peptone, and/or proteins. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters. Various culture media, including serum-free and defined culture media, are commercially available, and include, but are not limited to, Minimal Essential Medium (MEM, Sigma, St. Louis, Mo.); Ham's F10 Medium (Sigma); Dulbecco's Modified Eagles Medium (DMEM, Sigma); Minimal Essential Medium (MEM); Basal Medium Eagle (BME); RPMI-1640 Medium (Sigma); HyClone cell culture medium (HyClone, Logan, Utah); and chemically-defined (CD) media, which are formulated for particular cell types, e.g., CD-CHO Medium (Invitrogen, Carlsbad, Calif.). Supplementary components or ingredients can be added to commercially available media, if desired.

The term "recombinant polypeptide" as used herein refers to a genetically engineered polypeptide or protein produced by a cultured host cell. As used herein, the term "heterologous" refers to a recombinant polypeptide that is produced by a host cell that does not normally express that polypeptide. However, a heterologous polypeptide can include polypeptides that are native to an organism, but that have been intentionally altered in some manner. For example, a heterologous polypeptide can include a polypeptide that is expressed by a host cell that has been transfected with a vector that expresses the polypeptide. The recombinant polypeptides expressed by the cell culture may be produced intracellularly or be secreted into the culture medium from which they can be recovered and/or collected.

In one embodiment, the recombinant polypeptide is an antibody or binding fragment thereof. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', $F(ab')_2$ single stranded antibody (svFC), dimeric variable region (Diabody) and disulphide-linked variable region (dsFv). Immunoglobulin molecules can be of any type (e.g., IgG, IgE, IgM, IgD, IgA and IgY), class (e.g., IgG1, IgG2, IgG3, IgG4, IgA1 and IgA2) or subclass. In one embodiment, the antibody or antigen binding fragment thereof may be fused to a heterologous polypeptide sequence, such as an affinity tag, to facilitate purification. Examples of affinity tags include, but are not limited to, polyhistidine tags, GFP tags, FLAG tags, GST tags, V5 tags and Myc tags.

In one embodiment, the antibody is an anti-IL-18 antibody or an anti-IL6 antibody, or a fragment thereof. In other embodiments, the antibody can be any antibody that co-purifies with a host cell protein.

In another embodiment, the recombinantly produced polypeptide includes an antibody having a light chain acid variable sequence of antibody 1 (SEQ ID NO:8). In another embodiment, the recombinantly produced polypeptide includes an antibody having a heavy chain variable sequence of antibody 1 (SEQ ID NO:7). In another embodiment, the recombinantly produced polypeptide includes an antibody having a light chain variable sequence of antibody 1 (SEQ ID NO: 8) and a heavy chain variable sequence of antibody 1 (SEQ ID NO:7).

In another embodiment, the recombinantly produced polypeptide includes an antibody having a light chain acid variable sequence of antibody 2 (SEQ ID NO:18). In another embodiment, the recombinantly produced polypeptide includes an antibody having a heavy chain variable sequence of antibody 2 (SEQ ID NO.16). In another embodiment, the recombinantly produced polypeptide includes an antibody having a light chain variable sequence of antibody 2 (SEQ ID NO: 18) and a heavy chain variable sequence of antibody 2 (SEQ ID No.:16).

In one embodiment, the antibody includes a heavy chain amino acid sequence having one or more complementarity determining regions (CDRs) of antibody 1 or antibody 2. The terms CDR region or CDR, refer to the hypervariable regions of the heavy and light chains of the immunoglobulin as defined by Kabat et al. (Kabat, E. A. et al. (1991) Sequences of Proteins of Immunological Interest, 5th Edition. US Department of Health and Human Services, Public Service, NIH, Washington or later editions) or Chothia and Lesk (J. Mol. Biol., 196:901-917 (1987)). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes. Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody. One of skill in the art is able to determine CDR regions of an antibody. In general, HCDR1 is about 5 amino acids long, consisting of Kabat residues 31-35; HCDR2 is about 17 amino acids long, consisting of Kabat residues 50-65; HCDR3 is about 11 or 12 amino acids long, consisting of Kabat residues 95-102, optionally including Kabat residue 100D; LCDR1 is about 11 amino acids long, consisting of Kabat residues 24-34; LCDR2 is about 7 amino acids long, consisting of Kabat residues 50-56; and LCDR3 is about 8 or 9 amino acids long, consisting of Kabat residues 89-97, optionally including Kabat residue 95.

In one embodiment, the recombinantly produced polypeptide is an antibody or binding fragment thereof that includes a light chain amino acid sequence that includes one or more light chain CDR sequences for antibody 1 selected from LCDR1 (SEQ ID NO:4); LCDR2 (SEQ ID NO: 5); LCDR3 (SEQ ID NO:6), and combinations thereof. In one embodiment, the recombinantly produced polypeptide is an antibody that includes a heavy chain amino acid sequence that includes one or more of the heavy chain CDR sequences for antibody 1 selected from HCDR1 (SEQ ID NO: 1); HCDR2 (SEQ ID NO: 2), HCDR3 (SEQ ID NO:3), and combinations thereof. In one embodiment, the recombinantly produced polypeptide is an antibody or binding fragment thereof that includes a light chain amino acid sequence that includes LCDR1 (SEQ ID NO:4); LCDR2 (SEQ ID NO: 5), and LCDR3 (SEQ ID NO:6) from antibody 1 and a heavy chain amino acid sequence that includes HCDR1 (SEQ ID NO: 1); HCDR2 (SEQ ID NO: 2) and HCDR3 (SEQ ID NO:3) of antibody 1.

In one embodiment, the recombinantly produced polypeptide is an antibody or binding fragment thereof that includes a light chain amino acid sequence that includes one or more light chain CDR sequences for antibody 2 selected from LCDR1 (SEQ ID NO:12); LCDR2 (SEQ ID NO: 13), LCDR3 (SEQ ID NO:14), and combinations thereof. In one embodiment, the recombinantly produced polypeptide is an antibody that includes a heavy chain amino acid sequence having one or more of the heavy chain CDR sequences for antibody 2 selected from HCDR1 (SEQ ID NO: 9); HCDR2 (SEQ ID NO: 10), HCDR3 (SEQ ID NO: 11), and combinations thereof. In one embodiment, the recombinantly produced polypeptide is an antibody or binding fragment thereof that includes a light chain amino acid sequence that includes LCDR1 (SEQ ID NO: 12); LCDR2 (SEQ ID NO: 13), and LCDR3 (SEQ ID NO: 14) from antibody 2 and a heavy chain amino acid sequence that includes HCDR1 (SEQ ID NO: 9); HCDR2 (SEQ ID NO: 10) and HCDR3 (SEQ ID NO: 11) of antibody 2.

4.4 Purification

The first step in the recovery of a recombinantly produced polypeptide (also referred to herein as a "target polypeptide" or "target") from a cell culture is the removal of intact host cells and host cell debris from the culture media, referred to as "harvesting," to yield a clarified cell culture supernatant that contains the recombinantly produced polypeptide along with other remaining impurities. Harvesting is generally accomplished by centrifugation, flocculation/precipitation, depth filtration and sterile filtration, although other approaches can be used.

Recombinantly produced antibodies can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. When the antibody is secreted into the medium, supernatants from the expression system can be concentrated, for example, using a commercially available protein concentration filter, such as an Amicon or Millipore Pellicon ultrafiltration unit. A protease inhibitor or protease inhibitor cocktail that includes one or more protease inhibitor such as bestatin, aprotinin, pepstatin, leupeptin, 4-(2-Aminoethyl)benzenesulfonyl fluoride hydrochloride (AEBSF), pr phenylmethanesulfonylfluoride (PMSF) may be included to inhibit proteolysis. In other embodiments, one or more antibiotics may be included to prevent the growth of adventitious contaminants. Examples of suitable antibiotics include, but are not limited to, actinomycin D, ampicillin, carbenicillin, cefotaxime, fosmidomycin, gentamicin, kanamycin, neomycin, penicillin, polymyxin B, and streptomycin.

After the clarified cell culture supernatant has been obtained, the target polypeptide can be further purified by removal of other impurities in the cell culture supernatant that may include, but are not limited to, host cell proteins (HCP), DNA, adventitious and endogenous viruses, endotoxin, aggregates and other species. Most purification methods involve some form of chromatography in which target molecules in solution (mobile phase) are separated based on a difference in chemical or physical interaction with a stationary material (solid phase). General chromatographic methods and their use are known to persons skilled in the art. See for example, Sambrook, J., et al. (eds.), Molecular Cloning: A Laboratory Manual, Second Edition, Cold Spring Harbor Laboratory Press, Cold Spring Harbor, N.Y., 1989. Many different methods for recombinant polypeptide purification are known, and include, but are not limited to affinity chromatography, ion exchange chromatography, hydrophobic interaction chromatography, hydroxylapatite chromatography, size exclusion chromatography, gel electrophoresis, dialysis and combinations thereof. Other techniques for protein purification such as fractionation on an ion-exchange column, ethanol precipitation, isoeletric focusing, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation can also be included in the purification process. Often, a combination of different purification processes are used, such that the different processes separate the polypeptide based on different principles, such as affinity, charge, degree of hydrophobicity, and/or size. Many different chromatography resins are available for each technique, such that a purification scheme can be tailored to the particular recombinant polypeptide. Column chromatography can be performed with automated systems, such as the GE Healthcare AKTA AVANT system, which use a pump to force solvent over a packed column at a set flow rate, or can be run by gravity flow. Both automated and gravity flow systems can be coupled to automatic fraction collecting systems.

Figure 1:
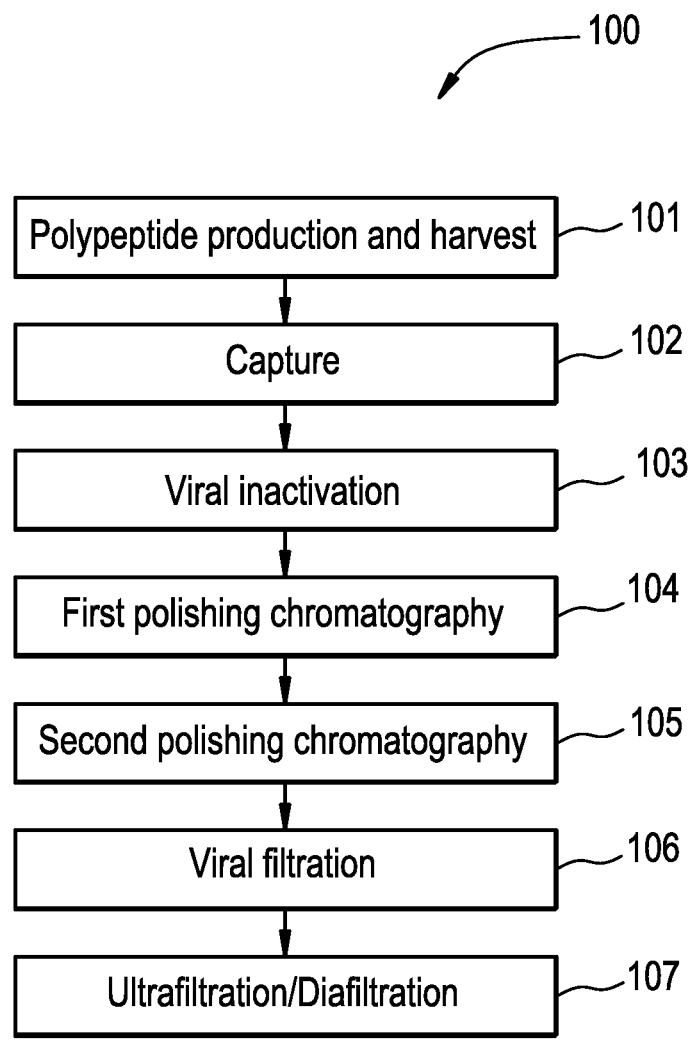
FIG. 1 is a flow chart of a sample purification process.

In one embodiment, a combination of purification processes is employed as a purification scheme. One example of purification scheme 100 is shown as a flow chart in FIG. 1. The sample purification scheme 100 includes a first step in which the recombinant polypeptide is produced, for example, by expression in a host cell and harvested 101. Methods for recombinant polypeptide production and harvesting are discussed above. The recombinant polypeptide is then captured 102, for example, using affinity chromatography. In one embodiment, the recombinant polypeptide is an antibody and Protein A affinity chromatography is used for capture 102. The purification process can also include one or more polishing chromatography steps 104, 105. To improve viral clearance, a viral inactivation step 103 and/or a viral filtration step 106 may also be included in the purification scheme 100. Lastly, the purified product can be concentrated and diafiltered into a final formulation buffer 107. It is noted that the scheme provided in FIG. 1 is merely an example, and variations, for example, in the order of steps, number of steps, and purification methods used for each step, are well within the abilities of one of skill in the art.

In one embodiment, capture 102 is accomplished by affinity chromatography. Affinity chromatography refers to a chromatographic method in which a biomolecule such as a recombinantly produced polypeptide is separated based on a specific reversible interaction between the polypeptide and a binding partner covalently coupled to the solid phase. Examples of affinity interactions include, but are not limited to the reversible interaction between an antigen and antibody, enzyme and substrate, or receptor and ligand. In one embodiment, affinity chromatography involves the use of microbial proteins, such as Protein A or Protein G. Protein A is a bacterial cell wall protein that binds to mammalian IgGs primarily through their Fc regions. Protein A resin is useful for affinity purification and isolation of a variety antibody isotypes, particularly $IgG_1$, $IgG_2$, and $IgG_4$. There are many Protein A resins available that are suitable for use in the purification process described herein. The resins are generally classified based on their backbone composition and include, for example, glass or silica-based resins; agarose-based resins; and organic polymer based resins.

In one embodiment, Protein A affinity chromatography is used to capture a recombinantly produced antibody. The flow rate through an affinity chromatography support is an important parameter for optimizing separation. Although a reduced separation time may be desirable, a flow rate that is too fast a flow may cause the mobile phase to move past the solid phase faster than the diffusion time necessary to reach the internal bead volume. Generally, a flow rate of at least about 50 cm/h, 100 cm/h, 150 cm/h, 200 cm/hour or 250 cm/hour and up to about 300 cm/hour, 350 cm/hour, 400 cm/hour, 450 cm/hour or 500 cm/hr is used. The column dimensions can also be varied. While laboratory bench scale columns generally have a column diameter of less than 1 cm, or less than 5 cm, large scale or commercial production scales can use columns having diameters of up to 1 meter or even up to 2 meters. For large scale or commercial production, the column bed height is generally at least about 10 cm, 15 cm or 20 cm, and up to about 25 cm or 30 cm.

The composition of the buffer solutions and the volume of buffer solutions used in connection with Protein A purification can be varied. The term "buffer" or "buffered solution" refers to a solution that is able to resist changes in pH. Often a buffer is made of a weak conjugate acid-base pair, for example, a weak acid and its conjugate base or a weak base and its conjugate acid. In some buffers, the buffering agent is supplied as a crystalline acid or base, for example, Tris is supplied as a crystalline base, which is dissolved in water to form a buffering solution. The pH of the buffering solution can be adjusted using an appropriate acid or base. For example, hydrochloric acid (HCl) can be used to adjust the pH of a Tris buffering solution. Other buffers are prepared by mixing two components, such as a free acid or base and a corresponding salt, in ratios that achieve the desired pH. For example, a sodium citrate buffer solution can be made and adjusted to the desired pH by combining citric acid and trisodium citrate to form a solution with the desired pH. Other buffers are made by mixing a buffer component and its conjugate acid or base. For example, a phosphate buffer can be made by mixing monobasic and dibasic sodium phosphate solutions in a ratio to achieve a desired pH. In another embodiment, a sodium bicarbonate buffer system can be prepared by combining solutions of sodium carbonate and sodium bicarbonate to form a buffer solution having a desired pH.

In one embodiment, the column is equilibrated with an "equilibration buffer" prior to loading. The term "equilibration buffer" refers to a buffer that can be used to remove undesired residual from the column matrix and to prepare the solid phase of the column matrix for loading the target protein, for example, by adjusting the pH of the column. When used for antibody purification, the pH of the equilibration buffer is at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0. In one embodiment, the equilibration buffer includes a buffering agent such as tris(hydroxymethyl)aminomethane (often referred to as "Tris") (pH range 5.8-8.0), 4-(2-hydroxyethyl)-1-piperazineethanesulfonic acid (HEPES) (pH range 6.8-8.2), 3-(N-morpholino)propanesulfonic acid (MOPS) (pH range 6.5-7.9) or other phosphate buffering agents (pH 5.8-8.0) at a concentration of at least about 10 mM, 25 mM, 50 mM or 75 mM and up to about 100 mM, 125 mM or 150 mM. In one embodiment, the pH of the buffering solution can be adjusted using an appropriate acid or base, such as hydrochloric acid (HCl) or sodium hydroxide/potassium hydroxide (NaOH/KOH). In one embodiment, the equilibration buffer includes at least about 10 mM, 15 mM, or 20 mM and up to about 25 mM, 30 mM, 50 mM or 100 mM sodium phosphate at a pH of at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0. Additionally, the buffer may include one or more additives to increase protein purity, stability, and function, including, but not limited to reducing agents such as 2-mercaptoethanol (BME), dithiothreitol (DDT) or Tris(2-carboxyethyl)phosphine (TCEP) to protect against oxidative damage, protease inhibitors, including but not limited to leupeptin, pepstatin A and phenylmethanesulfonylfluoride (PMSF) to inhibit endogenous proteases from degrading the target polypeptide, metal chelators, including but not limited to ethylenediaminetetraacetic acid (EDTA) and ethylene glycol tetraacetic acid (EGTA), to inactivate metalloproteases, osmolytes, including but not limited to glycerol, detergents and sugars to stabilize protein structure or ionic stabilizers, including but not limited to salts such as NaCl, KCl and $(NH_4)_2SO_4$ to enhance solubility. In one embodiment, the column is equilibrated using at least about 5, and up to about 10 or 20 column volumes of the equilibration buffer prior to loading the recombinantly produced polypeptide onto the column.

In one embodiment, a clarified cell culture supernatant is loaded onto the column. In one embodiment, the clarified cell culture supernatant is loaded onto the column after the column has been equilibrated with an equilibration buffer. In a further embodiment, the clarified cell culture supernatant is loaded onto the column in combination with a loading buffer. The term "loading buffer" refers to a buffer that is combined with a composition that includes the target polypeptide prior to loading the target onto a column. In general, the target polypeptide is loaded at a concentration of at least about 1 mg/ml, 5 mg/ml, 10 mg/ml, 15 mg/ml, 20 mg/ml or 25 mg/ml and up to about 30 mg/ml, 35 mg/ml, 40 mg/ml, 45 mg/ml, 50 mg/ml, 75 mg/ml or 100 mg/ml. In one embodiment, clarified cell culture supernatant is diluted with a loading buffer at a ratio of about 1:1, 1:2 or 1:3, for example, to achieve a desired concentration for the target polypeptide and/or to adjust the pH of the solution. In other embodiments, the clarified cell culture supernatant is loaded directly onto the column (i.e., the supernatant is not diluted with a loading buffer). In one embodiment, the column is re-equilibrated with an equilibration buffer after the clarified cell culture supernatant has been loaded. In a more particular embodiment, the column is re-equilibrated with at least about 5 and up to about 10 or 20 column volumes of the equilibration buffer or loading buffer after the target polypeptide is loaded onto the column. In general, the target polypeptide is loaded onto the Protein A column at a pH of at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0. In some embodiments, the loading buffer is the same as the equilibration buffer. In other embodiments, the loading buffer and the equilibration buffer are not the same. In other embodiments, the loading buffer is also used as a wash buffer to wash the column after loading.

In one embodiment, the loading buffer includes a buffering agent such as tris(hydroxymethyl)aminomethane (often referred to as "Tris") (pH range 5.8-8.0), 4-(2-hydroxyethyl)-1-piperazineethanesulfonic acid (HEPES) (pH range 6.8-8.2), 3-(N-morpholino)propanesuifonic acid (MOPS) (pH range 6.5-7.9) or other phosphate buffering agents, such as sodium phosphate or phosphate-citrate buffers (pH 5.8-8.0) at a concentration of at least about 10 mM, 20 mM, 30 mM, 40 mM or 50 mM and up to about 60 mM, 70 mM, 80 mM, 90 mM, or 100 mM. In one embodiment, the pH of the buffering solution can be adjusted using an appropriate acid or base, such as hydrochloric acid (HCl) or sodium hydroxide/potassium hydroxide (NaOH/KOH). When used for antibody purification, the pH of the loading buffer is generally adjusted to at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0. In a more particular embodiment, the loading buffer includes at least about 10 mM, 15 mM or 20 mM and up to about 25 mM, 30 mM, 50 mM or 100 mM sodium phosphate at has a pH of at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0. In one embodiment, the column is re-equilibrated after loading using at least about 5, and up to about 10 or 20 column volumes of the equilibration or loading buffer. Additionally, the equilibration buffer may include one or more additives to increase protein purity, stability, and function, including, but not limited to reducing agents such as 2-mercaptoethanol (BME), dithiothreitol (DDT) or Tris (2-carboxyethyl)phosphine (TCEP) to protect against oxidative damage, protease inhibitors, including but not limited to leupeptin, pepstatin A and phenylmethanesulfonylfluoride (PMSF) to inhibit endogenous proteases from degrading the target polypeptide, metal chelators, including but not limited to Ethylenediaminetetraacetic add (EDTA) and ethylene glycol tetraacetic add (EGTA), to inactivate metalloproteases, osmolytes, including but not limited to glycerol, detergents and sugars to stabilize protein structure or ionic stabilizers, including but not limited to salts such as NaCl, KCl and $(NH_4)_2SO_4$ to enhance solubility.

The term "wash buffer" refers to a buffer that is passed over the column material after the target composition has been loaded onto the column and prior to elution of the recombinantly produced target polypeptide. The wash buffer may serve to remove one or more contaminants, for example, host cell protein, from the column material, without substantial elution of the target. In general, the wash buffer has a pH of at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0. In one embodiment, the process includes one wash buffer, wherein the column is washed using at least about 5, or up to about 10 or 20 column volumes of a single wash buffer. In other embodiments, the process may include more than one wash buffer, for example, the process may include two different wash buffers. For example, the process may include a first wash step in which the column is washed using at least about 5, or up to about 10 or 20 column volumes of a first wash buffer and a second wash step in which the column is washed using at least about 5, or up to about 10 or 20 column volumes of a second wash buffer. In one embodiment, at least one wash buffer is the same as the equilibrating buffer. In another embodiment, at least one wash buffer is different from the equilibration buffer.

In a further embodiment a purification process is described in which residual levels of host cell protein (HCP) in eluate from a Protein A purification are reduced. In a more particular embodiment, residual HCP levels are reduced by including a fatty acid in a wash buffer used with the Protein A column. In one embodiment, a method of separating a recombinantly produced polypeptide from host cell protein is described. In another embodiment, a method for enhancing stability of a recombinantly produced polypeptide is described. In another embodiment, a method for reducing protease contamination in a formulation containing a recombinantly produced polypeptide is provided.

In general, short chain fatty acids, for example, fatty acids having a chain length of less than about 6 carbon atoms, do not significantly alter the level of HCP in the eluate. However, as fatty acid chain length is increased, a reduction in HCP is observed. In particular, inclusion of fatty acids with a medium chain length (i.e., between about 6 carbon atoms and about 12 carbon atoms) in the wash buffer significantly reduces the amount of HCP observed in the eluate. Examples of suitable fatty acids or fatty acid salts for inclusion in a Protein A wash buffer include, but are not limited to, fatty acids having a chain length of at least about 6, 7, 8 or 9 carbon atoms and up to about 10, 11 or 12 carbon atoms, or fatty acid salts thereof including, but not limited to, enanthic acid, caprylic acid, pelargonic acid, capric acid, undecyclic acid, lauric acid or combinations and salts thereof. In one embodiment, the fatty acid is included in a wash buffer at a concentration of at least about 25 mM or 50 mM, and up to about 75 mM, 100 mM, 125 mM, 150 mM or 200 mM. In one embodiment, the wash buffer includes a fatty acid solution prepared using a buffering agent such as tris(hydroxymethyl)aminomethane (often referred to as "Tris") (pH range 5.8-8.0), 4-(2-hydroxyethyl)-1-piperazineethanesulfonic acid (HEPES) (pH range 6.8-8.2), 3-(N-morpholino)propanesulfonic acid (MOPS) (pH range 6.5-7.9), wherein the fatty acid has a concentration of at least about 25 mM or 50 mM, and up to about 75 mM, 100 mM, 125 mM, 150 mM or 200 mM and the buffering agent has a concentration of at least about 10 mM, 25 mM, 50 mM or 75 mM and up to about 100 mM, 125 mM or 150 mM and the solution has a pH of at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0. In one embodiment, the pH of the buffering solution can be adjusted using an appropriate acid or base, such as hydrochloric acid (HCl) or sodium hydroxide/potassium hydroxide (NaOH/KOH).

While not wishing to be bound by theory, it is believed that the fatty acid removes HCPs by out-competing with the HCPs for binding sites on the antibody. For example, the level of host cell proteins can be reduced to 75%, 50%, 25%, 10% or even as low as 5% of the level of host cell proteins in eluate obtained from a column that was washed with a control buffer that does not include a fatty acid. In another embodiment, the level of host cell proteins can be reduced at least 2 fold, 3 fold, 4 fold, 5 fold, 10 fold, 15 fold, 20 fold, 25 fold and up to 30 fold, 35 fold, 40 fold, 45 fold or 50 fold when compared to the level of host cell proteins obtained using a wash that does not include a fatty acid.

In another embodiment, inclusion of a fatty acid in a Protein A wash can increase stability of a recombinantly produced polypeptide, such as an antibody, obtained from the Protein A purification. In one embodiment, inclusion of a fatty acid in a Protein A wash reduces protease activity, which can improve stability of the recombinantly produced polypeptide, for example, recombinantly produced antibody. In one embodiment, inclusion of a fatty acid in a Protein A wash reduces activity of proteases such as serine proteases, aspartyl proteases such as cathepsin-D, cysteine proteases, metalloproteases and aminopeptidases in the eluate or in a downstream formulation containing the recombinantly produced polypeptide obtained from the Protein A purification step. The reduction of protease activity can be measured using any suitably sensitive assay, including, but not limited to EnzChek® Protease Assay Kit E6638 from Molecular Probes, Eugene, Oreg. Any assay that can reliably detect or quantify levels >10 ng/mL for control preparations of proteases such as the aspartyl protease, Cathepsin-D, or the serine protease, Trypsin may also be used.

In another embodiment, inclusion of a fatty acid in a Protein A wash results in a reduction in particle formation, which is related to product stability, in the eluate or in a downstream formulation containing the recombinantly produced polypeptide obtained from the Protein A purification step. In another embodiment inclusion of a fatty acid in a Protein A wash results in a reduction in delayed-onset particle formation, which is related to product stability, in the eluate or in a downstream formulation containing the recombinantly produced polypeptide obtained from the Protein A purification step. Particle formation can be determined by visual inspection. For example, visual inspection for particles, clarity/opalescence, and color can be performed based on procedures adapted from the European Pharmacopeia (PhEur) sections 2.9.20, 2.2.1 and 2.2.2, respectively. Particles levels in samples can be compared against a series of barium sulfate visible particle standards. As an example, the standards that can be used include: 'free from visible particles' (0); four gradations of 'practically free from visible particles' (1 through 4); and three gradations of 'contains visible particles' (5, 6, and 7). In one embodiment, any sample designated as 'contains visible particles' is dispositioned as a 'fail.' In one embodiment, opalescence can be assessed by comparison with dilutions of a stabilized formazin standard (2660642) obtained from Hache-Lange (Loveland, Colo.). Color can be assessed by comparison with standards (83952) from Sigma-Fluke (St. Louis, Mo.). As used herein, the term "delayed-onset" refers to particle formation that, while not observed in the formulation initially, form after a period of time, for example, after 1 month, 2 months, 3 months, 6 months or up to 12 months, 18 months or 24 months. In one embodiment, particle formation is reduced when a formulation containing the recombinantly produced polypeptide is stored at a temperature at or at least about 0° C., 5° C. or 10° C. and at or up to about 25° C. or 40° C.

In another embodiment, inclusion of a fatty acid in a Protein A wash results in reduction of polypeptide fragmentation, which is also related to product stability, in the eluate or in a downstream formulation. In one embodiment, the recombinantly produced polypeptide in a formulation downstream of a purification process in which a fatty acid was included in at least one Protein A wash has a fragmentation rate of less than 5%, 4.5%, 4%, 3.5%, 3%, 2.5%, 2%, 1.5%, 1%, 0.95%, 0.90%, 0.80% or 0.75% per month when stored at 40° C. Methods for detecting polypeptide fragmentation are known and include, for example, reverse phase high performance liquid chromatography (RP-HPLC).

In addition to the fatty acid, other elements of the wash buffer can impact the level of HCP detected in the eluate. In particular, as the pH of the wash buffer is increased, the HCP level may decrease. Additionally, the concentration of salt, such as sodium chloride, in the wash buffer can also impact the level of HCP detected in the eluate. In general, as the concentration of salt or sodium chloride increases, the HCP level in the eluate decreases. In one embodiment, the wash buffer has a pH of at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0 and includes at least about 0.25 M, 0.5 M, 1 M, 1.25 M, 1.5M, 1.75 M or 2M salt, such as sodium chloride and up to about 2.0 M, 2.25 M, 2.5 M, 2.75 M or 3.0 M salt, such as sodium chloride and a fatty acid at a concentration of at least about 25 mM or 50 mM, and up to about 75 mM, 100 mM, 125 mM, 150 mM or 200 mM. In one embodiment, the wash buffer includes between about 50 mM and about 100 mM sodium caprylate at a pH between about 8 to about 9. In another embodiment, the wash buffer includes between about 50 mM and about 100 mM sodium caprylate at a pH between about 8 to about 9 and between about 2.0 M to about 2.5 M sodium chloride. In a more particular embodiment, the wash buffer includes between about 50 mM to about 100 mM sodium caprylate in 100 mM Tris at a pH between about 8.0 and about 9.0. In a more particular embodiment, the wash buffer includes about 50 mM to about 100 mM sodium caprylate in 100 mM Tris at a pH between about 8.0 and about 9.0 and between about 2.0 M and about 2.5 M sodium chloride.

Additionally, the wash buffer may include one or more additives to increase protein purity, stability, and function, including, but not limited to reducing agents such as 2-mercaptoethanol (BME), dithiothreiotol (DDT) or Tris(2-carboxyethyl)phosphine (TCEP) to protect against oxidative damage, protease inhibitors, including but not limited to leupeptin, pepstatin A and phenylmethanesulfonylfluoride (PMSF) to inhibit endogenous proteases from degrading the target polypeptide, metal chelators, including but not limited to Ethylenediaminetetraacetic acid (EDTA) and ethylene glycol tetraacetic acid (EGTA), to inactivate metalloproteases, osmolytes, including but not limited to glycerol, detergents and sugars to stabilize protein structure or ionic stabilizers, including but not limited to salts such as NaCl, KCl and $(NH_4)_2SO_4$ to enhance solubility.

The term "elution buffer" refers to a buffer used to elute (i.e., remove) the target polypeptide from the column. The elution pH can vary depending upon the binding affinity of the polypeptide to the column. Some antibodies demonstrate a higher binding affinity and may require a lower elution pH. In general, the pH of the elution buffer is lower than the pH of the loading buffer. Typically, the elution buffer has a pH of at least about 2.0, 2.1, 2.2, 2.3, 2.4, 2.5, 2.6, 2.7, 2.8, 2.9, 3.0, 3.1, 3.2, 3.3, 3.4, or 3.5 and up to about 3.6, 3.7, 3.8, 3.9, 4.0, 4.1, 4.2, 4.3, 4.4, 4.5, 4.5, 4.7, 4.8, 4.9 or 5.0. Examples of elution buffers include buffers including sodium citrate, citric acid or acetic acid at a concentration of at least about 25 mM, 50 mM and up to about 100 mM, 150 mM or 200 mM. In one embodiment, the elution buffer includes at least about 25 mM, 50 mM and up to about 100 mM, 150 mM or 200 mM sodium citrate at has a pH of at least about 2.0, 2.1, 2.2, 2.3, 2.4, 2.5, 2.6, 2.7, 2.8, 2.9, 3.0, 3.1, 3.2, 3.3, 3.4, or 3.5 and up to about 3.6, 3.7, 3.8, 3.9, 4.0, 4.1, 4.2, 4.3, 4.4, 4.5, 4.5, 4.7, 4.8, 4.9 or 5.0. Additionally, the elution buffer may include one or more additives to increase protein purity, stability, and function, including, but not limited to reducing agents such as 2-mercaptoethanol (BME), dithiothreiotol (DDT) or Tris(2-carboxyethyl)phosphine (TCEP) to protect against oxidative damage, protease inhibitors, including but not limited to leupeptin, pepstatin A and phenylmethanesulfonylfluoride (PMSF) to inhibit endogenous proteases from degrading the target polypeptide, metal chelators, including but not limited to Ethylenediaminetetraacetic acid (EDTA) and ethylene glycol tetraacetic acid (EGTA), to inactivate metalloproteases, osmolytes, including but not limited to glycerol, detergents and sugars to stabilize protein structure or ionic stabilizers, including but not limited to salts such as NaCl, KCl and $(NH_4)_2SO_4$ to enhance solubility. In one embodiment, the target molecule is eluted using at least 5 and up to 10 or up to 20 column volumes of elution buffer. The eluate can be monitored using techniques well known to those skilled in the art, for example by monitoring the absorbance using a spectrophotometer set at $OD_{280}$ nm. In one embodiment, the Protein A purification step has a recovery rate of at least about 70%, 75%, 80%, 81%, 82%, 83%, 84% or 85% and up to about 86%, 87%, 88%, 89%, 90% or 95%. Recovery can be determined, for example, by calculating the percentage of protein in the Eluate relative to the amount that was loaded onto the column.

Polishing chromatography steps 104, 105 provide additional viral, host cell protein (HCP), endotoxin and DNA clearance, as well as assist in the removal of aggregates, unwanted product variants and other minor contaminants. Polishing steps 104, 105 generally include one or more chromatographic steps such as ion exchange chromatography, mixed mode chromatography, hydrophobic interaction chromatography, and combinations thereof.

In one embodiment, the purification process includes at least one ion exchange chromatography step. The term "ion exchange chromatography" refers to a chromatographic process using an immobile matrix that carries covalently bound charged substituents. The "ion exchange material" has the ability to exchange its counter ions, which are not covalently bound, for similarly charged binding partners or ions in the surrounding solution. Polypeptides have numerous functional groups that can have either positive or negative charges. Ion exchange chromatography separates polypeptides based on net charge, which is dependent on the pH and/or ionic concentration of the mobile phase. Polypeptides can thus be separated by adjusting the pH and/or ionic concentration of the mobile phase. In some embodiments, the target polypeptide is captured by the column and then eluted (also referred to as "bind and elute" mode). In other embodiments, the target polypeptide flows through the column and contaminants are bound (also referred to as a "flow through mode"). Elution from an ion exchange material is generally achieved by increasing the ionic strength of the buffer to compete with the recombinant polypeptide for charged sites of the ion exchange matrix. The elution process be gradual (gradient elution) or stepwise (step elution) and the eluate can be monitored using a UV spectrophotometer set at $OD_{280}$ nm.

Depending on the charge of the counter ions, "ion exchange chromatography" can be referred to as "cation exchange," "anion exchange," or "mixed-mode ion exchange." The term "cation exchange" refers to a chromatographic method having a solid phase that is negatively charged with free cations available for exchange with cations in an aqueous solution passed over or through the column. Cation exchange chromatography can be used to purify a recombinant polypeptide if the target is maintained under conditions in which the target polypeptide is positively charged. For example, the solution can be titrated so that the solution pH is lower than the isoelectric point of the polypeptide. Other positively charged impurities may also be bound to the cationic column resin in addition to the target polypeptide. As such, the target polypeptide can be recovered by elution from the column under conditions (e.g., pH and salt concentration) in which the target polypeptide elutes while impurities remain bound to the resin. Cation exchange resins can include strong acidic ligands such as sulphopropyl, sulfoethyl and sulfoisobutyl groups or weak acidic ligand such as carboxyl groups. Examples of commonly used cation exchange resins include carboxymethyl (CM), sulfoethyl(SE), sulfopropyl(SP), phosphate (P) and sulfonate(S) resins.

The term "anion exchange" refers to a chromatographic method having a solid phase that is positively charged with free anions available for exchange with anions in an aqueous solution passed over or through the solid phase. The anion exchange columns are typically operated in a flow through mode, such that negatively charged impurities are bound to the resin while the positively charged target polypeptide is recovered in the flow through stream. However, anion exchange columns may also be used in a bind and elute mode, depending upon the pI of the target polypeptide and the impurities to be removed. Examples of positively charged groups that are used in anion exchange include weakly basic groups such as diethylamino ethyl (DEAE) or dimethylamino ethyl (DMAE) and strongly basic groups such as quaternary amine (Q) groups, trimethylammonium ethyl (TMAE) or quaternary aminoethyl (QAE).

In one embodiment, the eluate obtained from the Protein A capture step 102 is subjected to one, more than one, or two ion exchange separation steps in which the second ion exchange separation involves a separation based on the opposite charge than the first ion exchange separation. For example, if an anion exchange step 104 is employed after capture 102, the second ion exchange chromatographic step 105 may be a cation exchange step. Conversely, if capture 102 was followed by a cation exchange step 104, that step would be followed by an anion exchange step 105. Alternately, in other embodiments the purification scheme 100 may include only a cationic exchange step or only an anionic exchange step.

In one embodiment, the purification scheme 100 includes at least one a hydrophobic interaction separation as a polishing step 104 or 105. "Hydrophobic interaction chromatography" (HIC) refers to chromatographic separation based on the reversible interaction between a polypeptide and a hydrophobic ligand bound to the solid phase of the chromatography resin. Hydrophobic interaction chromatography is often used to remove protein aggregates, such as antibody aggregates, and process-related impurities. During HIC, the target polypeptide binds to the column at a high salt concentration and is eluted by decreasing the salt concentration. Since the interaction between the target polypeptide and the hydrophobic ligand are enhanced by the use of buffers with high ionic strength, HIC can be a suitable purification step for use after ion exchange chromatography. Various ions can be arranged in a so-called soluphobic series depending on whether they promote hydrophobic interactions (salting-out effects) or disrupt the structure of water (chaotropic effect) and lead to the weakening of the hydrophobic interaction.

In other embodiments, the purification scheme can include "hydrophobic charge induction chromatography" (HCIC) as a polishing step 104 or 105. HCIC is based on the pH-dependent behavior of ligands that ionize at low pH. HCIC employs heterocyclic ligands at high densities such that hydrophobic interaction between the target polypeptide and the column material are possible without the need for a high salt concentration. Elution in HCIC can be accomplished by lowering the pH to produce charge repulsion between the ionizable ligand and the bound protein.

In one embodiment, the purification scheme 100 includes one or more viral inactivation 103 and/or viral clearance 106 steps, for example, to remove endogenous retroviruses and adventitious viruses. In one embodiment, a viral inactivation step 103 can be included after the target molecule is captured 102. Viral inactivation techniques are known and include, for example, heat inactivation (pasteurization), pH inactivation, disruption of the lipid envelope using solvent/detergent, UV and γ-ray irradiation and the use of chemical inactivating agents. In one embodiment, viral inactivation includes a step of low pH viral inactivation, which includes incubating the mixture for a period of time at low pH, neutralizing the pH and removing particulates by filtration. In one embodiment, the low pH viral inactivation includes titrating the recombinant polypeptide to a pH between about 2 and about 5, or between about 3 and about 4, or between about 3.3 and about 3.8. The pH of the sample mixture may be lowered by any suitable acid including, but not limited to, citric acid, acetic acid, caprylic acid, or other suitable acids. The choice of pH level depends on the stability profile of the recombinantly produced polypeptide and other buffer components. Typically, the titrated solution is incubated for at least about 30 or 45 minutes and up to about 1, 1.5 hours, or 2 hours, typically at room temperature. After viral inactivation, the pH of the recombinant polypeptide solution can be adjusted to a more neutral pH, for example, between about 4.5 to about 8.5, or between about 4.5 and about 5.5 prior to continuing the purification process.

In another embodiment, a viral clearance step 105, such as a viral filtration, can be included in the purification scheme. Virus-retentive filters are commercially available and include ultrafilters or microfilters such as hydrophilic polyethersulfone (PES), hydrophilic polyvinylidene (PVDF) and regenerated cellulose filters. Based on the size of viruses that are removed, virus filters can be categorized into retrovirus filters and parvovirus filters. In one embodiment, the purification scheme includes an ultrafiltration (UF) and/or diafiltration (DF) step 107 to further purify and concentrate the antibody sample. UF/DF can increase the concentration of the target polypeptide as well as replace buffering salts with a particular formulation buffer. Ultrafiltration (UF) refers to a type of membrane filtration in which hydrostatic pressure forces a liquid against a semipermeable membrane. Suspended solids and solutes of high molecular weight, such as the target polypeptide, are retained in the retentate, while water and low molecular weight solutes pass through the membrane in the filtrate. In this manner, the target antibodies are concentrated as liquid and salt are removed. Generally, the low molecular weight composition in the concentrate remains constant so the ionic strength of the concentrated solution remains relatively constant. "Diafiltration" refers to a method that uses ultrafiltration membranes to remove, replace, or lower the concentrations of salts or buffering components from solutions containing proteins, such as antibodies, peptides, nucleic acids, and other biomolecules. Continuous diafiltration (also referred to as constant volume diafiltration) involves washing out the original buffer salts (or other low molecular weight species) in the retentate by adding water or a new buffer, such as a formulation buffer, to the retentate to form a formulation containing the recombinantly produced polypeptide. Typically, the new buffer is added at the same rate as filtrate is being generated such that the retentate volume and product concentration does not change appreciably during diafiltration.

4.5. Formulations

In one embodiment, the purified recombinantly produced polypeptide is prepared in a liquid formulation. In a more particular embodiment, the recombinantly produced polypeptide in the liquid formulation is an antibody or antibody fragment. In one embodiment, the liquid formulation includes an aqueous carrier, such as water. In one embodiment, the liquid formulation is sterile. In another embodiment, the liquid formulation is homogeneous. In another embodiment, the formulation is isotonic. In one embodiment, the liquid formulation includes at least about 1 mg/ml, 5 mg/ml, 10 mg/ml, 20 mg/ml, 25 mg/ml, 50 mg/ml, 75 mg/ml, 100 mg/ml, 125 mg/ml, 150 mg/ml, 175 mg/ml, 200 mg/ml, 250 mg/ml, or 300 mg/ml of the purified recombinantly produced polypeptide. In one embodiment, the formulation has a pH of at least about 3.0, 3.5, 4.0, 4.5, 5.0, 5.1, 5.2, 5.3, 5.4, 5.5, 5.6, 5.7, 5.8, 5.9, 6.0, 6.1, 6.2, 6.3, 6.4 or 6.5 and up to about 6.6, 6.7, 6.8, 6.9, 7.0, 7.5, 8.0, 8.5, or 9.0. The formulation may also include common excipients and/or additives, including, but not limited to buffering agents, sugars, saccharides, salts, surfactants, solubilizers, diluents, binders, stabilizers, lipophilic solvents, amino acids, chelators, preservatives or combinations thereof.

In another embodiment, the purified recombinantly produced polypeptide is prepared as a lyophilized formulation. In a more particular embodiment, the recombinantly produced polypeptide in the lyophilized formulation is an antibody or antibody fragment. As used herein, the term "lyophilized" refers to a formulation that has been subjected to a drying procedure, such as lyophilization, where at least 50% of moisture has been removed. In one embodiment, the lyophilized formulation includes a lyoprotectant. The term "lyoprotectant" refers to a molecule which, when combined with a recombinantly produced polypeptide of interest, significantly prevents or reduced chemical and/or physical instability of the polypeptide upon lyophilization and subsequent storage. Lyoprotectants include, but are not limited to, sugars and their corresponding sugar alcohols; an amino acid such as monosodium glutamate, arginine or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; Pluronics®; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, maltulose, isomaltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant. In one embodiment, the lyoprotectant is added to the formulation in a "lyoprotecting amount" which means that, following lyophilization of the protein in the presence of the lyoprotecting amount of the lyoprotectant, the protein essentially retains its physical and chemical stability and integrity upon lyophilization and storage. A "reconstituted" formulation is one which has been prepared by dissolving a lyophilized formulation in a diluent such that the recombinantly produced polypeptide is dispersed in the reconstituted formulation. The reconstituted formulation is suitable for administration to a patient. The "diluents" includes pharmaceutically acceptable diluents, including, but not limited to, sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers. In one embodiment, the recombinant polypeptide is included in a lyophilized formulation at a concentration of at least about 10 mg/ml, 20 mg/ml, 30 mg/ml, 40 mg/ml or 50 mg/ml and up to about 60 mg/ml, 70 mg/ml, 80 mg/ml, 90 mg/ml or 100 mg/ml. In a more particular embodiment, the lyophilized formulation includes an amino acid, such as histdine, arginine or glutamic acid as a buffer at concentration of at least about 10 mM, 15 mM, 20 mM or 25 mM and up to about 30 mM, 40 mM or 50 mM. In one embodiment, the lyophilized formulation includes a sugar such as trehalose or sucrose at a concentration of at least about 50 mM, 100 mM, 150 mM, 175 mM, 200 mM or 225 mM and up to about 250 mM or 300 mM. In one embodiment, the lyophilized formulation includes at least about 0.01%, 0.02% 0.03%, 0.04% or 0.05% (w/v) and up to about 0.06%, 0.07%, 0.08%, 0.09% or 0.1% (w/v) of a surfactant, such a polysorbate 80. In one embodiment, the lyophilized formulation has a pH of at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, or 7.9, and up to about 8.0, 8.1, 8.2, 8.3, 8.4, 8.5, 8.6, 8.7, 8.8, 8.9, or 9.0.

In one embodiment, the recombinantly produced polypeptide is formulated for parenteral administration. In one embodiment, the formulation is injectable. In one embodiment, the recombinantly produced polypeptide is formulated for intravenous, subcutaneous, or intramuscular administration.

The formulations prepared with a recombinantly produced polypeptide purified as described herein exhibit stability, low to undetectable levels of antibody fragmentation, low to undetectable levels of particle formation (i.e. remain free or practically free from visible particles and clear to slightly opalescent), low to undetectable levels of protease activity and very little to no loss of the biological activities of the recombinantly produced polypeptide during manufacture, preparation, transportation, and storage.

The term "low to undetectable levels of fragmentation" as used herein refers to samples containing less than about 80%, 85%, 90%, 95%, 98% or 99% of the full length polypeptide, for example, in a single peak as determined by high performance size exclusion chromatography (HPSEC), representing the non-degraded polypeptide, and containing no other single peaks having more than about 5%, 4% 3%, 2%, 1%, or 0.5% of the polypeptide in each. In another embodiment, the formulation exhibits reduced fragmentation of the recombinantly produced polypeptide. In one embodiment, a formulation that includes recombinantly produced polypeptide in which a fatty acid has been included in a Protein A wash buffer includes less than 5% fragmented polypeptides as determined by RP-HPLC upon storage at about 40° C. for at least about 1 day, 2 days, 3 days, 4 days, 5 days, 6 days or 7 days; or at least about 1 week, 2 weeks, 3 weeks, 4 weeks, 5 weeks or 6 weeks. In another embodiment, a formulation that includes recombinantly produced polypeptide in which a fatty acid has been included in a Protein A wash buffer includes less than 5% fragmented polypeptides as determined by RP-HPLA upon storage at about 4° C. or about 5° C. for at least about 1 week, 2 weeks, 3 weeks, 4 weeks, 5 weeks, 6 weeks, 7 weeks, 8 weeks, 9 weeks, 10 weeks, 11 weeks or 12 weeks; or at least about 1 month, 2 months, 3 months, 4 months, 5 months, 6 months, 7 months, 8 months, 9 months, 10 months, 11 months or 12 months.

The phrase "low to undetectable levels of particle formation" as used herein refers to samples which "remain free or practically free from visible particles and clear to slightly opalescent" upon visual inspection for particles and clarity/opalescence following procedures adapted from a suitable compendial method such as the European Pharmacopeia (PhEur) sections 2.9.20, 2.2.1 and 2.2.2 or samples in which no particles are detected (i.e., the formulation remains clear and colorless) upon visual inspection. In one embodiment, a formulation prepared with a recombinantly produced polypeptide purified as described herein is clear and colorless, as determined by visual inspection, upon storage at about 40° C. for at least about 1 day, 2 days, 3 days, 4 days, 5 days, 6 days, or 7 days; or at least about 1 week, 2 weeks, 3 weeks, 4 weeks, 5 weeks, or 6 weeks. In another embodiment, the formulation is clear and colorless, as determined by visual inspection, upon storage at about 4° C. or about 5° C. for at least about 1 week, 2 weeks, 3 weeks, 4 weeks, 5 weeks, 6 weeks, 7 weeks, 8 weeks, 9 weeks, 10 weeks, 11 weeks, or 12 weeks; or at least about 1 month, 2 months, 3 months, 4 months, 5 months, 6 months, 7 months, 8 months, 9 months, 10 months, 11 months, or 12 months.

The term "low to undetectable protease activity" as used herein refers to samples in which protease activity is below the detection limit (for example, less than about 10 ng/mL), for example, using a fluorescent protease assay such as EnzChek® Protease Assay Kit (E6638, Molecular Probes, Eugene, Oreg.). In one embodiment, a formulation prepared with a recombinantly produced polypeptide purified as described herein shows low to undetectable protease activity upon storage at about 40° C. for at least about 1 day, 2 days, 3 days, 4 days, 5 days, 6 days, or 7 days; or at least about 1 week, 2 weeks, 3 weeks, 4 weeks, 5 weeks, or 6 weeks. In another embodiment, the formulation shows low to undetectable protease activity upon storage at about 4° C. or about 5° C. for at least about 1 week, 2 weeks, 3 weeks, 4 weeks, 5 weeks, 6 weeks, 7 weeks, 8 weeks, 9 weeks, 10 weeks, 11 weeks, or 12 weeks; or at least about 1 month, 2 months, 3 months, 4 months, 5 months, 6 months, 7 months, 8 months, 9 months, 10 months, 11 months, or 12 months.

In one embodiment, the formulation exhibits improved stability of the recombinantly produced polypeptide. In particular, inclusion of a fatty acid in the Protein A wash buffer results in an antibody formulation having improved stability when compared to a formulation prepared using a Protein A wash buffer that does not include a fatty acid. In one embodiment, a formulation prepared with a recombinantly produced polypeptide purified as described herein is stable upon storage at about 40° C. for at least abut 1 day, 2 days, 3 days, 4 days, 5 days, 6 days, or 7 days; or at least about 1 week, 2 weeks, 3 weeks, 4 weeks, 5 weeks, or 6 weeks; or at least about 1 month, 2 months, 3 months, 4 months, 5 months, or 6 months. In another embodiment, a formulation prepared with a recombinantly produced polypeptide purified as described herein is stable upon storage at about 4° C. or about 5° C. for at least about 1 week, 2 weeks, 3 weeks, 4 weeks, 5 weeks, 6 weeks, 7 weeks, 8 weeks, 9 weeks, 10 weeks, 11 weeks, or 12 weeks; or at least about 1 month, 2 months, 3 months, 4 months, 5 months, 6 months, 7 months, 8 months, 9 months, 10 months, 11 months, or 12 months; or at least about 1 year, 2 years, 3 years, 4 years, 5 years, 6 years, 7 years, 8 years, 9 years, 10 years, 11 years, or 12 years.

4.6. Host Cell Protein Detection

Methods for determining the residual levels of host cell protein (HCP) concentration are known and include, for example detecting residual HCP levels using an immunoassay, such as an enzyme-linked immunosorbant assay (ELISA), for example, in which the primary antibody is specific to the HCPs produced from a particular host cell, e.g., CHO cells or *E. coli* cells, used to generate the recombinant polypeptide. The primary antibody may be produced according to conventional methods known to those of skill in the art. For example, the primary antibody may be generated against a cell lysate of the host cells used for antibody production. One HCP immunoassay platform is commercially available from Gyros (Warren, N.J.).

4.5. Protease Detection

The EnzChek® Protease Assay Kit (E6638, Molecular Probes, Eugene, Oreg.) can be used to assess protease activity in samples. Samples can be read at a single pH or at multiple pHs to generate a profile of protease activity vs pH. Different proteases have different activity vs. pH profiles and measurements at different pH levels therefore increases the ability to detect proteases of many different types in a sample.

In another embodiment, the BODIPY fluorescence assay can be used over a pH range 4-9 with less than a ca. 10% error. The detection substrate in the kit is BODIPY®-casein conjugate. When dye-labeled fragments of digested casein substrate are released by active proteases in the samples there can be a fluorescence intensity increase due to decreased self-quenching of the dye. Protein samples can be diluted 10-fold into 20 mM citrate-phosphate buffer at pHs typically ranging from 4 to 8. Matching placebos can be prepared. The citrate-phosphate buffer can be prepared by mixing 20 mM citric acid and 20 mM dibasic sodium phosphate to achieve the desired pHs. The BODIPY®-casein conjugate detection substrate can be diluted in the appropriate buffer to generate a working reagent at each pH from 4 to 8 at about 10 μg/mL. An equal (typically 100 μL) volume of sample and working reagent can be added to wells in a white microplate to generate triplicate assay samples and matching placebos over the pH range 4 to 8. The samples can be sealed and incubated at 40° C. for a typical duration of 3 to 5 hours. The dye fluorescence can be excited at 485 nm and the emission intensity at 530 nm can be recorded using a 495 nm cutoff filter on a Molecular Devices SpectraMax® fluorescent plate reader (Sunnyvale, Calif.). The intensity vs. pH for the samples can then be recorded. Intensity increases of the sample compared to the blank of less than about 20% can be dispositioned as negative for protease activity per the manufacturer guidelines based on variability in the method. Results for samples can be buffer-subtracted and plotted vs. pH and can be used to determine the presence of protease activity in samples. Multiple replicates can be run to assess the variability for low readings. For relative quantification control preparations of known proteases such as Cathepsin-D or Trypsin as comparators can be used. To confirm the presence of proteases, protease inhibitors can be added to samples resulting in a relative decrease, or elimination of the detected protease activity as a confirmation of the results. Examples of protease inhibitors used to diagnose the presence of proteases in samples can include the broad protease inhibitor cocktail (Catalog No. P2714, Sigma-Aldrich, St. Loius, Mo.) containing AEBSF, Aprotinin, Bestatin-HCl, E-64, EDTA, Leupeptin used at 1× suggested concentration. Each individual inhibitor can also be used for further confirmation of protease activity. Protease inhibitors are commercially available and can be sourced from a suitable supplier such as ThermoScientific, Rockford, Ill.: AEBSF-HCl (inhibits serine proteases), Catalog No. 78431; Aprotinin (inhibits serine proteases), Catalog No. 78432; Bestatin (inhibits Aminopeptidases), Catalog No. 78433; E-64 (inhibits cysteine proteases), Catalog No. 78434; Leupeptin (inhibits serine and cysteine proteases), Catalog No. 78435; Pepstatin-A (inhibits aspartyl proteases), Catalog No. 78436; EDTA (ethylenediaminetetraacetic acid, inhibits metalloproteases).

5. EXAMPLES

The examples below are given so as to illustrate the practice of this invention. They are not intended to limit or define the entire scope of this invention.

| SEQ ID NO: | Description |
|---|---|
| | Sequence Information: |
| 1 | AB1 VH CDR1 PRT |
| 2 | AB1 VH CDR2 PRT |
| 3 | AB1 VH CDR3 PRT |
| 4 | AB1 VL CDR1 PRT |
| 5 | AB1 VL CDR2 PRT |
| 6 | AB1 VL CDR3 PRT |
| 7 | AB1 VH PRT |
| 8 | AB1 VL PRT |
| 9 | AB2 VH CDR1 PRT |
| 10 | AB2 VH CDR2 PRT |
| 11 | AB2 VH CDR3 PRT |
| 12 | AB2 VL CDR1 PRT |
| 13 | AB2 VL CDR2 PRT |
| 14 | AB2 VL CDR3 PRT |
| 15 | AB2 VH DNA |
| 16 | AB2 VH PRT |
| 17 | AB2 VL DNA |
| 18 | AB2 VL PRT |

The reagents employed in the examples are commercially available or can be prepared using commercially available instrumentation, methods, or reagents known in the art. The examples illustrate various aspects of the invention and practice of the methods of the invention. The examples are not intended to provide an exhaustive description of the many different embodiments of the invention. Thus, although the invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

Example 1: The Effect of pH, Sodium Chloride and Sodium Caprylate on HCP Levels Large amounts of HCP (i.e., 630 ng/mg) were observed in a standard purification process for a human IgG1 monoclonal antibody that specifically binds human IL-18 (NCIMB Accession Number 41786), which was not cleared by Protein A purification or other process steps. Additional wash steps were evaluated for their ability to reduce HCP levels. In particular, the effects of wash pH, wash sodium chloride, sodium caprylate and combinations thereof on HCP clearance, recovery and product were examined. The experiment included 16 experimental runs plus an additional run using a standard wash buffer (run 17). The compositions of the experimental washes are shown in Table 1. All experimental wash buffers in Table 1 were made in 100 mM Tris and pH adjusted using concentrated HCl. Protein A chromatography buffers were prepared as shown in Table 2. All runs were performed using a MabSelect SuRe column (C11-032 TRICORN, GE Healthcare) having a bed height of 20 cm and a column volume of 3.93 mL and were performed overnight at 350 cm/hr (1.17 mL/min) using the AKTA AVANT system (GE Healthcare) according to the process outlined in Table 3.

TABLE 1

Experimental Washes

| Run | Wash pH | Wash Sodium chloride (M) | Sodium caprylate (mM) |
|---|---|---|---|
| 1 | 7 | 1.25 | 50 |
| 2 | 8 | 1.25 | 100 |
| 3 | 8 | 1.25 | 50 |
| 4 | 8 | 1.25 | 50 |
| 5 | 7.5 | 2.5 | 100 |
| 6 | 9 | 0 | 0 |
| 7 | 9 | 2.5 | 100 |
| 8 | 7 | 0 | 0 |
| 9 | 8 | 1.25 | 0 |
| 10 | 9 | 2.5 | 0 |
| 11 | 9 | 1.25 | 50 |
| 12 | 8 | 0 | 50 |
| 13 | 8 | 2.5 | 50 |
| 14 | 7 | 0 | 100 |
| 15 | 9 | 0 | 100 |
| 16 | 7 | 2.5 | 0 |
| 17 | 9 | 2.5 | 50 |

TABLE 2

Protein A Chromatography Buffers

| Buffer | Purpose |
|---|---|
| 20 mM Sodium Phosphate, pH 7.0 | Equilibration and re-equilibration |
| 100 mM sodium citrate, pH 3.5 | Elution |
| 100 mM citric acid | Strip |
| 0.5M sodium Hydroxide | Sanitisation |
| 0.1M Tris | Neutralisation |

TABLE 3

Process conditions

| Parameter | Buffer | Notes | Column volumes |
|---|---|---|---|
| Equilibration | 20 mM sodium phosphate, pH 7.0 | | 5 |
| Load | Clarified Cell Culture Harvest | Loaded to 40 mg/mL capacity | NA |
| Re equilibration | 20 mM sodium phosphate, pH 7.0 | | 5 |
| Wash 1 | Experimental Wash Buffer | | 5 |
| Wash 2 | 20 mM sodium phosphate, pH 7.0 | | 5 |
| Elution | 100 mM sodium citrate, pH 3.5 | Eluate collected from 0.5 OD to 0.5 OD | 5 |
| Strip | 100 mM citric acid | | 2 |
| Sanitisation/clean | 0.5M sodium hydroxide | | 2 |

Upon elution from the Protein A column, the eluates were neutralised to pH 5.0 with 0.1 M Tris and a 1 mL sample was taken for HCP analysis. The eluate was filtered using a Millipore Steriflip (Prod No. SCGP00525) to remove a precipitate associated with high HCP levels. Removal of this precipitate by filtration can help reduce HCP levels. Following filtration the neutralised eluate was further sampled for concentration determination, HCP assay (post filtration) and HPSEC. The concentration of each sample was determined by the adsorption at 280 nm. Since all samples were diluted 1:20, the value was multiplied by 20 (to account for dilution) and divided by the extinction coefficient of 1.55 (experimentally determined). Size Exclusion Chromatography (SEC) analysis was performed on an Agilent HPLC system with a TSK-Gel G3000. 250 μg was injected by diluting the formulation to about 10 mg/mL in PBS and injecting 25 μL. Samples were analyzed for Host Cell Protein using an open immunoassay platform (Gyros) with affinity purified sheep antisera to detect HCP from CHO cells. A Fluorescent protease detection kit (23266 from Pierce Biotechnology) was used to measure proteolytic activity of samples using FTC-Casein as the substrate. The procedures included in the kit instructions were followed and the results were reported as units calculated as the equivalent ng/mL value for a Trypsin standard curve. The results are shown in Table 4.

TABLE 4

Recovery, purity and HCP

| | | | | Pre Filtration | | Post Filtration | |
|---|---|---|---|---|---|---|---|
| | Recovery | Purity (%) | | | HCP | HCP | HCP | HCP |
| Run | (%) | Agg | Monomer | Frag | (mg/mL) | (ng/mg) | (mg/mL) | (ng/mg) |
| 1 | 84.80 | 1.85 | 98.15 | 0 | 6022.62 | 772.39 | 2757.66 | 382.32 |
| 2 | 83.19 | 2.4 | 97.6 | 0 | 3557.52 | 420.41 | 1785.85 | 226.15 |
| 3 | 83.64 | 2.8 | 97.2 | 0 | 4020.47 | 428.71 | 2615.26 | 306.17 |
| 4 | 87.58 | 2.6 | 97.4 | 0 | 5703.68 | 606.86 | 2418.31 | 279.31 |
| 5 | 82.44 | 2.2 | 97.8 | 0 | 2117.23 | 221.83 | 924.47 | 105.83 |
| 6 | 88.18 | 2.6 | 97.4 | 0 | 5926.16 | 577.56 | 2799.62 | 296.41 |
| 7 | 80.85 | 2.1 | 97.93 | 0 | 1020.41 | 105.70 | 743.01 | 83.45 |
| 8 | 88.89 | 2.7 | 97.3 | 0 | 17568.70 | 1618.22 | 3617.73 | 372.84 |
| 9 | 87.72 | 2.1 | 97.9 | 0 | 4854.61 | 556.89 | 3049.51 | 374.54 |
| 10 | 89.94 | 3.7 | 96.1 | 0.14 | 5288.24 | 599.00 | 3080.29 | 365.58 |
| 11 | 90.28 | 3.3 | 96.7 | 0 | 2784.78 | 327.75 | 2219.73 | 278.36 |
| 12 | 89.07 | 2.1 | 97.9 | 0 | 7030.49 | 769.58 | 2450.02 | 286.39 |
| 13 | 87.86 | 2.7 | 97.3 | 0 | 3465.77 | 359.95 | 2408.91 | 268.23 |
| 14 | 92.22 | 2.7 | 97.3 | 0 | 6080.68 | 601.70 | 3228.27 | 345.09 |
| 15 | 92.18 | 3.7 | 96.3 | 0 | 2490.16 | 241.45 | 1971.22 | 206.45 |
| 16 | 90.55 | 3 | 96.9 | 0.1 | 8430.85 | 838.00 | 4666.13 | 492.01 |
| 17 | 85.65 | 2.9 | 97.1 | 0 | 2677.29 | 293.06 | 2031.21 | 238.88 |

As can be seen in Table 4, the purity was significantly affected by each factor (pH, sodium chloride and sodium caprylate) individually. Additionally, the results indicate an interaction between sodium caprylate and sodium chloride.

Table 5 shows the significance of the effect (Prob>F values greater than 0.05 would be determined to be not significant).

TABLE 5

Purity

| Parameter | Prob > F |
|---|---|
| Intercept | 1 |
| Wash pH (7.9) | 0.03032 |
| Wash Sodium chloride (M) (0, 2.5) | 0.01887 |
| Sodium caprylate (mM) (0, 100) | 0.01383 |
| Wash pH*Wash Sodium chloride (M) | 0.97956 |

TABLE 5-continued

Purity

| Parameter | Prob > F |
|---|---|
| Wash pH*Sodium caprylate (mM) | 0.66562 |
| Wash Sodium chloride (M)*Sodium caprylate (mM) | 0.00573 |
| Wash pH*Wash pH | 0.22777 |
| Wash Sodium chloride (M)*Wash Sodium chloride (M) | 0.28559 |
| Sodium caprylate (mM)*Sodium caprylate (mM) | 0.43541 |

Figure 2:
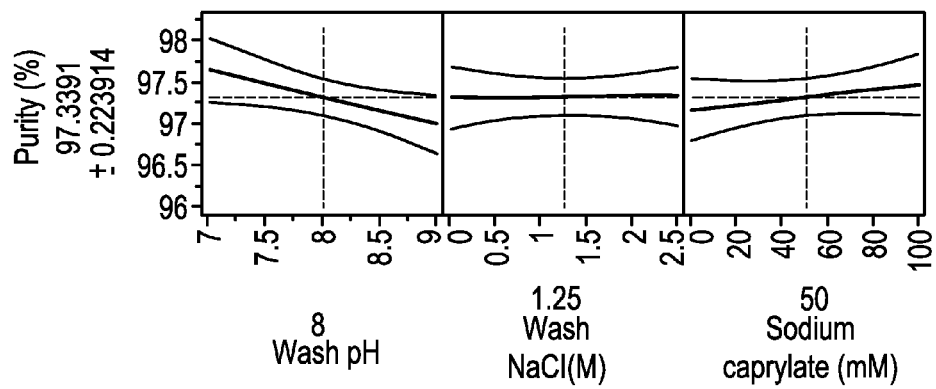
FIG. 2 shows the effects of wash pH, sodium chloride wash and sodium caprylate on eluate purity.
Figure 3:
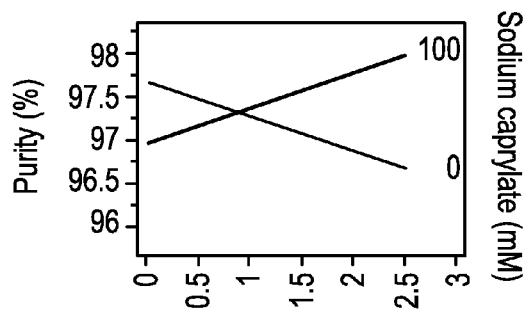
FIG. 3 shows the effect of the interaction between sodium caprylate and sodium chloride on eluate purity.

The effects of the three factors (wash pH, sodium chloride wash, and sodium caprylate) on eluate purity is shown in FIG. 2. Increasing the pH had the biggest effect on eluate purity, resulting in a drop of 0.6% as the pH was increased from 7.0 to 9.0 when both wash sodium chloride and sodium caprylate were at midpoint values (displayed in the top left corner). FIG. 3 shows a reduction in the eluate purity as wash sodium chloride was increased in the absence of sodium caprylate (grey line). However, in the presence of sodium caprylate, this effect was reversed and the purity increased as the wash sodium chloride was increased (black line). Additionally, the results indicate that the individual factors (wash sodium chloride and sodium caprylate) had a significant effect on recovery, again showing as an interaction between sodium caprylate and wash sodium chloride as can be seen by the quadratic interaction between wash sodium chloride and wash sodium chloride. The last column in Table 6 shows the significance of the effect.

TABLE 6

Recovery

| Parameter | "Prob > F" |
|---|---|
| Intercept | 1 |
| Wash pH (7, 9) | 0.68717 |

TABLE 6-continued

Recovery

| Parameter | "Prob > F" |
|---|---|
| Wash Sodium chloride (M) (0, 2.5) | 0.0003 |
| Sodium caprylate (mM) (0, 100) | 0.00043 |
| Wash pH*Wash Sodium chloride (M) | 0.88387 |
| Wash pH*Sodium caprylate (mM) | 0.92432 |
| Wash Sodium chloride (M)*Sodium caprylate (mM) | 0.00032 |
| Wash pH*Wash pH | 0.85434 |
| Wash Sodium chloride (M)*Wash Sodium chloride (M) | 0.04666 |
| Sodium caprylate (mM)*Sodium caprylate (mM) | 0.65567 |

Figure 4:
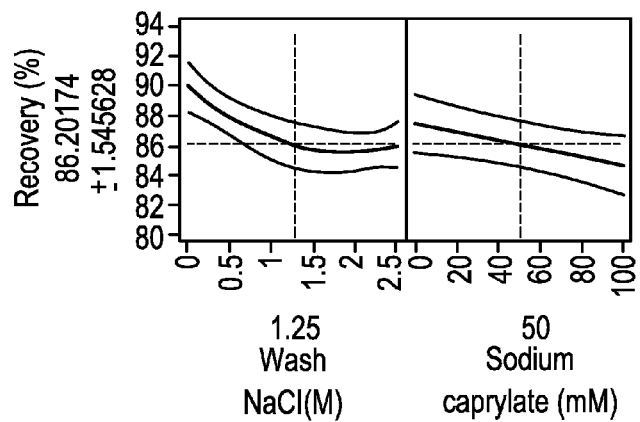
FIG. 4 shows the impact of the wash using sodium chloride and sodium caprylate on recovery.
Figure 5:
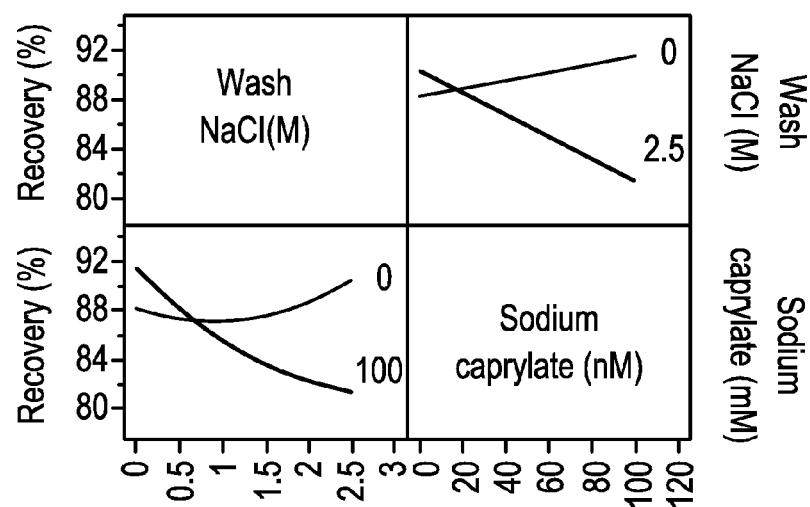
FIG. 5 shows the effect of the interaction between sodium chloride and sodium cparylate on recovery.

The effects of wash sodium chloride and sodium caprylate on recovery are shown in FIG. 4. Wash sodium chloride is represented by a curved line—a representation of the quadratic interaction of wash sodium chloride and sodium caprylate. The results in FIG. 4 show that increasing wash sodium chloride and sodium caprylate reduced the overall recovery by 2-4% each. FIG. 5 shows that, as wash sodium chloride was increased in the absence of sodium caprylate (bottom left), there was a slight increase in recovery (grey line). However, in the presence of sodium caprylate, there was a reduction in recovery (black line). The effect of sodium caprylate and wash sodium chloride is demonstrated in the top right corner—with no wash sodium chloride present there was an increase in recovery as the sodium caprylate was increased (grey line). However there was a decrease in recovery in the presence of high wash sodium chloride (black line).

The analysis for HCP pre-filtration identified a significant effect for all the individual factors (wash pH, wash sodium chloride and sodium caprylate) as well as an interaction between sodium caprylate and wash pH and a wash pH with wash sodium chloride. The last column in Table 7 shows the significance of the effect.

TABLE 7

HCP Pre-Filtration

| Parameter | "Prob > F" |
|---|---|
| Intercept | 1 |
| Wash pH (7, 9) | 0.0004 |
| Wash Sodium chloride (M) (0, 2.5) | 0.00172 |
| Sodium caprylate (mM) (0, 100) | 0.00014 |
| Wash pH*Wash Sodium chloride (M) | 0.01272 |
| Wash pH*Sodium caprylate (mM) | 0.04634 |
| Wash Sodium chloride (M)*Sodium caprylate (mM) | 0.55415 |
| Wash pH*Wash pH | 0.54008 |
| Wash Sodium chloride (M)*Wash Sodium chloride (M) | 0.31138 |

TABLE 7-continued

HCP Pre-Filtration

| Parameter | "Prob > F" |
|---|---|
| Sodium caprylate (mM)*Sodium caprylate (mM) | 0.62944 |

Increasing all three factors from low to high values resulted in a decrease in HCP levels in the eluate, suggesting that a wash buffer at pH 9.0, with 2.5M Sodium chloride and 100 mM sodium caprylate improved HCP clearance. This was confirmed experimentally. The lowest HCP levels achieved during the experiment was for run 7 (105.7 mg/mg). In contrast, the highest HCP level was observed with low values for the three factors in run 8 (1618 ng/mg).

Figure 6:
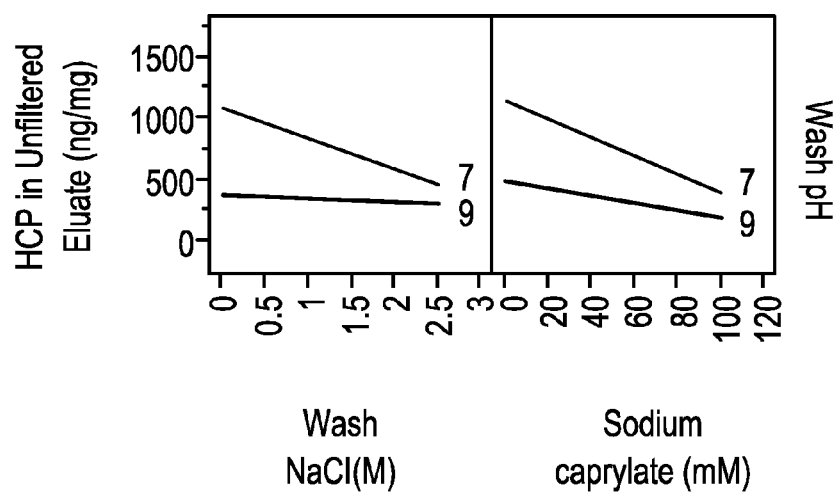
FIG. 6 shows the interactions between wash pH, wash sodium chloride and sodium caprylate on HCP levels (pre-filtration).

Additionally, two interactions were identified, which can be seen in FIG. 6. The interaction between wash pH and wash sodium chloride can be seen in the left box, which shows that there was only a little effect on HCP levels pre-filtration when wash sodium chloride was increased at pH 9 (black line) but shows a larger effect when the pH was reduced to 7 (grey line). The effect was the same for sodium caprylate—while HCP levels pre-filtration were lower at pH 9 with and without sodium caprylate (black line), the level of reduction was greater as sodium caprylate levels were increased at pH 7 (grey line).

The analysis identified a significant effect for all the individual factors (wash pH, wash sodium chloride and sodium caprylate) for HCP levels post-filtration, as well as interactions between sodium caprylate and wash pH, sodium caprylate and wash sodium chloride and two quadratic interactions, one with wash pH the other with wash sodium chloride. The last column in Table 8 shows the significance of the effects.

TABLE 8

HCP Post Filtration

| Parameter | "Prob > F" |
|---|---|
| Intercept | 1 |
| Wash pH (7, 9) | 0.00002 |
| Wash Sodium chloride (M) (0, 2.5) | 0.00001 |
| Sodium caprylate (mM) (0, 100) | 3.20E−08 |
| Wash pH*Wash Sodium chloride (M) | 0.78926 |
| Wash pH*Sodium caprylate (mM) | 0.70475 |
| Wash Sodium chloride (M)*Sodium caprylate (mM) | 2.68E−06 |
| Wash pH*Wash pH | 0.02018 |
| Wash Sodium chloride (M)*Wash Sodium chloride (M) | 0.00916 |
| Sodium caprylate (mM)*Sodium caprylate (mM) | 0.38244 |

Figure 7:
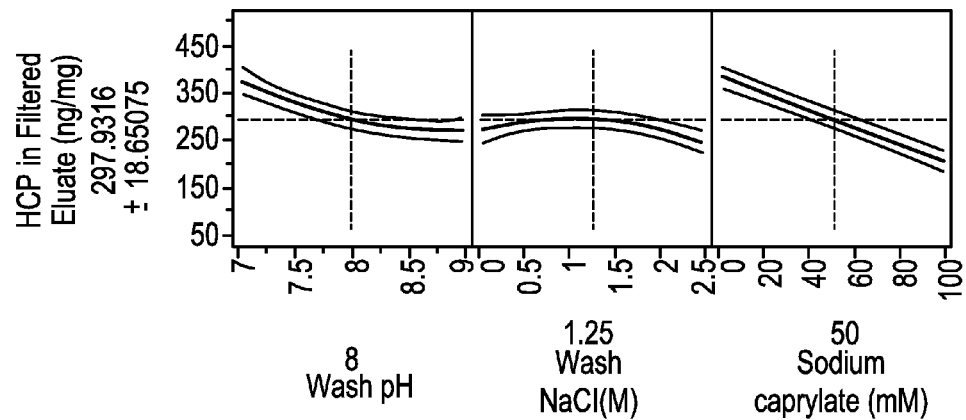
FIG. 7 shows the quadratic interactions for wash pH and sodium chloride on HCP levels (pre-filtration).

FIG. 7 shows HCP levels post-filtration with the two quadratic interactions represented by curved lines for wash pH and wash sodium chloride. The result for wash sodium chloride is interesting because the lowest HCP levels were achieved at high and low wash sodium chloride levels. This could be due to the samples with low wash sodium chloride having high HCP levels, which may have resulted in more turbidity and precipitation which was then removed by 0.2 µm filtration, thereby reducing the HCP level post-filtration.

Figure 8:
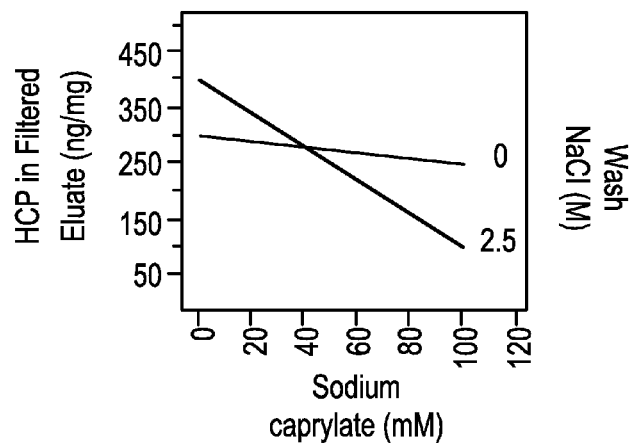
FIG. 8 shows the interaction between wash sodium chloride and sodium caprylate on HCP levels (post-filtration).

FIG. 8 shows the interaction between wash sodium chloride and sodium caprylate. In the absence of wash sodium chloride (grey line), less reduction in HCP post-filtration was observed than in the presence of 2.5M sodium chloride (black line).

Figure 9:
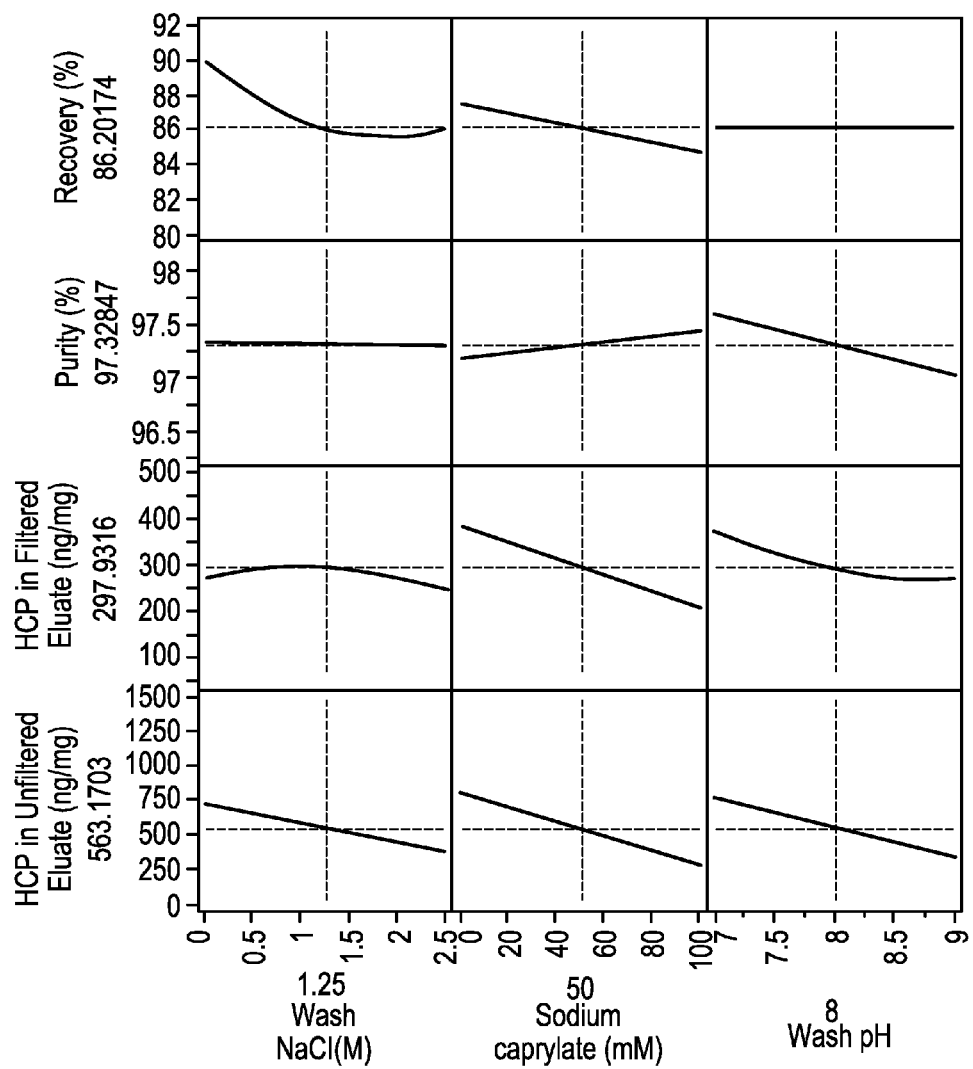
FIG. 9 shows the combined effects of wash pH, sodium chloride and sodium caprylate on purity, recovery and HCP levels pre-filtration.

The combined effect of each factor (wash pH, wash sodium chloride and sodium caprylate) on each response (purity, recovery, HCP pre-filtration and HCP post filtration) is shown in FIG. 9. The columns on the right hand side show that, as the wash pH was increased the HCP levels decreased indicating that a higher pH is better for HCP clearance. However, purity decreased as pH increased—a trait that is generally not desirable. FIG. 9 shows pH having no effect on recovery, because pH was not included in the model for recovery. The left hand column shows that increased wash sodium chloride reduced HCP. However, it also shows that increasing wash sodium chloride reduced recovery slightly and did not affect purity. The middle column shows that increasing sodium caprylate reduced HCP and increased purity. However, increasing sodium caprylate also reduced recovery. The predicted values using these conditions can be seen on the left hand axis.

FIGS. 10A-C show the combined effects of the three factors on HCP levels pre-filtration. All three graphs show that the lowest HCP levels were achieved when the factors were at their highest as indicated by the contour grid. This indicates that, for HCP removal, increasing the levels further may result in additional clearance of HCP. However, it may not be desirable to remove all HCPs at the expense of 50% product recovery. To optimise the conditions for all responses, a desirability function was added to the model and ranges were set for each response and an importance assigned. The importance for HCP removal was given the highest importance, since this was the purpose of the wash step. Recovery was assigned a higher importance than purity, because this is a capture step and aggregates could be removed by the additional steps in the process.

In FIG. 11, the optimal condition is displayed on the X axis in which both wash sodium chloride and sodium caprylate are still at the maximum values (i.e., 2.5 M and 100 mM, respectively), with a wash pH set at pH 8.45. Increasing the pH any further did not increase recovery or HCP clearance but did have a negative impact on purity. It is also important to note that a reasonably low recovery (81%) was observed under these conditions. For Protein A, a recovery of >90% would be expected. However, the wash sodium chloride was decreased to increase recovery, which in turn increased HCP levels. This suggests that the high levels of sodium chloride in the wash may have washed away product.

The experiment demonstrated that sodium caprylate and pH can affect eluate purity. Although increasing pH resulted in lower purities (which is undesirable), this is the wash step on a capture column and there are additional chromatography steps in the process for the removal of aggregates. Additionally, the results indicate that addition of sodium caprylate to the wash buffer increased purity. While not wishing to be bound by theory, it is believed that sodium caprylate removed HCPs by out-competing for binding sites on the antibody. If this is the case, then it would also explain why purity increased. Although the effects of sodium caprylate and wash sodium chloride on recovery were not entirely desirable, this may be outweighed by the reduction in HCP levels.

The results for HCP pre-filtration show that all three factors had the ability to reduce HCP levels when used in a Protein A wash buffer. Additionally, the results showed a synergistic interaction between wash pH and sodium caprylate that increased HCP clearance. Although the HCP levels post-filtration somewhat contradicted the HCP pre-filtration conclusions, the result for HCP pre-filtration were given more weight that the post-filtration levels because, even though the HCPs can be removed by filtration, the precipitate could block the filter making this less desirable in manufacturing.

Example 2: Effect of pH, Sodium Chloride and Sodium Caprylate on HCP Removal

The purpose of this experiment was to evaluate the effectiveness of three factors (pH, sodium chloride and sodium caprylate) and combinations thereof on HCP removal when included in a Protein A wash buffer for a second monoclonal antibody that specifically binds to human interleukin-6 (IL-6). The procedure was the same as described for Example 1, above. The results are shown in Table 9.

TABLE 9

Recovery, purity and HCP

| Run | Recovery (%) | Agg | Monomer | HCP (mg/mL) | HCP (ng/mg) | Relative protease activity (Intensity) at pH 7 after 5 hrs at 40 C. (ave of 3)* |
|---|---|---|---|---|---|---|
| 1 | 89.6 | 1 | 99 | 5291.06 | 453.7 | 25 |
| 2 | 88.4 | 1 | 99 | 3487.82 | 270.4 | 28 |
| 3 | 91.1 | 0.9 | 99.1 | 18116.3 | 1306.0 | 23 |
| 4 | 92.8 | 0.8 | 99.2 | 13144.2 | 921.9 | 25 |
| 5 | 81.1 | 1.4 | 98.6 | 1879.88 | 142.6 | 0 |
| 6 | 97.2 | 0.9 | 99.1 | 26385.3 | 1773.5 | 44 |
| 7 | 96.4 | 2.2 | 97.8 | 1319.62 | 91.5 | 0 |
| 8 | 80.6 | 0.9 | 99.1 | 12386.9 | 969.9 | 61 |
| 9 | 93.4 | 1 | 99 | 35504.4 | 2637.4 | 51 |
| 10 | 91.2 | 1 | 99 | 8742.6 | 635.1 | |
| 11 | 90.8 | 0.9 | 99.1 | 11230.2 | 803.5 | 29 |
| 12 | 94.3 | 1 | 99 | 13366.9 | 930.7 | 50 |
| 13 | 92.2 | 1 | 99 | 13428.6 | 938.0 | 33 |
| 14 | 83.0 | 0.9 | 99.1 | 16169.1 | 1274.2 | |
| 15 | 85.0 | 0.8 | 99.2 | 10385.1 | 821.4 | 46 |

TABLE 9-continued

Recovery, purity and HCP

| Run | Recovery (%) | Agg | Monomer | HCP (mg/mL) | HCP (ng/mg) | Relative protease activity (Intensity) at pH 7 after 5 hrs at 40 C. (ave of 3)* |
|---|---|---|---|---|---|---|
| 16 | 88.9 | 0.9 | 99.1 | 29621.7 | 2241.3 | 57 |
| 17 | 86.5 | 1.9 | 98.1 | 5972.23 | 474.6 | 0 |

The results in Table 10 show that purity was significantly affected by each factor (pH, sodium chloride and sodium caprylate) individually. Additionally, the results indicate an interaction between sodium caprylate and wash sodium chloride, and wash sodium chloride with wash pH. The effects of wash pH, sodium chloride and sodium caprylate on eluate purity are also shown in FIG. 12. From this is can be seen that increasing the levels of all three components resulted in a reduction in eluate purity.

FIG. 13 shows that, in the absence of sodium chloride, changing the levels of either the pH or sodium caprylate levels (black lines on left and right) had little effect on purity. However, in the presence of sodium chloride, there was a negative effect on the eluate purity when either sodium caprylate or pH increased (grey line on left and right). The recovery analysis only identified wash pH and its quadratic interaction as significant for recovery (Table 11). The results shown in FIG. 14 indicate that increasing the pH resulted in higher recovery values. Interestingly, the analysis for HCP in eluate only identified sodium caprylate as a significant factor (Table 12). The impact of sodium caprylate on HCP levels in eluate is shown in FIG. 15.

Due to the large levels of noise in the model, an alternate analysis was performed. The alternate analysis was a standard least squares analysis of the log HCP in eluate HCP values. The results from the alternate analysis show that wash sodium chloride had a significant effect and that there was an interaction between sodium caprylate and wash sodium chloride, as well as the effect of sodium caprylate individually (Table 13).

TABLE 10

Purity

| Parameter | "Prob > F" |
|---|---|
| Intercept | 1 |
| Wash pH (7, 9) | 0.07146 |
| Wash NaCl (M) (0, 2.5) | 0.00519 |
| Sodium caprylate (mM) (0, 100) | 0.02021 |
| Wash pH*Wash NaCl (M) | 0.06449 |
| Wash pH*Sodium caprylate (mM) | 0.40489 |
| Wash NaCl (M)*Sodium caprylate (mM) | 0.02306 |
| Wash pH*Wash pH | 0.17991 |
| Wash NaCl (M)*Wash NaCl (M) | 0.11551 |
| Sodium caprylate (mM)*Sodium caprylate (mM) | 0.41818 |

TABLE 11

Recovery

| Parameter | "Prob > F" |
|---|---|
| Intercept | 1 |
| Wash pH (7, 9) | 0.01709 |
| Wash NaCl (M) (0, 2.5) | 0.7095 |
| Sodium caprylate (mM) (0, 100) | 0.17451 |
| Wash pH*Wash pH | 0.06164 |
| Wash pH*Wash NaCl (M) | 0.83189 |
| Wash pH*Sodium caprylate (mM) | 0.40947 |
| Wash NaCl (M)*Wash NaCl (M) | 0.88938 |
| Wash NaCl (M)*Sodium caprylate (mM) | 0.52097 |
| Sodium caprylate (mM)*Sodium caprylate (mM) | 0.39495 |

TABLE 12

HCP In Eluate

| Parameter | "Prob > F" |
|---|---|
| Intercept | 1 |
| Wash pH (7, 9) | 0.44677 |
| Wash NaCl (M) (0, 2.5) | 0.23983 |
| Sodium caprylate (mM) (0, 100) | 0.00589 |
| Wash pH*Wash pH | 0.4861 |
| Wash pH*Wash NaCl (M) | 0.31068 |
| Wash pH*Sodium caprylate (mM) | 0.74476 |
| Wash NaCl (M)*Wash NaCl (M) | 0.47748 |
| Wash NaCl (M)*Sodium caprylate (mM) | 0.22755 |
| Sodium caprylate (mM)*Sodium caprylate (mM) | 0.37547 |

TABLE 13

Log HCP in Eluate

| Term | Prob > |t| |
|---|---|
| Intercept | <.0001* |
| Wash pH (7, 9) | 0.6705 |
| Wash NaCl (M) (0, 2.5) | 0.0323* |
| Sodium caprylate (mM) (0, 100) | 0.0029* |
| Wash pH*Wash NaCl (M) | 0.2971 |
| Wash pH*Sodium caprylate (mM) | 0.8843 |

TABLE 13-continued

| Log HCP in Eluate | |
|---|---|
| Term | Prob > \|t\| |
| Wash NaCl (M)*Sodium caprylate (mM) | 0.0262* |
| Wash pH*Wash pH | 0.3116 |
| Wash NaCl (M)*Wash NaCl (M) | 0.7846 |

The data in FIG. 16 shows the effects of the three factors on HCP levels. Increasing sodium caprylate levels showed the greatest effect on HCP levels. The interaction between wash sodium chloride and sodium caprylate can be seen in FIG. 17. In the absence of sodium chloride, there was a small decrease in the levels of HCP as sodium caprylate was increased (grey line). However, in the presence of sodium chloride, there was a further reduction in clearance as sodium caprylate was increased (black line).

The backward analysis for protease activity identified a significant effect for all the individual factors (wash pH, Wash Sodium chloride and sodium caprylate) as well as an interaction between sodium caprylate and wash pH, sodium caprylate and wash sodium chloride and wash pH and wash sodium chloride. The last column in Table 14 shows the significance of the effects.

TABLE 14

| Protease Activity | |
|---|---|
| Parameter | "Prob > F" |
| Intercept | 1 |
| Wash pH (7, 9) | 0.01128 |
| Wash NaCl (M) (0, 2.5) | 0.00097 |
| Sodium caprylate (mM) (0, 100) | 0.00125 |
| Wash pH*Wash NaCl (M) | 0.05577 |
| Wash pH*Sodium caprylate (mM) | 0.00985 |
| Wash NaCl (M)*Sodium caprylate (mM) | 0.09843 |
| Wash pH*Wash pH | 0.26659 |
| Wash NaCl (M)*Wash NaCl (M) | 0.5699 |
| Sodium caprylate (mM)*Sodium caprylate (mM) | 0.44294 |

FIG. 18 shows a clear decrease in protease activity for HCP levels post-filtration as each factor (wash pH, sodium chloride and sodium caprylate) was increased. FIG. 19 shows the interaction of wash pH and sodium caprylate. In particular, in the presence of sodium caprylate, there was little difference in the activity. However, in the absence of sodium caprylate increasing the wash pH reduced protease activity.

Figure 20B:
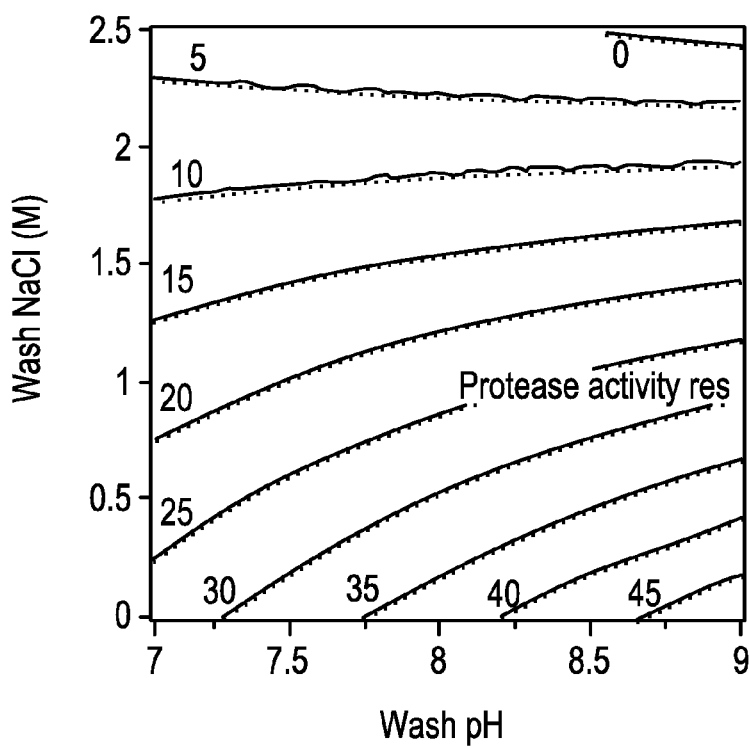

FIGS. 20A and B show the benefits of including sodium caprylate in the wash. FIG. 20 A shows protease activity in the absence of sodium caprylate. FIG. 20B shows protease activity in the presence of sodium caprylate. The lowest activity was observed in the absence of sodium caprylate (A), with a high pH and sodium chloride concentration. In contrast, the highest activity was observed with low pH and sodium chloride levels. However, in the presence of sodium caprylate the contours changed (B). The highest value was observed with high pH and no sodium chloride. As wash sodium chloride was increased, the contours flattened and the effect of pH was removed, since both pH 7 and 9 showed no activity. FIG. 21 displays all the effects in a single graph.

To improve HCP removal, wash sodium caprylate was set at the maximum value (i.e., 100 mM). (FIG. 22) Wash pH was set at pH 8.1, since increasing the pH any further resulted in a decrease in recovery and wash sodium chloride was set at 1.9 M, since increasing sodium chloride levels any further reduced purity. The results confirm that sodium caprylate and pH impact eluate purity. However, in this example, increasing all three factors resulted in a decrease in purity whereas for the IL-18 antibody in Example 1, there was an increase in purity in the presence of sodium caprylate. The three factors had little impact on recovery, except that a reduction in recovery was observed when wash pH was decreased. However, this could be attributed to noise from the other factors. Only sodium caprylate significantly affected HCP in the eluate. When a log transformation was performed to transform the data into a linear model, the results indicated that increasing wash sodium chloride and sodium caprylate reduced HPC values. The same was true for pH, although the effect was not as significant. As seen in the IL-18 antibody in Example 1, the optimum conditions include all three factors at their high value. The effect on protease activity mirrored the overall effect on HCP, which was expected. The combination of the results indicates that combining all three factors provides an improved wash for HCP removal.

Example 3: Evaluation of Other Fatty Acids for HCP Reduction

The purpose of this experiment was to evaluate the effectiveness of fatty acids other than sodium caprylate as constituents of a Protein A wash buffer on HCP removal for the monoclonal antibody used in Example 1 [an anti-IL-18 antibody]. The experiments were performed using the wash pH of 9.0 and 2.5M sodium chloride, the optimal conditions determined for the anti-IL-18 antibody in Example 1. All experimental wash buffers were made in 100 mM Tris and pH adjusted using HCl or Tris to achieve a final pH of 9.0. Based on solubility, some of the buffers included 2.5 M sodium chloride, while others were made without the 2.5 M sodium chloride, see Table 16. The Protein A chromatography buffers were prepared as described in Example 1 and the procedure was the same as described in Example 1. Table 15 provides a list of the unsaturated fatty acids and Table 16 provides the details for the experimental wash buffers.

TABLE 15

| unsaturated fatty acids | | | | |
|---|---|---|---|---|
| Common Name | Systematic Name | Structural Formula | No. Carbon Atoms | Class |
| Propionic acid | Propanoic acid | $CH_3CH_2COOH$ | 3 | Short |
| Butyric acid | Butanoic acid | $CH_3(CH_2)_2COOH$ | 4 | Short |

TABLE 15-continued unsaturated fatty acids

| Common Name | Systematic Name | Structural Formula | No. Carbon Atoms | Class |
|---|---|---|---|---|
| Valeric acid | Pentanoic acid | $CH_3(CH_2)_3COOH$ | 5 | Short |
| Caproic acid | Hexanoic acid | $CH_3(CH_2)_4COOH$ | 6 | Short/Medium |
| Enanthic acid | Heptanoic acid | $CH_3(CH_2)_5)COOH$ | 7 | Medium |
| Caprylic acid | Octanoic acid | $CH_3(CH_2)_6COOH$ | 8 | Medium |
| Pelargonic acid | Nonanoic acid | $CH_3(CH_2)_7COOH$ | 9 | Medium |
| Capric acid | Decanoic acid | $CH_3(CH_2)_8COOH$ | 10 | Medium |
| Undecylic acid | Undecanoic acid | $CH_3(CH_2)_9COOH$ | 11 | Medium |
| Lauric acid | Dodecanoic acid | $CH_3(CH_2)_{10}COOH$ | 12 | Medium/Long |
| Tridecylic acid | Tridecanoic acid | $CH_3(CH_2)_{11}COOH$ | 13 | Long |
| Myristic acid | Tetradecanoic acid | $CH_3(CH_2)_{12}COOH$ | 14 | Long |
| Pentadecylic acid | Pentadecanoic acid | $CH_3(CH_2)_{13}COOH$ | 15 | Long |
| Palmitic acid | Hexadecanoic acid | $CH_3(CH_2)_{14}COOH$ | 16 | Long |
| Margaric acid | Heptadecanoic acid | $CH_3(CH_2)_{15}COOH$ | 17 | Long |
| Stearic acid | Octadecanoic acid | $CH_3(CH_2)_{16}COOH$ | 18 | Long |
| Nonadecylic acid | Nonadecanoic acid | $CH_3(CH_2)_{17}COOH$ | 19 | Long |
| Arachidic acid | Eicosanoic acid | $CH_3(CH_2)_{18}COOH$ | 20 | Long |
| Heneicosylic acid | Heneicosanoic acid | $CH_3(CH_2)_{19}COOH$ | 21 | Long |
| Behenic acid | Docosanoic acid | $CH_3(CH_2)_{20}COOH$ | 22 | Long |
| Tricosylic acid | Tricosanoic acid | $CH_3(CH_2)_{21}COOH$ | 23 | Very Long |
| Lignoceric acid | Tetracosanoic acid | $CH_3(CH_2)_{22}COOH$ | 24 | Very Long |
| Pentacosylic acid | Pentacosanoic acid | $CH_3(CH_2)_{23}COOH$ | 25 | Very Long |
| Cerotic acid | Hexacosanoic acid | $CH_3(CH_2)_{24}COOH$ | 26 | Very Long |
| Heptacosylic acid | Heptacosanoic acid | $CH_3(CH_2)_{25}COOH$ | 27 | Very Long |
| Montanic acid | Octacosanoic acid | $CH_3(CH_2)_{26}COOH$ | 28 | Very Long |
| Nonacosylic acid | Nonacosanoic acid | $CH_3(CH_2)_{27}COOH$ | 29 | Very Long |
| Melissic acid | Triacontanoic acid | $CH_3(CH_2)_{28}COOH$ | 30 | Very Long |
| Henatriacontylic acid | Henatriacontanoic acid | $CH_3(CH_2)_{29}COOH$ | 31 | Very Long |
| Lacceroic acid | Dotriacontanoic acid | $CH_3(CH_2)_{30}COOH$ | 32 | Very Long |
| Psyllic acid | Tritriacontanoic acid | $CH_3(CH_2)_{31}COOH$ | 33 | Very Long |
| Geddic acid | Tetratriacontanoic acid | $CH_3(CH_2)_{32}COOH$ | 34 | Very Long |
| Ceroplastic acid | Pentatriacontanoic acid | $CH_3(CH_2)_{33}COOH$ | 35 | Very Long |
| Hexatriacontylic acid | Hexatriacontanoic acid | $CH_3(CH_2)_{34}COOH$ | 36 | Very Long |

TABLE 16 experimental wash buffers

| Buffer | Volume Buffer used (mL) | Fatty acid (100 mM) | Molecular weight | Amount Added (g) | Final pH |
|---|---|---|---|---|---|
| 100 mM Tris, 2.5M sodium chloride, pH 9.0 | 100 | Sodium Butyrate | 110.09 | 1.1009 | 9.02 |
| | 100 | Butyric acid | 88.11 | 0.8811 | 9.04 |
| | 100 | Sodium Hexanoate | 138.14 | 1.3814 | 8.98 |
| | 100 | Hexanoic acid | 116.16 | 1.1616 | 9.08 |
| 100 mM Tris, pH 9.0 | 100 | Sodium decanoate | 194.25 | 1.9425 | 9 |
| | 100 | Denoic acid | 172.26 | 1.7226 | 8.96 |
| | 100 | Sodium dodecanoate | 222.3 | 2.223 | 8.91 |
| | 100 | Lauric acid | 200.32 | 2.0032 | 9.01 |

The results are shown in Table 17. The purity for all runs was lower than expected. However, the reduction in purity could be due to the age of the anti-IL-18 antibody clarified harvest. Consequently, only HCP clearance and recovery were evaluated and compared to the control runs from the previous Examples.

TABLE 17

Results from fatty acid runs

| Run | Fatty acid (100 mM) | Recovery (%) | HCP Pre Filtration (ng/mg) | HCP Post Filtration (ng/mg) |
|---|---|---|---|---|
| 1 | Sodium Butyrate | 82.7621 | 844.0165 | 458.1015 |
| 2 | Butyric acid | 84.77823 | 599.8767 | 418.207 |
| 3 | Sodium Hexanoate | 89.86984 | 502.5348 | 418.1989 |
| 4 | Hexanoic acid | 85.96452 | | 408.2152 |
| 5 | Sodium decanoate | 79.20161 | 85.71799 | 140.7224 |
| 6 | Denoic acid | 75.82016 | 88.02499 | 138.5411 |
| 7 | Sodium dodecanoate | 41.01694 | | 106.9883 |
| 8 | Lauric acid | 46.96774 | 99.34895 | 118.2844 |

TABLE 18 control wash buffers with no fatty acids (from example 1)

| Run | Wash pH | Recovery (%) | HCP Pre-Filtration (ng/mg) | HCP Post-Filtration (ng/mg) |
|---|---|---|---|---|
| 6 | 9 | 88.18 | 577.56 | 296.41 |
| 10 | 9 | 89.94 | 599.00 | 365.58 |

The recoveries from runs 1-6 were comparable to those from the two control wash buffers. In runs 7 and 8, a significant reduction in recovery was observed (almost half that of the other runs). For these runs, a large peak was observed during the chromatography runs in the wash. Therefore, it appears that sodium dodecanoate and lauric acid result in a loss of recovery when added to a Protein A wash buffer.

FIG. 23 shows a large range in the levels of HCP levels pre-filtration: as high as 850 ng/mg for run 1 (using the short chain fatty acid sodium butyrate) and down to 85 ng/mg (using sodium dodecanoate). To determine whether these values demonstrate a decrease in eluate HCP, they were compared to the control buffer. Runs 1-4 were run in 100 mM tris, 2.5M sodium chloride, pH 9.0 (plus the fatty acid at 100 mM) and were compared to the second control run that also contained 2.5M sodium chloride (Table 18), which achieved a pre-filtration Protein A eluate HCP concentration of 599 ng/mg. Therefore, it can be seen that both sodium butyrate and butric acid (runs 1 and 2) did not demonstrate increased clearance of HCPs at the level tested. The values for sodium hexanoate (run 3) are slightly lower than the control (500 mg/mg compared with 599 ng/mg) demonstrating a small reduction over the control.

Sodium decanoate and denoic acid did not dissolve in the buffer containing 2.5M sodium chloride. Therefore, they should be compared to the buffer with no sodium chloride in (i.e., 100 mM tris, pH 9.0). The reduction from 600 ng/mg to 85 ng/ml and 97 ng/mg for sodium decanoate and denoic acid, respectively, represent a significant reduction in HCP levels. This was lower than the result obtained for sodium caprylate (206 ng/mg) obtained under the same conditions.

For sodium dodecanoate and lauric acid, the results were 88 and 99 ng/mg, respectively. However, the recovery was low (~45%). It is possible that the low recovery resulted in the low HCP levels, since it is possible that both product and HCP were washed from the column. However, further optimization could provide acceptable conditions for both HCP removal and recovery.

The post-filtration results for runs 1 to 4 are comparable to those for pre-filtration. HCP levels were reduced post filtration, likely due to precipitate removal during filtration.

The sodium decanoate and denoic acid runs (runs 5 and 6) demonstrated improved HCP removal as compared to the control wash conditions. Interestingly, the HCP levels were 140 ng/mg and 139 ng/mg, respectively, which were higher than the values pre-filtration. This could be due to an error in the HCP assay. Regardless of this variation, both the average and highest result represent a significant reduction in HCP levels compared to both the control buffer and the buffer containing sodium caprylate (Table 19). A summary of HCP levels in the eluate for the different fatty acid wash buffers is provided in FIG. 23.

TABLE 19

Results for sodium decanoate and denoic acid compared to control buffers

| | | Pre Filtration | |
| --- | --- | --- | --- |
| Fatty Acid (100 mM) | HCP Pre Filtration (ng/mg) | Reduction over sodium caprylate containing buffers (ng/mg) | Reduction over buffer (mg/mg) |
| sodium decanoate | 85.72 | 120.72 | 491.84 |
| decanoic acid | 88.02 | 118.42 | 489.54 |
| sodium caprylate | 206.44 | | |
| None | 577.56 | | |

It is clear that there was a wide variation in the removal of HCP for the fatty acids assessed. The short chain fatty acids and their sodium salts; including sodium butyrate, butric acid, did not result in lower HCP levels than the buffer controls. However, as the fatty acid chain length increased, from 4 to 6 for sodium hexanoate and hexanoic acid a reduction in HCP was observed, from 844 ng/mg to 502 ng/mg for the sodium salts and 844 ng/mg to 599 ng/mg for the fatty acid.

Sodium caprylate contains 8 carbon atoms and is classified as a medium chain fatty acid (7-12 carbon atoms). The results from the previous Examples demonstrated that sodium caprylate was able to reduce HCP levels to 206 mg/mg in a buffer containing 100 mM sodium caprylate in 100 mM Tris, pH 9. Similarly, the results for sodium decanoate, decanoic acid, sodium dodecanoate and lauric acid demonstrate that these fatty acids were also able to reduced HCP levels (to 150 ng/mg), indicating that medium chain fatty acids have the ability to reduce HCP when included in a Protein A wash buffer. Because it is important to maintain a high recovery during antibody purification, for example, to reduce the cost of goods, the reduced recovery observed with sodium dodecanoate and lauric acid was not entirely desirable. However, when balanced against the reduction in HCP levels, the reduction in recovery may be acceptable.

The results demonstrate that many fatty acids can be included in a Protein A wash buffer to reduce HCP levels. In general, the HCP levels were decreased as the chain length increased. In particular, the results suggest that medium chain length fatty acids may be the most desirable candidates due to the potentially undesirable effect on recovery observed with fatty acids having a chain length of 12 and the reduction of HCP removal observed with fatty acids having a chain length of 6. However, it may be possible to optimize the conditions to make these additional fatty acids viable components in Protein A wash buffers.

Example 4: The Effect of Caprylate Wash Buffers on HCP Removal During Protein a Chromatography The purpose of this experiment was to test the effectiveness of caprylate wash buffers for the removal of host cell protein (HCPs) for anti-IL-18 antibody (NCIMB Accession No. 41786) during Protein A chromatography. Two forms of caprylate; sodium caprylate and caprylic acid were tested at a concentration of 50 mM in a 100 mM Tris buffer containing 2.5M sodium chloride, pH 9.0. Four chromatography runs were performed using a MabSelect SurRe matrix (GE Healthcare) in a Tricorn 0.5 mm column with a bed height of 20 cm and a column volume of 3.98 mL at a linear flow rate of 350 cm/hr. Prior to use, the column was sanitized with 2 column volumes of 0.5M sodium hydroxide followed by a 15 minute hold with. The process buffers and column volumes are shown in Table 20. After use, the column was sanitized with 2 column volumes of 0.5M sodium hydroxide followed by a 15 minute hold. For eluate peak collection, OD was started at 100 mAU and ended at 100 mAU (0.50 D). All fractions were assayed at $A_{280}$ for protein concentration and HCP was quantified using the Gyros HCP assay described in Example 1.

TABLE 20

Process buffers and column volumes

| Step | Buffer | Column volumes | | | |
|---|---|---|---|---|---|
| | | Run 1 | Run 2 | Run 3 | Run 4 |
| Equilibration | 20 mM sodium phosphate, pH 7.0 | 5 | 5 | 5 | 5 |
| Load | Anti-IL-18 antibody Clarified Harvest | To 30 mg antibody/mL Matrix | To 30 mg antibody/mL Matrix | To 30 mg antibody/mL Matrix | To 30 mg antibody/mL Matrix |
| Re equilibration | 20 mM sodium phosphate, pH 7.0 | 10 | 5 | 5 | 5 |

Run 2 was a control run with one sodium caprylate wash and no second wash. However, the absence of a second wash resulted in a high sodium chloride concentration in the leading edge of the elution peak. The anti-IL-18 antibody used in this experiment (NCIMB Accession No. 41786) is known to phase separate at high salt concentrations and did so in this eluate. Run 2 was therefore discarded and not analysed. The results from the runs 1, 3 and 4 are also shown in Table 21.

TABLE 21

Results

| Run # | Recovery (%) | HCP (ng/mg) |
|---|---|---|
| 1 | 97.25 | 680.2 |
| 3 | 89.79 | 18.5 |
| 4 | 100 | 152.6 |

The results indicate that caprylic acid was capable of clearing HCP, but not to the same extent as sodium caprylate at the levels tested. In both cases, HCP levels were significantly reduced when compared to the control. In the control eluate, the level of HCP was 680 ng/mL, which was reduced 4 fold to 152 ng/mg in the caprylic acid experiment, and 35 fold in the sodium caprylate experiment. It is possible that increasing the concentration of the caprylic acid wash may further reduce the HCP in the eluate. The results demonstrate that both caprylic acid and sodium caprylate are capable of reducing HCP levels in Protein A eluates.

Example 5: Reduction of Host Cell Protease Induced Particle Formation

The purpose of this experiment was to investigate delayed-onset particle formation for an anti-IL6 antibody. Delayed onset particle formation was observed for in a formulation containing 50 mg/mL anti-IL6 antibody after 6 months at 5° C. The bioburden was 0 cfu/mL, indicating no bacterial contamination. A Mass Spec analysis of the particles revealed that the particles contained anti-IL6 antibody and elevated levels of fragments. No heavy elements were detected by SEM. No HCP was detected by 2D SDS PAGE (FIG. 24).

HCP levels in the eluate from Protein A purification was greater than 100 ng/mg when using a wash buffer that included 20 mM Tris, 1 M NaCl at pH 7.5 ("standard wash buffer"). Inclusion of a caprylate wash containing 100 mM Tris; 50 mM sodium caprylate, 2.5 M NaCl, pH 9.0 during Protein A purification reduced HCP levels from more than 100 ng/ml to less than 10 ng/ml. The purity of anti-IL6 antibody was measured by Size Exclusion Chromatography (SEC) using a TSK-GEL G3000SWXL column (Tosoh Bioscience LLC, Mongomeryville, Pa., USA) with UV detection at 280 nm. About 250 µg of protein was injected onto the assay column. Elution of soluble aggregates, monomer, and fragments occurred at approximately 6 to 8 min, 8.5 min, and 9 to 11.5 min respectively. A flow rate of 1.0 mL/min for 20 minutes using a pH 6.8 mobile phase containing 0.1 M sodium phosphate, 0.1 M sodium sulfate, and 0.05% (w/v) sodium azide was used to assay the samples.

SEC detected a higher fragmentation rate at 40° C. for anti-IL6 antibody lots with highest HCP levels (i.e., greater than about 100 ng/mg) (FIGS. 25 and 26). Anti-IL6 antibody samples were diluted to about 1 mg/mL in 1 mM pH 7.0 phosphate buffer and a 10 µL injection volumes were analyzed via reversed phase chromatography (RP-HPLC) for fragmentation. To perform the analyses a Michrom Bioresources (Auburn, Calif., USA) PLRP-S CM810092/00 column with a gradient elution at 75° C. using 0.1% TFA in water (mobile phase A, mp A) and 0.1% TFA (mp B) in acetonitrile was used. Species were eluted using a gradient of mp B (3 min hold at 5%, 5-34% over 3 min, 34-44% over 16 min, 44-75% over 2.5 min, followed by column conditioning at 95% for 8 min).

When analyzed using RP-HPLC at 40° C. the fragmentation rates were above about 3% per month for lots with highest HCP levels (i.e., greater than about 100 ng/mg) whereas lots that were purified with the caprylate wash step, with much lower HCP levels and without detectable protease activity, had fragmentation rates that were much lower at about 2 to 2.5% per month.

All lots with HCP levels greater than 100 ng/mg formed delayed-onset visible particles based on visual inspection (Table 24).

TABLE 24

HCP Level

| Lot | HCP level (ng/mg) | 0 mo. | 1 mo. | 2 mos. | 3 mos. | 6 mos. | 9 mos. | 12 mos. |
|---|---|---|---|---|---|---|---|---|
| A | 428 | <1 | <2 | Not done | <2 | 5 | 7 | 7 |
| B | 120 | <1 | <1 | 3 | 3 | <6 | 7 | 7 |
| C | 263 | <1 | <2 | <2 | 4 | 4 | 4 | 4 |
| D | 157 | <1 | <1 | 6 | 6 | 6 | 7 | 7 |
| E (w/wash) | 6 | <1 | <1 | <1 | 1 | 1 | 1 | 1 |
| F (w/wash) | 0.9 | <1 | <1 | <1 | 1 | 1 | 1 | 1 |
| G (w/wash) | <10 | <1 | <1 | <1 | 1 | 1 | 1 | 1 |

A fluorescent protease assay (Invitrogen EnzChek® Protease Assay Kit) was implemented to diagnose stability related to HCP proteases. All the lots with protease activity formed delayed onset particles. In contrast, the lots purified with caprylate wash (open symbols) did not demonstrate protease activity (See FIG. 27) and did not form delayed onset particles (Table 25).

TABLE 25

Protease Activity

| Lot | Scale | Protein A purification | HCP level (ng/mg) | Protease activity | SEC purity loss arte at 40° C. (%/mol) | RP-HPLC Frag. Rate at 40° C. (%/mol) | Delayed onset particles |
|---|---|---|---|---|---|---|---|
| A | 35 L | Standard Wash | 428 | Yes | 6.6 | 4.3 | Yes |
| B | 100 L | Standard Wash | 120 | Yes | 1.9 | 2.9 | Yes |
| C | 2 × 20 L | Standard Wash | 263 | Yes | 3.5 | 3.7 | Yes |
| D | 36 L | Standard Wash | 157 | Yes | 1.6 | 2.6 | Yes |
| E | 36 L | Caprylate Wash | 6 | No | 2.4 | 2.0 | No |
| F | 100 L | Caprylate Wash | 0.9 | No | 3.5 | 2.7 | No |
| G | 500 L | Caprylate Wash | <10 | No | 3.7 | 1.9 | No |

The results in Table 25 clearly demonstrate that the most stable lots (lots E, F and G) were the lots with the caprylate wash during Protein A purification. As shown in Table 26, lot D, which underwent a standard wash during Protein A purification and showed high HCP levels and detectable protease activity demonstrated significant particle formation at 3-12 months. In contrast, lot E, which was purified from the same cell culture media as lot D and had a significantly lower HCP level and no protease activity, showed very little particle formation over time. Thus, it appears that reducing HCP/protease levels with a caprylate wash during Protein A purification mitigates HCP protease-induced delayed-onset particle formation. It is believed that the best predictor of delayed onset particle formation is elevated HCP levels and protease activity.

Apartyl and serine protease activity were examined in particle forming Lot B using Invitrogen EnzChek® Protease Assay Kit for microplate HTS format. The results are shown in FIG. 28. Pepstatin (inhibitor of aspartyl proteases) dramatically reduced protease activity. AEBSF (serine protease inhibitor) had a smaller impact at higher pH (other serine inhibitors also had an impact). Other classes of inhibitors did not reduce protease activity (not shown)

then in the Protein A in-process product for both the standard and caprylate wash and in the wash fractions from the protein A step for both the standard and caprylate process.

A fluorescent protease assay (Invitrogen EnzChek® Protease Assay Kit) was used along with various commercially available protease inhibitors to detect and diagnose the presence and class/types of proteases present in the final drug substance and any intermediate purification samples. The EnzChek® Protease Assay Kit (E6638, Molecular Probes, Eugene, Oreg.) was used to assess protease activity in samples. The detection substrate in the kit is BODIPY®-casein conjugate. Samples were diluted 10-fold into 20 mM citrate-phosphate buffer at pHs typically ranging from 4 to 8. Matching placebos were prepared. The citrate-phosphate buffer was prepared by mixing 20 mM citric acid and 20 mM dibasic sodium phosphate to achieve the desired pHs. The preparation of reagents was adapted from the supplied procedure. The BODIPY®-casein conjugate detection substrate was diluted in the appropriate buffer to generate a working reagent at each pH from 4 to 8 at about 10 μg/mL. An equal (typically 100 μL) volume of sample and working reagent were added to wells in a white microplate to generate triplicate assay samples and matching placebos over the pH range 4 to 8. The samples were sealed and incubated at 40° C. for a typical duration of 3 to 5 hours. The dye fluorescence was excited at 485 nm and the emission intensity at 530 nm recorded using a 495 nm cutoff filter on a Molecular Devices SpectraMax® fluorescent plate reader (Sunnyvale, Calif.). The intensity vs. pH for the samples was recorded. Intensity increases of the sample compared to the

TABLE 26

Stability

| Lot | Purification Process | HCP level (ng/mg) | Protease activity | SEC purity loss rate at 40° C. (%/mol) | RP Frag. Rate at 40° C. (%/mol) | Visual Inspection results for particles at 5° C. (months) | | | | | |
|---|---|---|---|---|---|---|---|---|---|---|---|
| | | | | | | 0 | 1 | 3 | 6 | 9 | 12 |
| D | Standard wash | 157 | Yes | 1.6 | 2.6 | <1 | <1 | 6 | 6 | 7 | 7 |
| E | Caprylate wash | 6 | No | 2.4 | 2.0 | <1 | <1 | <1 | 1 | 1 | 1 |

Example 6: Identification of Host Cell Proteins at Various Points in the Purification Process In this example, the Host Cell Proteins (HCP) and high-throughput diagnosis of protease activity were examined and identified at several steps in the anti-IL6 purification process. Samples were analyzed from the cell culture media and blank of less than about 20% were dispositioned as negative for protease activity per the manufacturer guidelines based on variability in the method. Results for samples were buffer-subtracted and plotted vs. pH and used to determine the presence of protease activity in samples. Multiple replicates were run to assess the variability for low readings. For relative quantification, control preparations of known proteases such as Cathepsin-D or Trypsin as comparators were used. To confirm the presence of proteases, protease inhibitors were added to samples resulting in a relative decrease, or elimination, of the detected protease activity as a confirmation of the results.

Two dimensional mass spectrometry (2D-MS) was used to identify serine protease and aspartyl protease (cathepsin-D) in the cell culture media and in the various protein A product and wash steps. Two hundred and sixty-four HCPs were identified in the cell culture media, including proteases. Using a standard wash, 24 HCPs were observed in the protein A product In contrast, using a caprylate wash, only 8 HCPs were noted in the protein A product. The results clearly demonstrate that HCP reduction was achieved by caprylate treatment.

Because of the very low levels of proteases in the final drug substance, affinity purification and enrichment and concentration of the aspartyl protease (using Immobilized pepstatin, 786-789, G-Biosciences, St. Louis, Mo.) was needed to generate a sample with high enough protease levels to enable positive identification of the presence of cathepsin-D using mass spectrometry. Affinity purification was used to identify the proteases in the final drug substance. Immobilized pepstatin (786-789, G-Biosciences, St. Louis, Mo.) was used to capture, enrich and elute aspartyl proteases from the drug substance. The enriched sample was analyzed by 2D mass spectrometry to identify the protease. This affinity resin material contains the ligand that binds aspartyl proteases. The manufacturer's procedures were followed to bind the aspartyl proteases to the affinity resin, wash away the anti-IL6 antibody and finally elute the enriched/concentrated captured aspartyl proteases from the column for further analysis and identification. A large volume of drug substance was used to concentrate/enrich these samples to improve detectability.

The invention claimed is:

1. A method of reducing host cell protein (HCP) level in a composition comprising a recombinantly produced polypeptide, the method comprising:
providing a clarified cell culture supernatant comprising the recombinantly produced polypeptide and one or more HCP;
loading the clarified cell culture supernatant onto a Protein A chromatography column;
washing the Protein A chromatography column with a wash buffer comprising a fatty acid having a chain length of at least about 6 carbon atoms, or a fatty acid salt thereof to remove HCP; wherein the wash buffer comprises between about 25 mM to about 200 mM fatty acid; and wherein the wash buffer comprises sodium chloride present at a concentration of between about 1.0 M to about 2.5 M.

2. The method according to claim 1, wherein the HCP comprises one or more proteases.

3. The method according to claim 2, wherein the one or more proteases are selected from: serine proteases, aspartyl proteases, cysteine proteases, metalloproteases, aminopeptidases and combinations thereof.

4. The method of claim 1, wherein the chain length of the fatty acid or fatty acid salt is between 6 and 12 carbon atoms.

5. The method of claim 1, wherein the wash buffer has a pH between about 7 to about 9.

6. The method of claim 1, further comprising a step of clarifying the cell culture harvest to obtain a clarified cell culture harvest and loading the clarified cell culture harvest onto the Protein A chromatography column.

7. The method of claim 1, further comprising equilibrating the loaded Protein A column with an equilibration buffer prior to washing the column with the wash buffer.

8. The method of claim 7, wherein the equilibration buffer comprises sodium phosphate.

9. The method of claim 8, wherein the equilibration buffer comprises between about 10 mM and about 100 mM sodium phosphate.

10. The method of claim 1, further comprising a second wash step after the column is washed with the fatty acid wash buffer.

11. The method of claim 10, wherein the buffer used in the second wash step comprises sodium phosphate.

* * * * *